(12) United States Patent
Lawson et al.

(10) Patent No.: US 8,785,429 B2
(45) Date of Patent: Jul. 22, 2014

(54) DIHYDROPYRROLONAPHTHYRIDINONE COMPOUNDS AS INHIBITORS OF JAK

(71) Applicant: Takeda Pharmaceutical Company Limited, Osaka (JP)

(72) Inventors: John David Lawson, Carlsbad, CA (US); Toufike Kanouni, San Diego, CA (US); Michael B. Wallace, San Diego, CA (US); Qing Dong, San Diego, CA (US)

(73) Assignee: Takeda Pharmaceutical Company Limited

( * ) Notice: Subject to any disclaimer, the term of this patent is extended or adjusted under 35 U.S.C. 154(b) by 0 days.

(21) Appl. No.: 13/787,514

(22) Filed: Mar. 6, 2013

(65) Prior Publication Data

US 2013/0184252 A1 Jul. 18, 2013

Related U.S. Application Data

(62) Division of application No. 12/796,583, filed on Jun. 8, 2010, now Pat. No. 8,420,816.

(60) Provisional application No. 61/185,157, filed on Jun. 8, 2009.

(51) Int. Cl.
| | | |
|---|---|---|
| *A61K 31/4375* | (2006.01) | |
| *A61K 31/407* | (2006.01) | |
| *A61K 31/5025* | (2006.01) | |
| *C07D 471/16* | (2006.01) | |

(52) U.S. Cl.
USPC .............. 514/210.18; 514/253.03; 514/228.5; 546/82

(58) Field of Classification Search
None
See application file for complete search history.

(56) References Cited

U.S. PATENT DOCUMENTS

| | | | |
|---|---|---|---|
| 4,837,238 | A | 6/1989 | Markwell et al. |
| 6,514,982 | B1 | 2/2003 | Haddach et al. |
| 6,531,475 | B1 | 3/2003 | Haddach et al. |
| 6,600,028 | B1 | 7/2003 | Brown et al. |
| 7,049,303 | B2 | 5/2006 | Loakes et al. |
| 7,273,871 | B2 | 9/2007 | Di Fabio et al. |
| 7,329,667 | B2 | 2/2008 | Di Fabio et al. |
| 7,446,108 | B2 | 11/2008 | Di Fabio et al. |
| 2003/0130226 | A1 | 7/2003 | Loakes et al. |
| 2004/0087589 | A1 | 5/2004 | Haddach et al. |
| 2004/0157851 | A1 | 8/2004 | Haddach et al. |
| 2004/0198726 | A1 | 10/2004 | Di Fabio et al. |
| 2004/0242623 | A1 | 12/2004 | Difabio et al. |
| 2005/0043268 | A1 | 2/2005 | Loakes et al. |
| 2008/0009496 | A1 | 1/2008 | Daifuku et al. |

FOREIGN PATENT DOCUMENTS

| | | |
|---|---|---|
| EP | 01129091 | 9/2001 |
| EP | 01383498 | 1/2004 |
| EP | 01392689 | 10/2006 |
| EP | 01425281 | 12/2008 |
| EP | 02002836 | 12/2008 |
| WO | WO/00/27846 | 5/2000 |
| WO | WO01/87885 | 11/2001 |
| WO | WO/02/087573 | 11/2002 |
| WO | WO/02/094826 | 11/2002 |
| WO | WO/03/008414 | 1/2003 |
| WO | WO/03/039450 | 5/2003 |
| WO | WO/03/061385 | 7/2003 |
| WO | WO/03/087087 | 10/2003 |
| WO | WO/2005/062795 | 7/2005 |
| WO | WO/2005065150 | 7/2005 |
| WO | WO/2006/030031 | 3/2006 |
| WO | WO/2006030031 | 3/2006 |
| WO | WO/2007/056155 | 5/2007 |
| WO | WO/2007/070514 | 6/2007 |
| WO | WO/2005/065150 | 7/2007 |
| WO | WO/2007/077949 | 7/2007 |
| WO | WO/2007/117494 | 10/2007 |
| WO | WO/2008/079521 | 7/2008 |
| WO | WO/2008/084861 | 7/2008 |
| WO | WO/2008/100447 | 8/2008 |
| WO | WO/2009/843991 | 10/2008 |
| WO | WO/2008/150914 | 12/2008 |

OTHER PUBLICATIONS

Campbell, Brain Research Reviews, 2005, 48(2) 166-177.*
Boulton, Lee T. et al. "Zinc-mmediated intramolecular acyl and imino transfer reactions of aryl iodides" Tetrahedron Letters (2005) vol. 46, p. 983-986.
St-Denis, Y. et al. "Substitued tetraazaacenaphthylenes as potent CRF-1 receptor antagonists for the treatment of depression and anxiety" Bioorganic Medicinal Chemistry Letters (2005) vol. 15, p. 3713-3716.

* cited by examiner

*Primary Examiner* — Brandon Fetterolf
*Assistant Examiner* — Ana Z Muresan
(74) *Attorney, Agent, or Firm* — Matthew J. Russo; David M. Stemerick

(57) ABSTRACT

Disclosed are JAK inhibitors of formula I

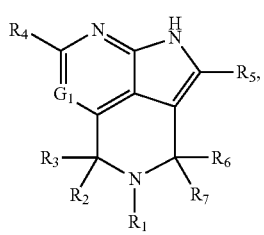

where $G_1$, $R_1$, $R_2$, $R_3$, $R_4$, $R_5$, $R_6$, and $R_7$ are defined in the specification. Also disclosed are pharmaceutical compositions, kits and articles of manufacture which contain the compounds, methods and materials for making the compounds, and methods of using the compounds to treat diseases, disorders, and conditions involving the immune system and inflammation, including rheumatoid arthritis, hematological malignancies, epithelial cancers (i.e., carcinomas), and other diseases, disorders or conditions associated with JAK.

17 Claims, No Drawings

DIHYDROPYRROLONAPHTHYRIDINONE COMPOUNDS AS INHIBITORS OF JAK

CROSS-REFERENCE TO RELATED APPLICATIONS

This application is a divisional of U.S. Ser. No. 12/796,583, filed Jun. 8, 2010, now U.S. Pat. No. 8,420,816, which claims the benefit of U.S. Provisional Application No. 61/185,157, filed Jun. 8, 2009, which are incorporated herein by reference.

FIELD OF THE INVENTION

The present invention relates to medicinal chemistry and pharmaceutical science. Provided herein are compounds that inhibit Janus kinase (JAK).

BACKGROUND OF THE INVENTION

The Janus Kinases (JAK) are a family of cytoplasmic protein tyrosine kinases including JAK1, JAK2, JAK3 and TYK2. Each of the JAK kinases is selective for the receptors of certain cytokines, though multiple JAK kinases may be affected by particular cytokine or signaling pathways, including the pathways for IL-2, IL-4, IL-7, IL-9, IL-15 and IL-21.

Phosphorylated JAK kinases bind various Signal Transducer and Activator of Transcription (STAT) proteins. STAT proteins are DNA binding proteins activated by phosphorylation of tyrosine residues and function both as signaling molecules and transcription factors and bind to specific DNA sequences of promoters of cytokine-responsive genes.

Cytokines influence cell differentiation, proliferation, and activation. Cytokines modulate both inflammatory and immune responses.

Abnormal JAK/STAT signaling is observed in conditions, such as allergies, asthma, autoimmune diseases such as transplant rejection, rheumatoid arthritis, amyotrophic lateral sclerosis, and multiple sclerosis, as well as in solid and hematologic malignancies such as leukemia and lymphomas. Inhibitors of the JAK pathway, particularly JAK3, are thought to be therapeutically useful for treating such conditions.

Certain JAK inhibitors are disclosed in WO 2007/077949 and WO 2008/084861.

SUMMARY OF THE INVENTION

The present invention provides compounds of formula I,

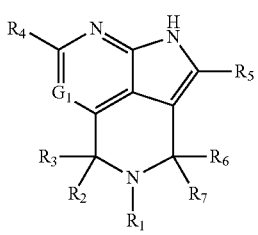

or pharmaceutically acceptable salts thereof, wherein:
$G_1$ is selected from the group consisting of N and $CR_8$;
$R_1$ is selected from the group consisting of optionally substituted $C_{3-8}$ cycloalkyl, optionally substituted $C_{3-6}$ heterocycloalkyl, optionally substituted $C_{4-14}$ aryl, optionally substituted $C_{1-10}$ heteroaryl, and optionally substituted $C_{1-6}$ alkyl;

$R_2$ and $R_3$ are each independently selected from the group consisting of hydrogen and optionally substituted $C_{1-4}$ alkyl, or $R_2$, $R_3$, and the carbon atom to which they are attached form a carbonyl;
$R_4$ is selected from the group consisting of hydrogen, optionally substituted $C_{1-4}$ alkyl, optionally substituted $C_{1-4}$ alkoxy, halo, hydroxy, and amino;
$R_5$ is selected from the group consisting of hydrogen, optionally substituted $C_{1-4}$ alkyl, $C_{3-8}$ cycloalkyl, and halo;
$R_6$ and $R_7$ are each independently selected from the group consisting of hydrogen and optionally substituted $C_{1-4}$ alkyl, or $R_6$, $R_7$, and the carbon atom to which they are attached form a carbonyl;
$R_8$ is selected from the group consisting of hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, and halo; and with the proviso that no more than one carbonyl is formed from $R_2$ and $R_3$ and $R_6$ and $R_7$.

One aspect of the invention provides a pharmaceutical composition, which includes a compound of formula I or a pharmaceutically acceptable salt as defined above, and a pharmaceutically acceptable excipient.

Another aspect of the invention provides a use as a medicament of a compound of formula I or a pharmaceutically acceptable salt as defined above.

An additional aspect of the invention provides a use of a compound of formula I or a pharmaceutically acceptable salt as defined above, for the manufacture of a medicament for the treatment of a disease, disorder or condition associated with JAK.

A further aspect of the invention provides a method of treating a disease, disorder or condition associated with JAK in a subject, the method comprising administering to the subject an effective amount of a compound of formula I or a pharmaceutically acceptable salt as defined above.

An additional aspect of the invention provides a method of treating a disease or condition in a subject, the method comprising administering to the subject an effective amount of a compound of formula I or a pharmaceutically acceptable salt as defined above, wherein the disease or condition is selected from allergic rhinitis, allergic asthma, atopic dermatitis, rheumatoid arthritis, multiple sclerosis, systemic lupus erythematosus, psoriasis, immune thrombocytopenic purpura, chronic obstructive pulmonary disease, and thrombosis.

Another aspect of the invention provides a method of treating a disease or condition in a subject, the method comprising administering to the subject an effective amount of a compound of formula I or a pharmaceutically acceptable salt as defined above, wherein the disease or condition is selected from a hematological malignancy and an epithelial cancer.

A further aspect of the invention provides a combination of an effective amount of a compound of formula I or a pharmaceutically acceptable salt as defined above, and at least one additional pharmacologically active agent.

The present invention also provides an article of manufacture comprising at least one compound of formula I and a label. Also provided are kits, which comprises at least one compound of formula I, a label, and apparatus for administration of the inhibitor.

The present invention also provides processes from making JAK inhibitors and intermediates thereof.

Compounds of this invention include all pharmaceutically acceptable complexes, salts, solvates, and hydrates of the compounds. Compounds of this invention also include all stereoisomers, tautomers, and polymorphic forms of the compounds, including all crystalline and amorphous forms, whether they are pure, substantially pure, or mixtures.

DETAILED DESCRIPTION OF THE INVENTION

Unless otherwise indicated, this disclosure uses definitions provided below.

The term "substituted," when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

The terms "about" or "approximately," when used in connection with a measurable numerical variable, refers to the indicated value of the variable and to all values of the variable that are within the experimental error of the indicated value (e.g., within the 95% confidence interval for the mean) or within ±10 percent of the indicated value, whichever is greater.

The term "$C_{2-4}$ alkenyl" refers to a straight or branched alkenyl chain having from two to four carbon atoms and one or more carbon-carbon double bonds, and includes ethylene, propylene, isopropylene, butylene, isobutylene, sec-butylene, and the like.

The term "$C_{1-4}$ alkyl" refers to a straight or branched alkyl chain having from one to four carbon atoms.

The term "optionally substituted $C_{1-4}$ alkyl" refers to a $C_{1-4}$ alkyl optionally having from 1 to 5 substituents independently selected from the group consisting of amino, $C_{1-7}$ amido, $C_{1-8}$ alkylamino, $C_{2-4}$ alkenyl, $C_{1-4}$ alkoxy, $C_{1-4}$ thioalkoxy, $C_{1-9}$ amide, $C_{1-5}$ oxycarbonyl, cyano, $C_{3-8}$ cycloalkyl, $C_{3-8}$ cycloalkoxy, halo, hydroxy, oxo, $C_{1-8}$ sulfonyl, optionally substituted $C_{1-10}$ heteroaryl, optionally substituted $C_{3-6}$ heterocycloalkyl, optionally substituted $C_{1-10}$ heteroaryl, and optionally substituted phenyl.

The term "$C_{1-6}$ alkyl" refers to a straight or branched alkyl chain having from one to six carbon atoms.

The term "optionally substituted $C_{1-6}$ alkyl" refers to a $C_{1-6}$ alkyl optionally having from 1 to 7 substituents independently selected from the group consisting of amino, $C_{1-7}$ amido, $C_{1-8}$ alkylamino, $C_{2-4}$ alkenyl, $C_{1-4}$ alkoxy, $C_{1-4}$ thioalkoxy, $C_{1-14}$ amide, $C_{1-5}$ oxycarbonyl, cyano, $C_{3-8}$ cycloalkyl, $C_{3-8}$ cycloalkoxy, halo, hydroxy, oxo, $C_{1-8}$ sulfonyl, optionally substituted $C_{1-10}$ heteroaryl, optionally substituted $C_{3-6}$ heterocycloalkyl, optionally substituted $C_{1-10}$ heteroaryl, and optionally substituted phenyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally having from 1 to 6 substituents independently selected from the group consisting of $C_{2-4}$ alkenyl, $C_{1-4}$ alkoxy, $C_{1-9}$ amide, $C_{1-5}$ oxycarbonyl, cyano, $C_{3-8}$ cycloalkyl, halo, hydroxy, optionally substituted $C_{1-10}$ heteroaryl, and optionally substituted phenyl.

The term "$C_{1-9}$ amide" refers to an amide having two groups independently selected from the group consisting of hydrogen and $C_{1-4}$ alkyl, e.g., —CONH$_2$, —CONHCH$_3$, and —CON(CH$_3$)$_2$.

The term "$C_{1-14}$ amide" refers to an amide (a) having two groups attached to the nitrogen atom which are independently selected from hydrogen and optionally substituted $C_{1-4}$ alkyl, e.g., —CONH$_2$, —CONHCH$_3$, and —CON(CH$_3$)$_2$; or an amide (b) having a hydrogen and a non-hydrogen substituent on nitrogen, wherein the non-hydrogen substituent is selected from optionally substituted $C_{1-4}$ alkyl, optionally substituted $C_{1-4}$ alkoxy, optionally substituted $C_{3-8}$ cycloalkyl, optionally substituted $C_{3-6}$ heterocycloalkyl, optionally substituted $C_{4-14}$ aryl, and optionally substituted $C_{1-10}$ heteroaryl, e.g., —CONH-(cyclopentyl), —CONH-(aryl), —CONH—CH$_2$-(phenyl), and so on.

The term "$C_{1-7}$ amido" refers to a —NHC(O)R group in which R is $C_{1-6}$ alkyl.

The term "$C_{1-5}$ carbamoyl" refers to an O- or N-linked carbamate having a terminal $C_{1-4}$ alkyl.

The term "$C_{1-5}$ ureido" refers to a urea having a $C_{1-4}$ alkyl.

The term "$C_{1-8}$ alkylamino" refers to an amino having one or two $C_{1-4}$ alkyl.

The term "$C_{4-14}$ aryl" refers to a monocyclic or polycyclic unsaturated, conjugated hydrocarbon having aromatic character and having four to fourteen carbon atoms, and includes phenyl, biphenyl, indenyl, cyclopentyldienyl, fluorenyl, and naphthyl.

The term "optionally substituted $C_{4-14}$ aryl" refers to a $C_{4-14}$ aryl optionally having 1 to 5 substituents independently selected from the group consisting of amino, $C_{1-8}$ alkylamino, $C_{1-7}$ amido, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halogen, hydroxy, nitro, $C_{1-5}$ oxycarbonyl, and $C_{1-8}$ sulfonyl.

The term "$C_{1-5}$ oxycarbonyl" refers to an oxycarbonyl group (—CO$_2$H) and $C_{1-4}$ alkyl ester thereof.

The term "$C_{3-8}$ cycloalkyl" refers to an alkyl ring having from three to eight carbon atoms, and includes cyclopropyl, 2-methyl cyclopropyl, cyclobutyl, cyclopentyl, cyclohexyl, and the like.

The term "optionally substituted $C_{3-8}$ cycloalkyl" refers to a $C_{3-8}$ cycloalkyl optionally having from 1 to 6 substituents independently selected from the group consisting of optionally substituted $C_{1-4}$ alkyl, $C_{2-4}$ alkenyl, $C_{1-4}$ alkoxy, $C_{1-9}$ amide, $C_{1-7}$ amido, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

The term "$C_{3-8}$ cycloalkoxy" refers to a $C_{3-8}$ cycloalkyl attached through an oxygen atom.

The terms "halogen" and "halo" refer to chloro, fluoro, bromo or iodo.

The term "$C_{3-6}$ heterocycloalkyl" refers to a 4 to 10 membered monocyclic saturated or partially (but not fully) unsaturated ring having one to four heteroatoms selected from the group consisting of nitrogen, oxygen, and sulfur. The nitrogen and sulfur heteroatoms may optionally be oxidized. For example, the term includes azetidine, pyrrolidine, piperidine, piperazine, morpholine, tetrahydropyran, tetrahydrofuran, hexahydropyrimidine, tetrahydropyrimidine, dihydroimidazole, and the like.

The term "optionally substituted $C_{3-6}$ heterocycloalkyl" refers to a $C_{3-6}$ heterocycloalkyl optionally substituted on the ring carbons with 1 to 4 substituents independently selected from the group consisting of optionally substituted $C_{1-4}$ alkyl, $C_{2-4}$ alkenyl, $C_{1-4}$ alkoxy, $C_{1-9}$ amide, $C_{1-7}$ amido, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, and optionally substituted phenyl; and optionally substituted on any ring nitrogen with a substituent selected from the group consisting of optionally substituted $C_{1-4}$ alkyl, $C_{2-4}$ alkenyl, $C_{3-8}$ cycloalkyl, optionally substituted $C_{3-6}$ heterocycloalkyl, optionally substituted $C_{1-10}$ heteroaryl, optionally substituted phenyl, and $C_{1-8}$ sulfonyl.

The term "$C_{1-10}$ heteroaryl" refers to a five to twelve membered monocyclic and polycyclic having unsaturated, conjugated ring(s) having aromatic character and having one to ten carbon atoms and one or more, typically one to four, heteroatoms selected from the group consisting of nitrogen, oxygen, and sulfur. The nitrogen and sulfur heteroatoms may optionally be oxidized. For example, the term includes azepine, diazepine, furan, thiophene, imidazole, isothiazole, isoxazole, oxadiazole, oxazole, pyrazine, pyrazole, pyridazine, pyridine, pyrimidine, thiazole, thiadiazole, triazole, tetrazole, benzazepine, benzodiazepine, benzofuran, benzothiophene, benzimidazole, imidazopyridine, pyrazolopyridine, pyrrolopyridine, quinazoline, thienopyridine, indolizine, imidazopyridine, quinoline, isoquinoline, indole, isoindole, benzoxazole, benzoxadiazole, benzopyrazole, benzothiazole, and the like.

The term "optionally substituted $C_{1-10}$ heteroaryl" refers to a $C_{1-10}$ heteroaryl optionally having 1 to 5 substituents on carbon independently selected from the group consisting of amino, $C_{1-7}$ amido, $C_{1-8}$ alkylamino, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halogen, hydroxy, oxo, nitro, $C_{1-5}$ oxycarbonyl, and $C_{1-8}$ sulfonyl, and optionally having substituents on each nitrogen independently selected from the group consisting of optionally substituted $C_{1-4}$ alkyl, $C_{1-8}$ sulfonyl, optionally substituted $C_{3-6}$ heterocycloalkyl, and optionally substituted phenyl.

The term "oxo" refers to an oxygen atom having a double bond to the carbon to which it is attached to form the carbonyl of a ketone, aldehyde, or amide. It is understood that the oxo can be attached to any available position on the group which has the oxo substituent. For example, an acetyl radical (—C(O)CH$_3$) is contemplated as an oxo substituted alkyl group and a pryidone radical is contemplated as oxo substituted $C_{1-10}$ heteroaryl.

The term "optionally substituted phenyl" refers to a phenyl group optionally having 1 to 5 substituents independently selected from the group consisting of amino, $C_{2-4}$ alkenyl, $C_{1-4}$ alkyl, $C_{1-4}$ alkoxy, $C_{1-9}$ amide, $C_{1-8}$ alkylamino, $C_{1-5}$ oxycarbonyl, cyano, halogen, hydrogen, hydroxy, nitro, $C_{1-8}$ sulfonyl, and trifluoromethyl.

The term "$C_{1-6}$ sulfonylamido" refers to a —NHS(O)$_2$—R group wherein R is $C_{1-6}$ alkyl.

The term "$C_{0-6}$ sulfonylamino" refers to a —S(O)$_2$NH—R group wherein R is selected from the group consisting of hydrogen and $C_{1-6}$ alkyl.

The term "$C_{1-4}$ thioalkoxy" refers to a $C_{1-4}$ alkyl attached through a sulfur atom.

The term "opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

The term "stereoisomers," when used in connection with a compound with given stereochemical configuration refers to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomers" refers to possible stereochemical configurations of the compound.

The phrase "substantially pure stereoisomer" and variants thereof refer to a sample containing a stereoisomer which comprises at least about 95% of the sample.

The phrase "pure stereoisomer" and variants thereof refer to a sample containing a stereoisomer which comprises at least about 99.5% of the sample.

The phrase "pharmaceutically acceptable" refers to those substances which are within the scope of sound medical judgment suitable for use in contact with the tissues of patients without undue toxicity, irritation, allergic response, and the like, commensurate with a reasonable benefit-to-risk ratio, and effective for their intended use.

The term "excipient" refers to any substance that may influence the bioavailability of a drug, but is otherwise pharmacologically inactive.

The term "pharmaceutically acceptable salt" refers to salts of pharmaceutically acceptable organic acids and bases or inorganic acids and bases. Potentially useful acid addition and base salts are described in S. M. Berge et al., *J. Pharm. Sci.* (1977) 66:1-19 and in Stahl and Wermuth, *Handbook of Pharmaceutical Salts: Properties, Selection, and Use* (2002). Examples of pharmaceutically acceptable salts include the hydrochloride and mesylate salts.

It is understood that, where the terms defined herein mention a number of carbon atoms, that the mentioned number refers to the mentioned group and does not include any carbons that may be present in any optional substituent(s).

The skilled artisan will appreciate that certain of the compounds of the present invention exist as isomers. All mixtures of stereoisomers, in any ratio, and specific geometric isomers, enantiomers, and diastereomers of the compounds of the invention are contemplated to be within the scope of the present invention.

The skilled artisan will appreciate that certain of the compounds of the present invention exist as tautomers. All tautomeric forms the compounds of the invention are contemplated to be within the scope of the present invention.

The phrase "compounds of the invention" refers to the compounds defined by formula I and specific compounds which fall within the scope of formula I, including compounds specifically named in the specification, examples, and claims.

Table 1 lists abbreviations used throughout the specification.

TABLE 1

List of Abbreviations

| Abbreviation | Description |
|---|---|
| Ac | acetyl |
| AcCN | acetonitrile |
| AcOH | acetic acid |
| AIBN | azo-bis-isobutyronitrile |
| APCI | atmospheric pressure chemical ionization |
| API | active pharmaceutical ingredient |
| aq | aqueous |
| Boc | t-butoxycarbonyl |
| BOP | benzotriazol-1-yloxy-tris-(dimethylamino)-phosphonium hexafluorophosphate |
| BSA | bovine serum albumin |
| n-Bu | normal butyl |
| Cbz | carbobenzyloxy |
| CYP | cytochrome P450 |
| DBU | 1,8-diazabicyclo[5.4.0]undec-7-ene |
| DCC | 1,3-dicyclohexylcarbodiimide |

TABLE 1-continued

List of Abbreviations

| Abbreviation | Description |
|---|---|
| DCE | dichloroethane |
| DCM | dichloromethane |
| de | diastereomeric excess |
| de | enantiomeric excess |
| DIPEA | N,N-diisopropylethylamine (Hünig's Base) |
| DMA | N,N-dimethylacetamide |
| DMAP | 4-dimethylaminopyridine |
| DMARD | disease modifying antirheumatic drug |
| DMF | N,N-dimethylformamide |
| DMSO | dimethylsulfoxide |
| DMT-MM | 4-(4,6-dimethoxy-1,3,5-triazin-2-yl)-4-methylmorpholinium chloride |
| dppf | 1,1'-bis(diphenylphosphino)ferrocene |
| DTT | dithiothreitol |
| EDA (Brj ®35) | ethoxylated dodecyl alcohol |
| EDC | N-(3-dimethylaminopropyl)-N'-ethylcarbodiimide |
| EDTA | ethylenediaminetetraacetic acid |
| eq | equivalents |
| er | enantiomeric ratio |
| ESI | electrospray ionization |
| Et | ethyl |
| Et$_3$N | triethyl-amine |
| EtOAc | ethyl acetate |
| EtOH | ethyl alcohol |
| FAM | 5-carboxyfluorescein |
| FDPP | pentafluorophenyl diphenylphosphinate |
| GC | gas chromatography |
| h, min, s | hour(s), minute(s), second(s) |
| HATU | 2-(3H-[1,2,3]triazolo[4,5-b]pyridin-3-yl)-1,1,3,3-tetramethyluronium hexafluorophosphate(V) |
| HBTU | 2-(1H-benzo[d][1,2,3]triazol-1-yl)-1,1,3,3-tetramethyluronium hexafluorophosphate(V) |
| HEPES | 4-(2-hydroxyethyl)piperazine-1-ethanesulfonic acid |
| HMPA | hexamethylphosphoramide |
| HOAt | 1-hydroxy-7-azabenzotriazole |
| HOBt | 1H-benzo[d][1,2,3]triazol-1-ol |
| HODhbt | 3-hydroxy-3,4-dihydro-4-oxo-1,2,3-benzotriazine |
| HPLC | high performance liquid chromatography |
| IC$_{50}$ | concentration at 50% inhibition |
| IPE | isopropylether |
| i-Pr | isopropyl |
| i-PrOH | isopropyl alcohol |
| LAH | lithium aluminum hydride |
| LC-MS | liquid chromatography-mass spectrometry |
| LDA | lithium diisopropylamide |
| Me | methyl |
| MEK | methylethylketone or butan-2-one |
| MeOH | methyl alcohol |
| MOI | multiplicity of infection |
| mp | melting point |
| MTBE | methyl tertiary butyl ether |
| NaOt-Bu | sodium tertiary butoxide |
| NBS | N-bromosuccinimide |
| NIS | N-iodosuccinimide |
| NMM | N-methylmorpholine |
| NMP | N-methylpyrrolidone |
| NMR, s, d, t, q, m, br | nuclear magnetic resonance, singlet, doublet, triplet, quartet, multiplet, broad |
| PE | petroleum ether |
| Ph | phenyl |
| pIC$_{50}$, | −log$_{10}$(IC$_{50}$), where IC$_{50}$ is given in molar (M) units |
| Pr | propyl |
| psi | pounds per square inch |
| PyBOP | (1H-benzo [d][1,2,3]triazol-1-yloxy)tripyrrolidin-1-ylphosphonium hexafluorophosphate(V) |
| R$_f$ | response factor |
| rt | room temperature (approximately 20° C. to 25° C.) |
| SEM | (2-(trimethylsilyl)ethoxy)methyl |
| TATU | 2-(3H-[1,2,3]triazolo[4,5-b]pyridin-3-yl)-1,1,3,3-tetramethyluronium tetrafluoroborate |
| TCEP | tris(2-carboxyethyl)phosphine |
| TFA | trifluoroacetic acid |
| THF | tetrahydrofuran |
| TLC | thin-layer chromatography |
| Tris buffer | 2-amino-2-hydroxymethyl-propane-1,3-diol buffer |
| Ts | tosyl |
| w/w or wt % | weight (mass) percent |

This disclosure concerns compounds of formula I, including compounds specifically named in the specification and claims, and their pharmaceutically acceptable complexes, salts, solvates and hydrates. This disclosure also concerns materials and methods for preparing compounds of formula I, pharmaceutical compositions containing them, and their use for treating disorders, diseases, and conditions involving the immune system and inflammation, including rheumatoid arthritis, as well as hematological malignancies, epithelial cancers (i.e., carcinomas), and other diseases, disorders or conditions associated with JAK. Compounds of formula I include the following embodiments.

a. One embodiment relates to compounds formula I in which R$_4$ is selected from the group consisting of hydrogen, C$_{1-4}$ alkyl, and halo.

b. Another embodiment relates to compounds of formula I in which R$_5$ is selected from the group consisting of hydrogen and C$_{1-4}$ alkyl.

c. Another embodiment relates to compounds of formula I in which R$_4$ is hydrogen.

d. Another embodiment relates to compounds of formula I in which R$_5$ is hydrogen.

e. Another embodiment relates to compounds of formula I in which each of R$_4$ and R$_5$ is hydrogen.

f. Another embodiment relates to compounds of formula I, and optionally any one of the above embodiments a, b, c, d, and e, in which G in formula I is CR$_8$.

g. Another embodiment relates to compounds of formula I, and optionally any one of the above embodiments a, b, c, d, and e, in which G in formula I is CR$_8$, and R$_8$ is selected from the group consisting of hydrogen, halo, and optionally substituted C$_{1-6}$ alkyl.

h. Another embodiment relates to compounds of formula I, and optionally any one of the above embodiments a, b, c, d, and e, in which G in formula I is CR$_8$, and R$_8$ is selected from the group consisting of hydrogen, halo, and C$_{1-4}$ alkyl.

i. Another embodiment relates to compounds of formula I, and optionally any one of the above embodiments a, b, c, d, and e, in which G in formula I is CR$_8$, and R$_8$ is halo.

j. Another embodiment relates to compounds of formula I, and optionally any one of the above embodiments a, b, c, d, and e, in which G in formula I is CR$_8$, and R$_8$ is C$_{1-4}$ alkyl.

k. Another embodiment relates to compounds of formula I, and optionally any one of the above embodiments a, b, c, d, and e, in which G in formula I is CR$_8$, and R$_8$ is methyl.

l. Another embodiment relates to compounds of formula I, and optionally any one of the above embodiments a, b, c, d, and e, in which G in formula I is N.

m. Another embodiment relates to compounds of formula I, and optionally any one of the above embodiments a, b, c, d, e, f, g, h, i, j, k, and l, in which R$_1$ in formula I is optionally substituted C$_{3-8}$ cycloalkyl.

n. Another embodiment relates to compounds of formula I, and optionally any one of the above embodiments a, b, c, d, e, f, g, h, i, j, k, and l, in which R$_1$ in formula I is optionally substituted C$_{3-6}$ heterocycloalkyl.

o. Another embodiment relates to compounds of formula I, and optionally any one of the above embodiments a, b, c, d, e, f, g, h, i, j, k, and l, in which $R_1$ in formula I is a nitrogen containing $C_{3-6}$ heterocycloalkyl substituted on a ring carbon with $C_{1-4}$ alkyl and substituted on a ring nitrogen with optionally substituted $C_{1-4}$ alkyl.

p. Another embodiment relates to compounds of formula I, and optionally any one of the above embodiments a, b, c, d, e, f, g, h, i, j, k, and l, in which $R_1$ in formula I is optionally substituted $C_{4-14}$ aryl.

q. Another embodiment relates to compounds of formula I, and optionally any one of the above embodiments a, b, c, d, e, f, g, h, i, j, k, and l, in which $R_1$ in formula I is optionally substituted $C_{1-10}$ heteroaryl.

r. Another embodiment relates to compounds of formula I, and optionally any one of the above embodiments a, b, c, d, e, f, g, h, i, j, k, and l, in which $R_1$ in formula I is optionally substituted $C_{1-6}$ alkyl.

s. Another embodiment relates to compounds of formula I, and optionally any one of the above embodiments a, b, c, d, e, f, g, h, i, j, k, and l, in which $R_1$ in formula I is $C_{1-6}$ alkyl having an oxo substituent and an optionally substituted $C_{3-6}$ heterocycloalkyl.

t. Another embodiment relates to compounds of formula I, and optionally any one of the above embodiments a, b, c, d, e, f, g, h, i, j, k, and l, in which $R_1$ in formula I is $C_{1-6}$ alkyl having an oxo substituent and an optionally substituted $C_{3-6}$ heterocycloalkyl attached to the same carbon atom of the $C_{1-6}$ alkyl group.

u. Another embodiment relates to compounds of formula I, and optionally any one of the above embodiments a, b, c, d, e, f, g, h, i, j, k, and l, in which $R_1$ in formula I is $C_{1-6}$ alkyl substituted with $C_{1-14}$ amide.

v. Another embodiment relates to compounds of formula I, and optionally any one of the above embodiments a, b, c, d, e, f, g, h, i, j, k, l, m, n, o, p, q, r, s, t, and u, in which $R_2$ and $R_3$ in formula I, together with the carbon atom to which they are attached, form a carbonyl.

w. Another embodiment relates to compounds of formula I, and optionally any one of the above embodiments a, b, c, d, e, f, g, h, i, j, k, l, m, n, o, p, q, r, s, t, and u, in which $R_2$ and $R_3$ in formula I, together with the carbon atom to which they are attached, form a carbonyl, and each of $R_6$ and $R_7$ in formula I is hydrogen.

x. Another embodiment relates to compounds of formula I, and optionally any one of the above embodiments a, b, c, d, e, f, g, h, i, j, k, l, m, n, o, p, q, r, s, t, and u, in which $R_6$ and $R_7$ in formula I, together with the carbon atom to which they are attached, form a carbonyl.

y. Another embodiment relates to compounds of formula I, and optionally any one of the above embodiments a, b, c, d, e, f, g, h, i, j, k, l, m, n, o, p, q, r, s, t, and u, in which $R_6$ and $R_7$ in formula I, together with the carbon atom to which they are attached, form a carbonyl, and each of $R_2$ and $R_3$ in formula I is hydrogen.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups, to avoid unwanted reactions. The selection, use, and removal of protecting groups is well known and appreciated as standard practice, for examples see T. W. Greene and P. G. M. Wuts, *Protective Groups in Organic Chemistry*, John Wiley and Sons (1991).

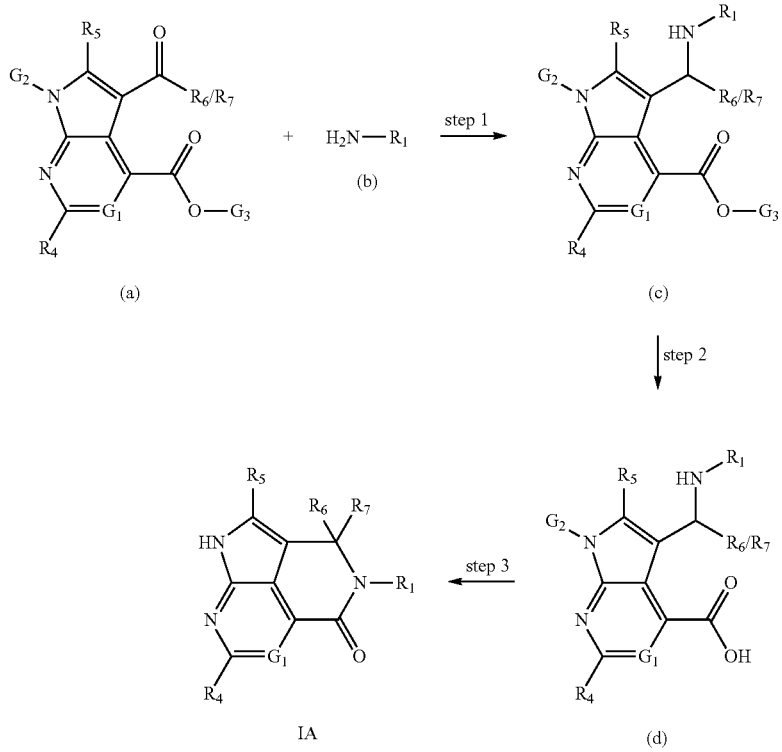

Scheme A depicts the formation of a compound of formula I in which $R_2$ and $R_3$ are taken together with the carbon atom to which they are attached to form a carbonyl (formula IA).

Scheme A, step 1, depicts the reaction of an appropriate compound of formula (a) with an appropriate compound of formula (b) to give a compound of formula (c). An appropriate compound of formula (a) is one in which $G_1$, $R_4$, and $R_6/R_7$ are as desired in the final compound of formula IA or gives rise to $G_1$, $R_4$, and $R_6/R_7$ as desired in the final compound of formula IA and $G_2$ is hydrogen or a protecting group and $G_3$ is $C_{1-4}$ alkyl, particularly methyl or ethyl. Compounds of formula (a) are readily prepared by a variety of methods including formylation of alkyl-pyrrolopyridine-4-carboxylate or alkyl-pyrrolopyrimidine-4-carboxylate and if desired by subsequent elaboration involving additions of organometallic reagents, oxidations, conversion to halogen and other reactions well known in the art. An appropriate compound of formula (b) is one in which $R_1$ is as desired in the final compound of formula IA or gives rise to $R_1$ as desired in the final compound of formula IA.

Specifically, Scheme A, step 1, depicts the reductive amination of a compound of formula (a) with an appropriate compound of formula (b) to give a compound of formula (c). For example, reductive aminations are carried out under a variety of conditions using reducing agents, such as sodium borohydride, sodium triacetoxyborohydride, zinc/hydrochloric acid, zinc borohydride, sodium cyanoborohydride, and the like. The reaction is carried out in a solvent, such as methanol, THF, and the like. Typically the reaction is carried out at a temperature which may range from about 0° C. to about 60° C. and typically requires from about 1 to about 24 hours to complete. When using sodium cyanoborohydride the reaction is carried out in a solvent, such as methanol, ethanol, isopropanol, and water or mixtures thereof. As is well known in the art, it may be advantageous to monitor and adjust the pH during such reactions.

Alternatively, such reductive amination reactions can be carried out by hydrogenation over a catalyst. A variety of catalysts are suitable for this purpose, including palladium, platinum, and nickel catalysts. Such hydrogenations are carried out in a suitable solvent such as ethyl acetate, ethanol, methanol, isopropanol, and the like, and are carried out at a pressure which may range from about atmospheric to about 300 psi (2068 kPa) and at a temperature which may range from about room temperature to about 100° C.

Scheme A, step 2, depicts the conversion of a compound of formula (c) to give a compound of formula (d). It will be recognized that the conversion of an ester to an acid is a common transformation and that there are numerous methods for effecting such a reaction, including hydrolysis using various acids and bases in water containing solvents.

Scheme A, step 3, depicts the formation of an amide bond converting a compound of formula (d) to a compound of formula IA. Such amide forming reactions are well understood and appreciated in the art. For example, standard amide forming conditions can be used, such as those using coupling agents, including those used in peptide couplings, such as 2-(3H-[1,2,3]triazolo[4,5-b]pyridin-3-yl)-1,1,3,3-tetramethyluronium hexafluorophosphate(V) (HATU), 1,3-dicyclohexylcarbodiimide (DCC), and N-(3-dimethylaminopropyl)-N'-ethylcarbodiimide (EDC) hydrochloride. If necessary or desired, an additive such as 4-(dimethylamino)pyridine, 1H-benzo[d][1,2,3]triazol-1-ol (HOBt), and the like may be used to facilitate the reaction. Such reactions are generally carried out using a base, such as N-methylmorpholine or triethylamine, in a wide variety of suitable solvents such as dichloromethane, dimethylformamide, THF, and the like.

Scheme B depicts the formation of a compound of formula I in which $R_6$ and $R_7$ are taken together with the carbon atom to which they are attached to form a carbonyl (formula IB). The process steps in Scheme B are the same as those depicted in Scheme A. However, the starting material, a compound of formula (a'), has a —C(O)OG$_3$ group in the 3-position and a carbonyl group (—C(O)—R$_2$/R$_3$) in the 4-position, which results in an oxo substitution at $R_6$ and $R_7$ of formula IA.

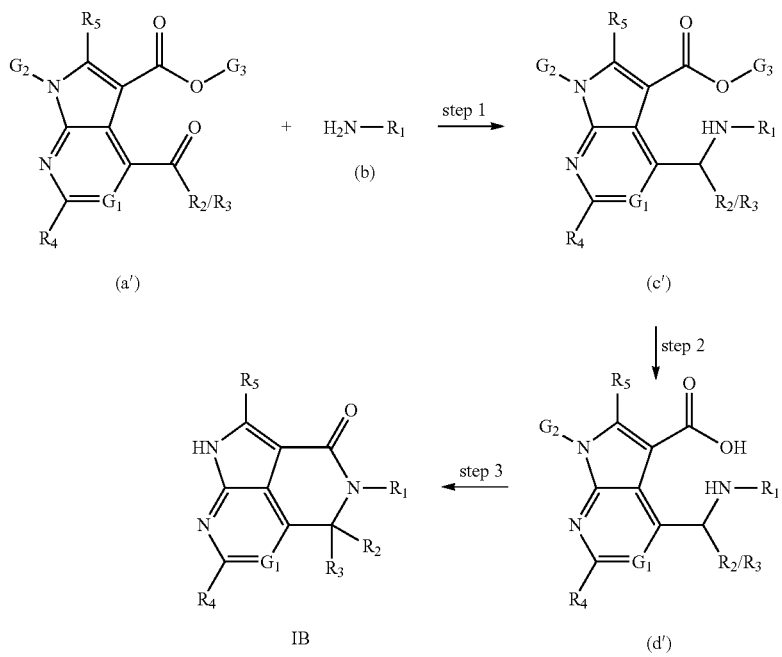

Scheme B

The processes depicted in Schemes A and B may be varied as desired. For example, protecting groups may be added or removed at various steps along the routes depicted in Schemes A and B. Also, a compound formed in step 3 can be further elaborated to give $R_1$ as desired in the final product, via alkylations, acylations, hydrolysis, oxidation, reduction, amidations, sulfonations, alkynations, alkyenations, and the like.

Also, in an optional step, not shown, a compound of formula I can be converted to a pharmaceutically acceptable salt. For example, a compound of formula I may be reacted with an appropriate acid or base to give the desired salt. Alternatively, a precursor of the compound of formula I may be reacted with an acid or base to remove an acid- or base-labile protecting group or to open a lactone or lactam group of the precursor. Additionally, a salt of the compound of formula I may be converted to another salt through treatment with an appropriate acid or base or through contact with an ion exchange resin. Following reaction, the salt may be isolated by filtration if it precipitates from solution or may be recovered by evaporation. The degree of ionization of the salt may vary from completely ionized to almost non-ionized.

Useful salts of the compound of formula I may include acid addition salts (including di-acids) and base addition salts. Pharmaceutically acceptable acid addition salts may include nontoxic salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Useful base addition salts may include nontoxic salts derived from bases, including metal cations, such as an alkali or alkaline earth metal cation, as well as amines. Examples of suitable metal cations may include sodium ($Na^+$), potassium ($K^+$), magnesium ($Mg^{2+}$), calcium ($Ca^{2+}$), zinc ($Zn^{2+}$), and aluminum ($Al^{3+}$). Examples of suitable amines may include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine.

The compounds of the invention can be administered alone or in the form of a pharmaceutical composition. In practice, the compounds of the invention are usually administered in the form of pharmaceutical compositions, that is, in admixture with at least one pharmaceutically acceptable excipient, the proportion and nature of which are determined by the properties of the selected compound of the invention, the chosen route of administration, and standard pharmaceutical practice.

In another embodiment, the present invention provides pharmaceutical compositions comprising: a compound of invention and a pharmaceutically acceptable excipient. One skilled in the art can readily select an amount, form, and route of administration depending upon the particular characteristics of the compound selected, the disorder or condition to be treated, the stage of the disorder or condition, and other relevant circumstances.

The pharmaceutical compositions of the present invention are prepared in a manner well known in the pharmaceutical art and include at least one of the compounds of the invention as the active ingredient. The amount of a compound of the present invention may be varied depending upon its particular properties and may conveniently be between about 1% to about 70% of the weight of the dosage form. The present pharmaceutical compositions are preferably formulated in a unit dosage form, each dosage typically containing from about 0.5 mg to about 200 mg of the compounds of the invention. The term "unit dosage form" refers to a physically discrete unit, each unit containing a predetermined quantity of active ingredient, in association with a suitable pharmaceutical excipient, by which one or more is used throughout the dosing regimen to produce the desired therapeutic effect.

In effecting treatment of a patient, a compound of the invention can be administered in any form and route which makes the compound bioavailable. The compounds of the invention can be administered by a variety of routes, including oral and parenteral routes, more particularly by inhalation, subcutaneously, intramuscularly, intravenously, transdermally, intranasally, rectally, vaginally, occularly, topically, sublingually, and buccally, intraperitoneally, intravenously, intraarterially, transdermally, sublingually, intramuscularly, rectally, transbuccally, intranasally, intraadiposally, and intrathecally. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient or an aid to the storage, administration, or manufacture of the composition. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

In one particular variation, the pharmaceutical composition is adapted for oral administration, such as a tablet or a capsule or a liquid formulation, for example, a solution or suspension, adapted for oral administration. In still another particular variation, the pharmaceutical composition is a liquid formulation adapted for parenteral administration.

In another embodiment, the invention provides methods of treating a disease, disorder or condition associated with JAK. The methods comprise administering to a patient in need thereof an effective amount of a compound of the invention. In another embodiment, the invention provides a method of inhibiting a JAK, comprising administering a compound of the invention to a patient in order to inhibit the JAK pathway in vivo. In a further embodiment, the invention provides a method of inhibiting a JAK, comprising administering a first compound to a subject that is converted in vivo to a compound of the invention.

In another embodiment, compounds of the invention are provided for use as a medicament. The invention also provides the use of compounds of the invention for the manufacture of a medicament to a treat disease, disorder or condition associated with JAK as described herein.

As used herein, the terms "condition," "disorder," and "disease" relate to any unhealthy or abnormal state. The phrase "disease, disorder or condition associated with JAK" includes any disease, disorder or condition in which the inhibition of JAK provides a therapeutic benefit, such as those characterized by abnormal JAK/STAT signaling, including proliferative disorders, cardiac disorders, neurodegenerative disorders, autoimmune disorders, organ transplant, inflammatory disorders, immunological disorders, and allergic conditions, food allergies, atopic dermatitis and rhinitis. Where general terms are used herein to describe conditions associated with JAK it is understood that the more specifically described conditions mentioned in the various diagnostic manuals and other materials are included within the scope of this invention. For example, it is understood that proliferative disorders include cancer. Furthermore, for example, it is understood arthritis is presently categorized into several more specific disorders, such as osteoarthritis and rheumatoid arthritis, and others, all of which are contemplated by the invention. Another example is systematic inflammatory response syndrome, which describes inflammation events associated with sepsis, pancreatitis, multiple trauma, lacerations, brain injury or surgery, hemorrhagic shock, immune-mediated organ injuries, and others, all of which are contemplated by the invention.

The terms "treat," "treatment," and "treating" include improvement of the disease, disorder or condition described herein. Also, it is recognized that one skilled in the art may affect the condition by treating a patient presently afflicted with the disease, disorder or condition by prophylactically treating a patient believed to be susceptible to the condition with an effective amount of a compound of invention. Thus, the terms "treat," "treatment," and "treating" include all processes which may slow, interrupt, arrest, control, or stop the progression of the diseases, disorders or conditions described herein, but do not necessarily indicate a total elimination of all symptoms or a cure. Thus, the use of such terms is intended to include prophylactic and therapeutic treatment of any particular disease, disorder or condition.

The terms "subject" and "patient" are used interchangeably and include humans and non-human animals, for example, mammals, such as mice, rats, guinea pigs, dogs, cats, rabbits, cows, horses, sheep, goats, and pigs. The terms also include birds, fish, reptiles, amphibians, and the like. It is understood that a more particular subject or patient is a human. Also, more particular subjects or patients are non-human mammals, such as mice, rats, and dogs.

As used herein, the term "effective amount" refers to the amount of compound of the invention which treats, upon single or multiple dose administration, a patient suffering from the disease, disorder or condition associated with JAK. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease; the response of the individual patient; the particular compound administered; the mode of administration; the bioavailability characteristics of the preparation administered; the dose regimen selected; the use of concomitant medication; and other relevant circumstances. An effective amount of the present use invention, including a compound of the invention, is expected to vary from about 0.1 milligram per kilogram of body weight per day (mg/kg/day) to about 20 mg/kg/day. Specific amounts can be determined by the skilled person.

As noted above, the compounds of formula I may be used to treat a disease, disorder or condition associated with JAK, and such diseases, disorders or conditions generally relate to any unhealthy or abnormal state in a subject for which the inhibition of JAK provides a therapeutic benefit. More particularly, such disorders, diseases, and conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, immune thrombocytopenic purpura, amyotrophic lateral sclerosis, and organ transplant rejection); inflammation of the lung (chronic obstructive pulmonary disease) and thrombosis. The compounds of formula I may also be used to treat disorders, diseases, and conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of formula I may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of formula I may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of formula I may also be used to treat autoimmune disorders in addition to those listed above. Such disorders, diseases, and conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, compounds of formula I may be used to treat inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemtic inflammatory response syndrome.

The compounds of formula I may also be used to treat specific diseases that may fall within one or more general disorders described above, including arthritis. In addition to rheumatoid arthritis, Sjögren's syndrome, systemic lupus erythematosus, SLE in children and adolescents, compounds of formula I may also be used to treat other arthritis diseases, including ankylosing spondylitis, avascular necrosis, Bechet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more diseases, disorders or conditions associated with JAK, including diseases, disorders or conditions involving the immune system, inflammation, and abnormal cell growth. For example, compounds of formula I, which include compounds specifically named in the specification and claims, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of formula I may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of formula I may be combined with one or more disease modifying anti-rheumatic drugs (DMARDs), and when treating osteoarthritis, the compounds of formula I may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-$\alpha$ inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of formula I and methotrexate, either alone, or in combination with one or more biological response modifiers, such as lefluonomide, etanercept, adalimumab, and infliximab.

For the treatment of thrombis and restensosis, the compounds of formula I may be combined with one or more cardiovascular agents such as calcium channel blockers, statins, fibrates, beta-blockers, ACE inhibitors, and platelet aggregation inhibitors.

The compounds of formula I may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and streptomyces (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include bacillus Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$, TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hetaptocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MEK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogenesis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

The invention also provides an article of manufacture, which comprises at least one compound of the invention and a label. The label may include information about the manufacturer, doses, conditions to be treated, and the use of the compound or pharmaceutical composition.

In another embodiment the invention provides a kit, which comprises at least one compound of the invention, a label, and apparatus for administration. The apparatus may include mixing vials, liquids for forming solutions or suspensions, tubing, syringes, and the like.

Biological Activity: JAK Inhibition

A compound's ability to inhibit JAK activity may be assessed using a variety of methods, including in vitro and in vivo assays. The following in vitro assays measure a test compound's ability to inhibit JAK2- and JAK3-mediated phosphorylation of FAM-labeled JAK-specific substrates.

Purified JAK2 and JAK3 proteins were purchased from Invitrogen. JAK2 and JAK3 inhibition is determined using a black 384-well-plate format in buffer containing 50 mM HEPES, 10 mM NaCl, 10 mM MgCl$_2$, 0.2 mM EDTA, 0.01% EDA (Brij® 35), 1 mM DTT, 0.1 mg/mL BSA at pH 7.3. Each test compound is prepared in DMSO using 2-fold serial dilutions for 11 data points and is added to the buffer so that each dilution contains 3% DMSO.

Assay for JAK2 Inhibition

To each well is added 2 µL of 3 µM 5FAM-KKKKEEIY-FFFG-NH$_2$ and 45 µM ATP (in buffer), 2 µL of diluted test compound (3% DMSO in medium), and 2 µL of 0.6 nM JAK2 in buffer. The reaction mixture is incubated at room temperature for 60 min and is quenched by adding 50 mM HEPeX, 30 mM EDTA, and 0.1% Tx-100 (pH 7.3). To quantify the fluorescent-labeled substrate and product following reaction, the test plate is loaded on a Caliper LC-3000, which measures percent of conversion by microfluidic-based separation.

Assay for JAK3 Inhibition

To each well is added 2 µL of 3 µM 5FAM-KKKKEEIY-FFFG-NH$_2$ and 15 µM ATP (in buffer), 2 µL of diluted test compound (3% DMSO in medium), and 2 µL of 1.2 nM JAK3 in buffer. The reaction mixture is incubated at room temperature for 60 min and is quenched by adding 50 mM HEPES, 30 mM EDTA, and 0.1% Tx-100 (pH 7.3). To quantify the fluorescent-labeled substrate and product following reaction, the test plate is loaded on a Caliper LC-3000, which measures percent of conversion by microfluidic-based separation.

Corresponding IC$_{50}$ values are calculated by non-linear curve fitting of the compound concentrations and percent of inhibition to the standard IC$_{50}$ equation.

EXAMPLES

The present invention is further illustrated by the following examples and preparations. The examples and preparations do not limit the scope of the invention in any way. $^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d$_6$ (deuterodimethylsulfoxide), CD$_3$OD (deuteromethanol), and THF-d$_8$ (deuterotetrahydrofuran). The mass spectra ([M+H]) were recorded using either electrospray ionization (ESI) or atmospheric pressure chemical ionization (APCI).

Where indicated, products of certain preparations and examples are purified by mass-triggered HPLC (Pump: Waters™ 2525; MS: ZQ™; Software: MassLynx™), flash chromatography or preparative thin layer chromatography (TLC). Preparative HPLC was carried out using either acidic or basic conditions. Acid conditions are typically gradients in Solvent A: water with 0.05% TFA and Solvent B: acetonitrile with 0.035% TFA; basic conditions are gradients in Solvent A: 10 nM $NH_4HCO_3$ in water and Solvent B: 10 nM $NH_4HCO_3$ in 20/80 (v/v) water/acetonitrile. The mentioned preparative HPLC conditions use acidic conditions unless indicated as basic. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Many of the abbreviations used in the examples are listed in Table 1, above. Abbreviations which are not listed in Table 1 have their usual meanings unless indicated otherwise in the specification.

Preparation A:

Methyl 3-formyl-1H-pyrrolo[2,3-b]pyridine-4-carboxylate

Methyl 1H-pyrrolo[2,3-b]pyridine-4-carboxylate (500 mg, 2.84 mmol) and hexamethylenetetramine (796 mg, 5.68 mmol) were combined in water (8 mL) and glacial acetic acid (16 mL) and heated at 100° C. overnight then cooled to room temperature. The reaction mixture was extracted with ethyl acetate and the organics were dried over $MgSO_4$ and concentrated in vacuo to give a residue. Purification of the residue by silica gel chromatography (50% EtOAc/Hexanes) gave the title compound as a white solid. $^1H$ NMR (400 MHz, DMSO-$d_6$) δ 10.07 (s, 1H), 8.57 (s, 1H), 8.48 (d, 1H, J=4.8 Hz), 7.48 (d, 1H, J=4.8 Hz), 5.74 (d, 1H, J=6.8 Hz), 3.91 (s, 3H), 2.78 (s, 3H). [M+H] found 205.

Preparation B:

1-tert-Butyl 4-methyl 3-formyl-1H-pyrrolo[2,3-b]pyridine-1,4-dicarboxylate

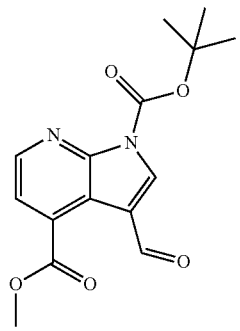 [SMILES: COC(=O)c1ccnc2c1c(C=O)cn2C(=O)OC(C)(C)C]

Methyl 3-formyl-1H-pyrrolo[2,3-b]pyridine-4-carboxylate (150 mg, 0.735 mmol) was dissolved in DMF (5 mL) and triethylamine (0.31 mL, 2.20 mmol) was added to the solution. Then di-tert-butyl-dicarbonate (240 mg, 1.10 mmol) was added and the mixture was allowed to stir for 3 h at room temperature. The solution was concentrated in vacuo. Purification by silica gel chromatography (30% EtOAc/Hexanes) gave 165 mg of the title compound as a white solid. $^1H$ NMR (400 MHz, $CD_3OD$) δ 10.16 (s, 1H), 8.64 (s, 1H), 8.57 (d, 1H, J=5.0 Hz), 7.63 (d, 1H, J=5.1 Hz), 4.00 (s, 3H), 1.72 (s, 9H). [M+H] found 305.

Example 1 tert-Butyl 4-(5-oxopyrrolo[4,3,2-de][2,6]naphthyridin-4(1H,3H,5H)-yl)piperidine-1-carboxylate Methyl 3-formyl-1H-pyrrolo[2,3-b]pyridine-4-carboxylate (160 mg, 0.784 mmol) and tert-butyl 4-aminopiperidine-1-carboxylate (188 mg, 0.940 mmol) were combined in MeOH (3 mL) and THF (3 mL) at 50° C. for 3 H. Then sodium borohydride (59 mg, 1.567 mmol) was added at room temperature and allowed to stir for 10 min. The mixture was quenched with water and extracted with ethyl acetate. The organics were dried over $MgSO_4$ and concentrated in vacuo to give methyl 3-((1-(tert-butoxycarbonyl)piperidin-4-ylamino)methyl)-1H-pyrrolo[2,3-b]pyridine-4-carboxylate (60 mg) which was carried on to the next step. $^1H$ NMR (400 MHz, $CD_3OD$) δ 8.32 (d, 1H, J=5.1 Hz), 7.61-7.62 (m, 2H), 4.07-4.13 (m, 4H), 4.01 (s, 3H), 2.81-2.84 (m, 3H), 1.96-1.98 (m, 2H), 1.45-1.47 (m, 2H), 1.45 (s, 9H). [M+H] found 389.

Methyl 3-((1-(tert-butoxycarbonyl)piperidin-4-ylamino)methyl)-1H-pyrrolo[2,3-b]pyridine-4-carboxylate (60 mg, 0.154 mmol) was stirred in MeOH (2 mL), 1N NaOH (3 mL), and THF (2 mL) for 16 h. Then 1N HCl was added dropwise until pH=5 and the mixture diluted with water and extracted with ethyl acetate. The organics were separated, dried over $MgSO_4$ and concentrated in vacuo. Purification by basic prep HPLC eluting with 10% to 35% B in A gave 50 mg 3-((1-(tert-butoxycarbonyl)piperidin-4-ylamino)methyl)-1H-pyrrolo[2,3-b]pyridine-4-carboxylic acid. $^1H$ NMR (400 MHz, $CD_3OD$) δ 11.84 (s, 1H), 8.21 (d, 1H, J=4.8 Hz), 7.67 (s, 1H), 7.34 (d, 1H, J=4.8 Hz), 4.14 (m, 2H), 3.96 (m, 2H), 3.04-3.09 (m, 1H), 2.77 (m, 2H), 2.02-2.03 (m, 2H), 1.42-1.43 (m, 2H), 1.40 (s, 9H). [M+H] found 375.

3-((1-(tert-Butoxycarbonyl)piperidin-4-ylamino)methyl)-1H-pyrrolo[2,3-b]pyridine-4-carboxylic acid (35 mg, 0.093 mmol), HATU (71 mg, 0.187 mmol), and pyridine (0.023 mL, 0.280 mmol) were stirred in DMF (3 mL) at room temperature for 2 h. The solution was concentrated in vacuo and purified via basic prep HPLC eluting with 10% to 35% B in A and gave 18 mg of the title compound as a yellow solid. $^1H$ NMR (400 MHz, $CD_3OD$) δ 7.59 (m, 1H), 7.39-7.49 (m, 1H), 4.98 (d, 2H, J=1.5 Hz), 4.77-4.79 (m, 1H), 4.25-4.28 (m, 2H), 2.87-2.92 (m, 2H), 1.91-1.94 (m, 2H), 1.78-1.90 (m, 2H), 1.48 (s, 9H). [M+H] found 357.

Example 2

4-(piperidin-4-yl)-3,4-dihydropyrrolo[4,3,2-de][2,6]naphthyridin-5(1H)-one

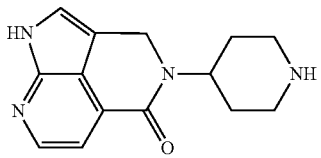 [SMILES: O=C1c2ccnc3[nH]cc(c23)CN1C1CCNCC1]

tert-Butyl 4-(5-oxopyrrolo[4,3,2-de][2,6]naphthyridin-4(1H,3H,5H)-yl)piperidine-1-carboxylate (18 mg, 0.051 mmol) was dissolved in TFA (1 mL) and DCM (2 mL) and allowed to stir at room temperature for 15 min. The mixture was concentrated in vacuo and purified via preparative HPLC 10% to 40% B in A and gave 12 mg of the title compound as its TFA salt. $^1$H NMR (400 MHz, CD$_3$OD) δ 8.71-8.72 (s, 1H), 8.42 (d, 1H, J=8.4 Hz), 7.62 (s, 1H), 7.48-7.49 (m, 2H), 5.02 (s, 1H), 4.69-4.75 (m, 2H), 3.58-3.61 (m, 2H), 3.19-3.26 (m, 2H), 2.33-2.39 (m, 2H), 2.10-2.15 (m, 2H). [M+H] found 257.

Example 3

3-oxo-3-(4-(5-oxopyrrolo[4,3,2-de][2,6]naphthyridin-4(1H,3H,5H)-yl)piperidin-1-yl)propanenitrile

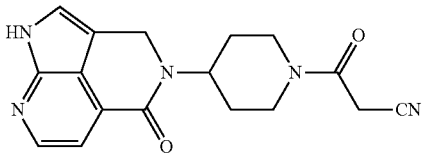 [SMILES: N#CCC(=O)N1CCC(N2Cc3c[nH]c4nccc(c34)C2=O)CC1]

4-(Piperidin-4-yl)-3,4-dihydropyrrolo[4,3,2-de][2,6]naphthyridin-5(1H)-one (34 mg, 0.133 mmol) and triethylamine (0.055 mL, 0.398 mmol) were dissolved in EtOH (4 mL) and cooled to 0° C. and allowed to stir for 10 min. Then 2,5-dioxopyrrolidin-1-yl 2-cyanoacetate (29 mg, 0.159 mmol) dissolved in EtOH (1 mL) was added dropwise and the mixture was allowed to stir for 30 min at 0° C. The solution was concentrated in vacuo and purified via preparative HPLC eluting with 10% to 40% B in A and gave 10 mg of the title compound as its TFA salt. $^1$H NMR (400 MHz, CD$_3$OD) δ 7.60 (m, 1H), 7.43 (m, 1H), 4.98 (s, 2H), 4.84-4.88 (m, 1H), 4.68-4.72 (m, 1H), 3.89-3.95 (m, 3H), 3.33 (m, 1H), 2.80-2.88 (m, 1H), 1.86-2.05 (m, 4H). [M+H] found 324.

Example 4 tert-butyl 4-methyl-4-(5-oxopyrrolo[4,3,2-de][2,6]naphthyridin-4(1H,3H,5H)-yl)piperidine-1-carboxylate

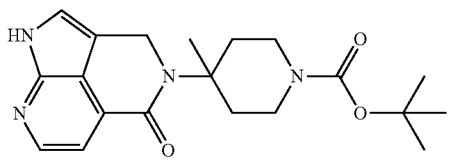 [SMILES: CC(C)(C)OC(=O)N1CCC(C)(N2Cc3c[nH]c4nccc(c34)C2=O)CC1]

1-tert-Butyl 4-methyl 3-formyl-1H-pyrrolo[2,3-b]pyridine-1,4-dicarboxylate (71 mg, 0.233 mmol) was dissolved in DCM (5 mL) and tert-butyl 4-amino-4-methylpiperidine-1-carboxylate (50 mg, 0.233 mmol) was added to the solution and allowed to stir for 2 h at room temperature. Then sodium triacetoxyborohydride (148 mg, 0.700 mmol) was added and the mixture was allowed to stir for 2 h at room temperature. The solution was quenched with water and extracted with DCM. The organics were dried over MgSO$_4$ and concentrated in vacuo. Purification by silica gel chromatography (70% EtOAc/Hexanes) gave 90 mg of 1-tert-butyl 4-methyl 3-((1-(tert-butoxycarbonyl)-4-methylpiperidin-4-ylamino)methyl)-1H-pyrrolo[2,3-b]pyridine-1,4-dicarboxylate. [M+H] found 403.

1-tert-Butyl 4-methyl 3-((1-(tert-butoxycarbonyl)-4-methylpiperidin-4-ylamino)methyl)-1H-pyrrolo[2,3-b]pyridine-1,4-dicarboxylate (90 mg, 0.179 mmol) was stirred in MeOH (2 mL), 1N NaOH (3 mL), and THF (2 mL) for 16 h. The mixture was concentrated in vacuo. Purification via basic preparative HPLC 15% to 35% B in A gave 34 mg of 341-(tert-butoxycarbonyl)-4-methylpiperidin-4-ylamino)methyl)-1H-pyrrolo[2,3-b]pyridine-4-carboxylic acid. [M+H] found 389.

3-((1-(tert-Butoxycarbonyl)-4-methylpiperidin-4-ylamino)methyl)-1H-pyrrolo[2,3-b]pyridine-4-carboxylic acid (34 mg, 0.088 mmol), HATU (67 mg, 0.175 mmol), and pyridine (0.021 mL, 0.263 mmol) were stirred in DMF (3 mL) at room temperature for 2 h. The solution was concentrated in vacuo to give the title compound which was used without further purification.

Example 5

4-(4-methylpiperidin-4-yl)-3,4-dihydropyrrolo[4,3,2-de][2,6]naphthyridin-5(1H)-one

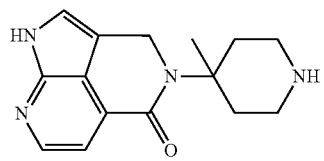 [SMILES: CC1(N2Cc3c[nH]c4nccc(c34)C2=O)CCNCC1]

The crude 3-((1-(tert-butoxycarbonyl)-4-methylpiperidin-4-ylamino)methyl)-1H-pyrrolo[2,3-b]pyridine-4-carboxylic acid obtained in Example 4 was dissolved in DCM (3 mL) and TFA (1 mL) and allowed to stir at room temperature for 1 h.

The solution was concentrated in vacuo and purified via preparative HPLC 5% to 20% B in A and gave 21 mg of the title compound as its TFA salt. $^1$H NMR (400 MHz, CD$_3$OD) δ 8.74 (s, 1H), 8.42 (m, 1H), 7.59 (m, 1H), 7.43 (m, 1H), 5.05 (s, 2H), 3.29-3.33 (m, 2H), 3.22-3.23 (m, 2H), 2.93-2.97 (m, 2H), 2.20-2.26 (m, 2H), 3.17 (s, 3H). [M+H] found 271.

Example 6

3-(4-methyl-4-(5-oxopyrrolo[4,3,2-de][2,6]naphthyridin-4(1H,3H,5H)-yl)piperidin-1-yl)-3-oxopropanenitrile

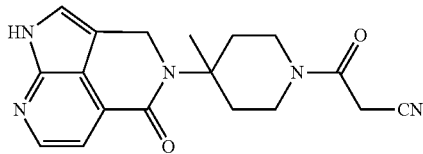 [SMILES: CC1(N2Cc3c[nH]c4nccc(c34)C2=O)CCN(C(=O)CC#N)CC1]

4-(4-Methylpiperidin-4-yl)-3,4-dihydropyrrolo[4,3,2-de][2,6]naphthyridin-5(1H)-one (21 mg, 0.078 mmol) and triethylamine (0.032 mL, 0.233 mmol) were dissolved in EtOH (4 mL) and cooled to 0° C. and allowed to stir for 10 min. Then 2,5-dioxopyrrolidin-1-yl 2-cyanoacetate (17 mg, 0.093 mmol) dissolved in EtOH (1 mL) was added dropwise and the mixture was allowed to stir for 30 min at 0° C. The solution was concentrated in vacuo and purified via preparative HPLC 10% to 40% B in A and gave 13 mg of the title compound as its TFA salt. $^1$H NMR (400 MHz, CD$_3$OD) δ 7.61 (m, 1H), 7.43 (m, 1H), 5.08 (s, 2H), 3.90 (m, 2H), 3.72 (m, 1H), 3.61-3.62 (m, 1H), 3.51-3.52 (m, 2H), 2.65-2.69 (m, 1H), 2.51-2.57 (m, 1H), 2.22-2.26 (m, 1H), 2.10-2.12 (m, 1H), 1.66 (s, 3H). [M+H] found 338.

Example 7 tert-butyl 4-ethyl-4-(5-oxopyrrolo[4,3,2-de][2,6]naphthyridin-4(1H,3H,5H)-yl)piperidine-1-carboxylate

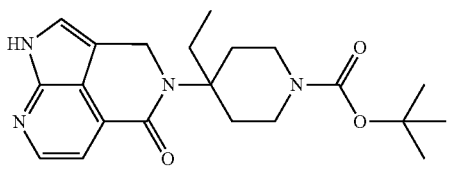 [SMILES: CCC1(N2Cc3c[nH]c4nccc(c34)C2=O)CCN(C(=O)OC(C)(C)C)CC1]

1-tert-Butyl 4-methyl 3-formyl-1H-pyrrolo[2,3-b]pyridine-1,4-dicarboxylate (211 mg, 0.692 mmol) was dissolved in MeOH (10 mL) and tert-butyl 4-amino-4-ethylpiperidine-1-carboxylate (158 mg, 0.692 mmol) were added followed by 2 drops of acetic acid. The solution was allowed to stir at room temperature for 2 h. Then sodium cyanoborohydride (44 mg, 0.692 mmol) was added over the course of 6 h at room temperature. The solution was quenched with water and extracted with ethyl acetate. The organics were dried over MgSO$_4$ and concentrated in vacuo. Purification by silica gel chromatography (70% EtOAc/Hexanes) gave 127 mg of 1-tert-butyl 4-methyl 3-((1-(tert-butoxycarbonyl)-4-ethylpiperidin-4-ylamino)methyl)-1H-pyrrolo[2,3-b]pyridine-1,4-dicarboxylate. [M+H] found 417.

1-tert-Butyl 4-methyl 3-((1-(tert-butoxycarbonyl)-4-ethylpiperidin-4-ylamino)methyl)-1H-pyrrolo[2,3-b]pyridine-1,4-dicarboxylate (123 mg, 0.238 mmol) was stirred in MeOH (3 mL), 1N NaOH (3 mL), and THF (2 mL) for 16 h. The mixture was concentrated in vacuo. Purification via basic prep HPLC 20% to 50% B in A gave 60 mg of 3-(1-(tert-butoxycarbonyl)-4-ethylpiperidin-4-ylamino)methyl)-1H-pyrrolo[2,3-b]pyridine-4-carboxylic acid. $^1$H NMR (400 MHz, CD$_3$OD) δ 8.29 (d, 1H, J=4.8 Hz), 7.68 (s, 1H), 7.52 (d, 1H, J=5.1 Hz), 4.31 (s, 2H), 3.95-4.01 (m, 1H), 2.03 (q, 2H, J=7.6 Hz), 1.92-1.94 (m, 4H), 1.47 (s, 9H), 1.46 (m, 2H), 1.07 (t, 1H, J=7.3 Hz). [M+H] found 403.

3-((1-(tert-Butoxycarbonyl)-4-ethylpiperidin-4-ylamino)methyl)-1H-pyrrolo[2,3-b]pyridine-4-carboxylic acid (50 mg, 0.124 mmol), HATU (94 mg, 0.248 mmol), and 4-dimethylaminopyridine (46 mg, 0.373 mmol) were stirred in DMF (3 mL) at room temperature for 1 h. The solution was concentrated in vacuo to give the title compound which was used without further purification.

Example 8

4-(4-ethylpiperidin-4-yl)-3,4-dihydropyrrolo[4,3,2-de][2,6]naphthyridin-5(1H)-one

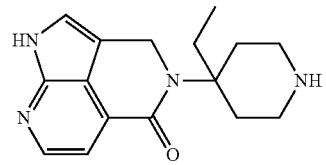

tert-Butyl 4-ethyl-4-(5-oxopyrrolo[4,3,2-de][2,6]naphthyridin-4(1H,3H,5H)-yl)piperidine-1-carboxylate (50 mg, 0.124 mmol), HATU (94 mg, 0.248 mmol), and 4-dimethylaminopyridine (46 mg, 0.373 mmol) were stirred in DMF (3 mL) at room temperature for 1 h. The solution was concentrated in vacuo and dissolved in DCM (3 mL) and TFA (1 mL) and allowed to stir at room temperature for 1 h. The solution was concentrated in vacuo and was purified via preparative HPLC 10% to 30% B in A and gave 28 mg of the title compound as its TFA salt. $^1$H NMR (400 MHz, CD$_3$OD) δ 7.36 (m, 1H), 7.27 (m, 1H), 5.04 (s, 2H), 3.22-3.34 (m, 2H), 3.19-3.21 (m, 2H), 2.95-2.98 (m, 2H), 2.13-2.23 (m, 4H), 0.97 (t, 3H, J=7.6 Hz). [M+H] found 285.

Example 9

3-(4-ethyl-4-(5-oxopyrrolo[4,3,2-de][2,6]naphthyridin-4(1H,3H,5H)-yl)piperidin-1-yl)-3-oxopropanenitrile

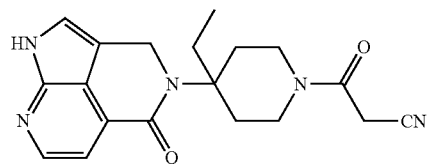 [SMILES: CCC1(N2Cc3c[nH]c4nccc(c34)C2=O)CCN(C(=O)CC#N)CC1]

4-(4-Ethylpiperidin-4-yl)-3,4-dihydropyrrolo[4,3,2-de][2,6]naphthyridin-5(1H)-one (25 mg, 0.088 mmol) and triethylamine (0.037 mL, 0.264 mmol) were dissolved in EtOH (3 mL) and cooled to 0° C. and allowed to stir for 10 min. Then 2,5-dioxopyrrolidin-1-yl 2-cyanoacetate (19 mg, 0.106 mmol) dissolved in EtOH (1 mL) was added dropwise and the mixture was allowed to stir for 30 min at 0° C. The solution was concentrated in vacuo and purified via preparative HPLC 10% to 50% B in A and gave 16 mg of the title compound as its TFA salt. $^1$H NMR (400 MHz, CD$_3$OD) δ 7.03 (m, 1H), 6.86 (m, 1H), 4.53 (d, 2H, J=2.0 Hz), 3.08-3.11 (m, 2H), 2.93-2.94 (m, 2H), 2.72-2.73 (m, 2H), 2.04-2.09 (m, 1H), 1.91-1.94 (m, 1H), 1.36-1.72 (m, 4H), 0.35 (t, 3H, J=7.6 Hz). [M+H] found 352.

Example 10

4-(pentan-3-yl)-3,4-dihydropyrrolo[4,3,2-de][2,6]naphthyridin-5(1H)-one

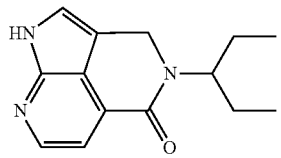 [SMILES: CCC(CC)N1Cc2c[nH]c3nccc(c23)C1=O]

Pentan-3-amine (18 mg, 0.21 mmol) was added to a solution of 1-tert-butyl 4-methyl 3-formyl-1H-pyrrolo[2,3-b]pyridine-1,4-dicarboxylate (40 mg, 0.13 mmol) in MeOH (3 mL) with AcOH (2 drops). After stirring for 90 min at rt, sodium cyanoborohydride (33 mg, 0.53 mmol) was added, and the mixture was stirred for an additional 3 h. The mixture was quenched with sat. NaHCO$_3$ solution and extracted with ethyl acetate. The organics were dried over MgSO$_4$ and concentrated in vacuo to give 42 mg of crude 1-tert-butyl 4-methyl 3-((penatan-3-ylamino)methyl)-1H-pyrrolo[2,3-b]pyridine-1,4-dicarboxylate as a clear oil which was used without further purification. [M+H] found 376.

1-tert-Butyl 4-methyl 3-((penatan-3-ylamino)methyl)-1H-pyrrolo[2,3-b]pyridine-1,4-dicarboxylate (42 mg, 0.11 mmol) was stirred in MeOH (3 mL) with 1N NaOH (1 mL) at 50° C. for 3 h. The reaction was cooled to rt, neutralized with 1N HCl, and concentrated in vacuo. The residue was dissolved in DMF (3 mL). HATU (71 mg, 0.187 mmol) was added, and the reaction stirred at rt for 2 h. The solution was concentrated in vacuo and purified by preparative HPLC eluting with a gradient of 15% to 70% Solvent B in Solvent A to give 16 mg of the title compound as an off-white solid. $^1$H NMR (400 MHz, CD$_3$OD) δ 8.33 (d, 1H, J=4.8 Hz), 7.38 (d, 1H, J=4.8 Hz), 7.18 (s, 1H), 4.76 (s, 2H), 4.68-4.80 (m, 1H), 1.60-1.71 (m, 4H), 0.87 (s, 6H). [M+H] found 244.

Example 11

4-(1-cyclopropyl-3-hydroxypropyl)-3,4-dihydropyrrolo[4,3,2-de][2,6]naphthyridin-5(1H)-one

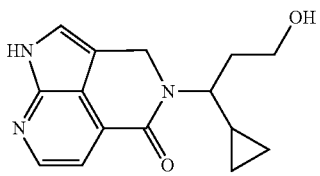 [SMILES: O=C1c2ccnc3[nH]cc(c23)CN1C(CCO)C1CC1]

3-Amino-3-cyclopropylpropan-1-ol (30 mg, 0.26 mmol) was added to a solution of 1-tert-butyl 4-methyl 3-formyl-1H-pyrrolo[2,3-b]pyridine-1,4-dicarboxylate (39.6 mg, 0.13 mmol) in MeOH (3 mL) with AcOH (2 drops). After stirring for 90 min at rt, sodium cyanoborohydride (33 mg, 0.53 mmol) was added, and the reaction was stirred for an additional 3 h. The mixture was quenched with sat. NaHCO$_3$ solution and extracted with ethyl acetate. The organics were dried over MgSO$_4$ and concentrated in vacuo to give 50 mg of crude 1-tert-butyl 4-methyl 34(1-cyclopropyl-3-hydroxypropylamino)methyl)-1H-pyrrolo[2,3-b]pyridine-1,4-dicarboxylate as a yellow oil which was used without further purification. [M+H] found 404.

1-tert-Butyl 4-methyl 3-((1-cyclopropyl-3-hydroxypropylamino)methyl)-1H-pyrrolo[2,3-b]pyridine-1,4-dicarboxylate (50 mg, 0.12 mmol) was stirred in MeOH (3 mL) with 1N NaOH (1 mL) at rt for 16 h. The reaction was neutralized with 1N HCl and concentrated in vacuo. The residue was dissolved in DMF (3 mL). HATU (47 mg, 0.12 mmol) was added, and the reaction stirred at room temperature for 2 h. The solution was concentrated in vacuo and purified by preparative HPLC eluting with a gradient of 15% to 70% Solvent B in Solvent A to give 16 mg of the title compound as an off-white solid. $^1$H NMR (400 MHz, CD$_3$OD) δ 8.34 (d, 1H, J=4.8 Hz), 7.35 (d, 1H, J=4.8 Hz), 7.28 (s, 1H), 5.10 (AB q, 2H, J=76.4, 16.8 Hz), 4.08-4.20 (m, 1H), 3.59 (t, 2H, J=6.4 Hz), 2.02-2.14 (m, 2H), 1.17-1.30 (m, 1H), 0.73-0.79 (m, 1H), 0.42-0.54 (m, 2H), 0.24-0.33 (m, 1H). [M+H] found 272.

Example 12

Tert-Butyl 3-((5-oxopyrrolo[4,3,2-de][2,6]naphthyridin-4(1H,3H,5H)-yl)methyl)pyrrolidine-1-carboxylate

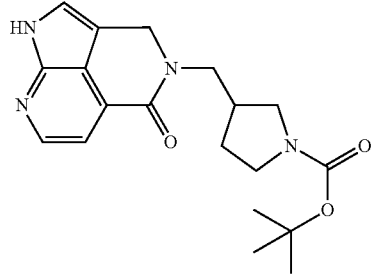 [SMILES: CC(C)(C)OC(=O)N1CCC(CN2Cc3c[nH]c4nccc(c34)C2=O)C1]

To a solution of 1-tert-butyl 4-methyl 3-formyl-1H-pyrrolo[2,3-b]pyridine-1,4-dicarboxylate (91 mg, 0.3 mmol) in MeOH (2 mL) was added AcOH (5 drops) and tert-butyl 3-(aminomethyl)pyrrolidine-1-carboxylate (90 mg, 0.45 mmol). After stirring for 60 min at rt, the reaction mixture was cooled to 0° C. Sodium cyanoborohydride (57 mg, 0.9 mmol) was added, and the reaction mixture was stirred for an additional 3 h at rt. The mixture was quenched with water and extracted with ethyl acetate. The combined organic layers washed with saturated NaHCO$_3$ and with brine, dried over Na$_2$SO$_4$, and concentrated in vacuo to give 125 mg of crude 1-tert-butyl 4-methyl 3-(((1-(tert-butoxycarbonyl)pyrrolidin-3-yl)methylamino)methyl)-1H-pyrrolo[2,3-b]pyridine-1,4-dicarboxylate as a colorless oil which was used without further purification. [M+H] found 489.40.

To a solution of 1-tert-butyl 4-methyl 3-(((1-(tert-butoxycarbonyl)pyrrolidin-3-yl)methylamino)methyl)-1H-pyrrolo[2,3-b]pyridine-1,4-dicarboxylate (70 mg, 0.143 mmol) in dioxane (2 mL) was added 1N LiOH (0.358 mL, 0.358 mmol) at 0° C. and stirred for 4 h at rt. The reaction mixture was extracted with ether and the aqueous layer was neutralized with 1N HCl, and concentrated in vacuo to afford 3-(((1-(tert-butoxycarbonyl)pyrrolidin-3-yl)methylamino)methyl)-1H-pyrrolo[2,3-b]pyridine-4-carboxylic acid as an off-white solid. [M+H] found 375.

3-(((1-(tert-Butoxycarbonyl)pyrrolidin-3-yl)methylamino)methyl)-1H-pyrrolo[2,3-b]pyridine-4-carboxylic acid was dissolved in DMF (3 mL). HATU (158 mg, 0.417 mmol) and DMAP (40 mg, 0.278 mmol) were added, and the reaction was stirred at rt for 2 h, concentrated in vacuo, and purified by preparative HPLC eluting with a gradient of 30% to 50% Solvent B in Solvent A to give 14.5 mg of the title compound as a light brown oil. $^1$H NMR (400 MHz, CD$_3$OD) δ 1.46 (br. s., 9 H) 1.70-1.81 (m, 1 H) 1.99-2.11 (m, 1 H) 2.78 (dt, J=14.34, 7.11 Hz, 1 H) 3.11-3.22 (m, 1 H) 3.32-3.36 (m, 1 H) 3.47-3.57 (m, 2 H) 3.72 (d, J=7.33 Hz, 1 H) 3.76-3.89 (m, 1 H) 5.09 (s, 2 H) 7.38 (s, 1 H) 7.51 (d, J=5.31 Hz, 1 H) 8.42 (d, J=5.56 Hz, 1 H). [M+H] found 357.

Example 13

4-(pyrrolidin-3-ylmethyl)-3,4-dihydropyrrolo[4,3,2-de][2,6]naphthyridine-5(1H)-one

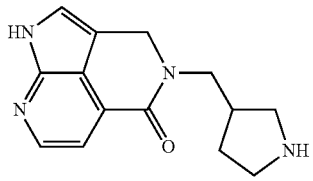 [SMILES: O=C1c2ccnc3[nH]cc(c23)CN1CC1CCNC1]

To a solution of tert-butyl 3-((5-oxopyrrolo[4,3,2-de][2,6]naphthyridin-4(1H,3H,5H)-yl)methyl)pyrrolidine-1-carboxylate (10 mg, 0.03 mmol) in dioxane at 0° C. was added 4N HCl in dioxane (0.019 mL, 0.075 mmol) and the reaction mixture was stirred for 1 h to give a solid. The solid was filtered and dried to afford the title compound (8.0 mg) as its HCl salt. $^1$H NMR (400 MHz, CD$_3$OD) δ 1.90 (br. s., 1 H) 2.24 (br. s., 1 H) 2.96 (br. s., 1 H) 3.17 (br. s., 2 H) 3.59 (d, J=5.05 Hz, 1 H) 3.71-3.83 (m, 2 H) 3.87 (br. s., 1 H) 5.18 (br. s., 2 H) 7.64 (br. s., 1 H) 7.80 (br. s., 1 H) 8.55 (br. s., 1 H). [M+H] found 257.

Example 14 tert-butyl 3-(5-oxopyrrolo[4,3,2-de][2,6]naphthyridin-4(1H,3H,5H)-yl)piperidine-1-carboxylate

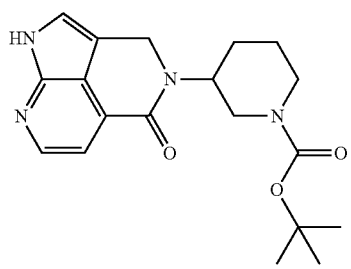 [SMILES: CC(C)(C)OC(=O)N1CCCC(N2Cc3c[nH]c4nccc(c34)C2=O)C1]

To a solution of 1-tert-butyl 4-methyl 3-formyl-1H-pyrrolo[2,3-b]pyridine-1,4-dicarboxylate (304 mg, 1.00 mmol) in 9:1 MeOH-Acetic Acid (2 mL) at 0° C. was added tert-butyl 3-aminopiperidine-1-carboxylate (300 mg, 1.50 mmol) and the reaction mixture was stirred at rt for 1 h. Sodium cyanotrihydroborate (314 mg, 5.00 mmol) was added slowly portionwise and the reaction mixture was stirred at rt over night, quenched with water, and extracted with ethyl acetate. The combined organic layers were washed with saturated NaHCO$_3$ and with brine, dried over Na$_2$SO$_4$, and concentrated in vacuo. The residue was purified by silica gel chromatography (30% to 70% Hexane-EtOAc) to give 307 mg of methyl 3-((1-(tert-butoxycarbonyl) piperidin-3-ylamino)methyl)-1H-pyrrolo[2,3-b]pyridine-4-carboxylate as a colorless oil. [M+H] found 389.

To a solution of methyl 3-((1-(tert-butoxycarbonyl)piperidin-3-ylamino)methyl)-1H-pyrrolo[2,3-b]pyridine-4-carboxylate (315 mg, 0.811 mmol) in dioxane (5 mL) at 0° C. was added 1N LiOH (2.03 mL, 2.03 mmol) and stirred for 4 h at rt. The reaction mixture was partitioned between ether and water. The separated aqueous layer was neutralized with 1N HCl, and concentrated in vacuo to afford 3-((1-(tert-butoxycarbonyl)piperidin-3-ylamino)methyl)-1H-pyrrolo[2,3-b]pyridine-4-carboxylic acid as an off-white solid. [M+H] found 375.

3-((1-(tert-butoxycarbonyl)piperidin-3-ylamino)methyl)-1H-pyrrolo[2,3-b]pyridine-4-carboxylic acid was dissolved in DMF (5 mL). HATU (914 mg, 2.4 mmol) and DMAP (196 mg, 1.6 mmol) were added, and the reaction stirred at rt for 2 h. The solution was concentrated in vacuo and purified by preparative HPLC eluting with a gradient of 30% to 50% Solvent B in Solvent A to give 123 mg of the title compound as a light yellow solid. $^1$H NMR (400 MHz, CD$_3$OD) δ 1.48 (s, 9 H) 1.59-1.70 (m, 1 H) 1.88 (d, J=13.39 Hz, 1 H) 1.95-2.02 (m, 1 H) 2.06 (dd, J=12.25, 3.92 Hz, 1 H) 2.75 (br. s., 1 H) 3.15 (t, J=11.62 Hz, 1 H) 4.04-4.20 (m, 2 H) 4.51 (br. s., 1 H) 4.93-5.14 (m, 2 H) 7.44 (s, 1 H) 7.58 (d, J=5.31 Hz, 1 H) 8.43 (d, J=5.56 Hz, 1 H). [M+H] found 357.

Example 15

4-(piperidin-3-yl)-3,4-dihydropyrrolo[4,3,2-de][2,6]naphthyridin-5(1H)-one

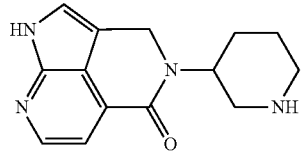 [SMILES: O=C1c2ccnc3[nH]cc(c23)CN1C1CCCNC1]

To a solution of tert-butyl 3-(5-oxopyrrolo[4,3,2-de][2,6]naphthyridin-4(1H,3H,5H)-yl)piperidine-1-carboxylate (10 mg, 0.028 mmol) in dioxane at 0° C. was added 4N HCl in dioxane (0.018 mL, 0.07 mmol) and the reaction mixture was stirred for 1 h to give a solid. The solid was filtered and dried to afford the title compound (5.6 mg) as its HCl salt. $^1$H NMR (400 MHz, CD$_3$OD) δ 1.82-2.13 (m, 2 H) 2.13-2.31 (m, 2 H) 3.02 (td, J=13.07, 2.91 Hz, 1 H) 3.41 (d, J=1.77 Hz, 1 H) 3.44-3.51 (m, 2 H) 4.68-4.84 (m, 1 H) 5.00-5.19 (m, 2 H) 7.59 (s, 1 H) 7.73 (d, J=6.06 Hz, 1 H) 8.52 (d, J=6.06 Hz, 1 H)). [M+H] found 257.

Example 16

4-(4-ethyl-1-propionylpiperidin-4-yl)-3,4-dihydropyrrolo[4,3,2-de][2,6]naphthyridin-5(1H)-one

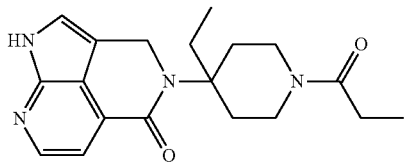 [SMILES: CCC(=O)N1CCC(CC)(N2Cc3c[nH]c4nccc(c34)C2=O)CC1]

4-(4-Ethylpiperidin-4-yl)-3,4-dihydropyrrolo[4,3,2-de][2,6]naphthyridin-5(1H)-one (12 mg, 0.042 mmol), propionic acid (4 mg, 0.055 mmol), 4-dimethylaminopyridine (10 mg, 0.084 mmol), and HATU (32 mg, 0.084 mmol) were dissolved in DMF (3 mL) at room temperature and allowed to stir for 3 h. The solution was concentrated in vacuo and purified via preparative HPLC 10% to 40% B in A and gave 4.6 mg of the title compound as its TFA salt. $^1$H NMR (400 MHz, CD$_3$OD) δ 7.58 (m, 1H), 7.41 (m, 1H), 5.12 (s, 2H), 3.70-3.74 (m, 1H), 3.59-3.63 (m, 3H), 2.58-2.61 (m, 1H), 2.41-2.43 (m, 3H), 2.21-2.30 (m, 4H), 1.11 (t, 3H, J=7.6 Hz), 0.94 (t, 3H, J=7.6 Hz). [M+H] found 341.

Example 17

4-(4-ethyl-1-(pyrimidin-4-yl) piperidin-4-yl)-3,4-dihydropyrrolo[4,3,2-de][2,6]naphthyridin-5(1H)-one

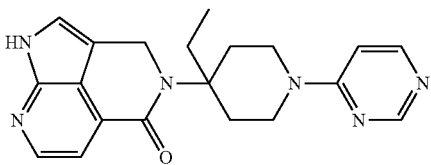 [SMILES: CCC1(N2Cc3c[nH]c4nccc(c34)C2=O)CCN(c2ccncn2)CC1]

4-(4-Ethylpiperidin-4-yl)-3,4-dihydropyrrolo[4,3,2-de][2,6]naphthyridin-5(1H)-one (10 mg, 0.035 mmol), triethylamine (0.049 mL, 0.352 mmol), and 4-chloropyrimidine (8 mg, 0.070 mmol) were dissolved in DMF (1.5 mL) and heated under microwave irradiation at 140° C. for 30 min. The solution was concentrated in vacuo and purified via preparative HPLC 10% to 40% B in A and gave 6.5 mg of the title compound as its TFA salt. $^1$H NMR (400 MHz, CD$_3$OD) δ 8.66 (s, 1H), 8.14 (dd, 1H, J=7.6, 1.3 Hz), 7.51 (s, 1H), 7.37 (s, 1H), 7.11 (d, 1H, J=7.5 Hz), 5.14 (s, 2H), 4.27 (m, 1H), 4.11 (m, 1H), 3.86-3.87 (m, 1H), 3.80-3.82 (m, 1H), 2.86 (m, 1H), 2.73 (m, 1H), 2.38 (m, 1H), 2.24-2.31 (m, 4H), 0.99 (t, 3H, J=7.6 Hz). MS (ES) [M+H] found 363.

Preparation C:

(S)-2-amino-1-(pyrrolidin-1-yl)butan-1-one

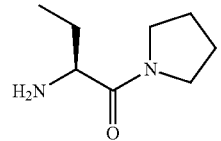

Step A: (S)-tert-butyl 1-oxo-1-(pyrrolidin-1-yl)butan-2-ylcarbamate

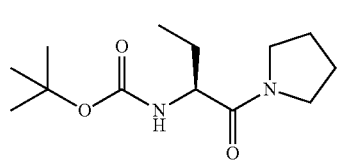 [SMILES: CC[C@H](NC(=O)OC(C)(C)C)C(=O)N1CCCC1]

To a mixture of (S)-2-(tert-butoxycarbonylamino)butanoic acid (1.4 g, 6.89 mmol), HATU (3.14 g, 8.27 mmol), and pyrrolidine (1.216 mL, 13.78 mmol) in DCM (50 mL) was added Et$_3$N (1.920 mL, 13.78 mmol). The reaction mixture was stirred at room temperature for 5 h and then washed with saturated aqueous NaHCO$_3$ and brine. The organics were dried over MgSO$_4$ and concentrated. Purification by silica column chromatography (MeOH/DCM, 0-10%) afforded the title compound as a light yellow oil (1.75 g, 99%). $^1$H NMR (500 MHz, CDCl$_3$) δ 0.94 (t, J=7.57 Hz, 3 H) 1.34-1.48 (m, 9 H), 1.49-1.68 (m, 1 H) 1.68-1.81 (m, 1 H) 1.81-1.92 (m, 2 H) 1.92-2.03 (m, 2 H) 3.34-3.47 (m, 2 H) 3.52 (dt, J=12.08, 7.14 Hz, 1 H) 3.65 (dt, J=10.13, 6.65 Hz, 1 H) 4.30-4.42 (m, 1 H) 5.35 (d, J=8.30 Hz, 1 H).

Step B: (S)-2-amino-1-(pyrrolidin-1-yl)butan-1-one (S)-tert-butyl 1-oxo-1-(pyrrolidin-1-yl)butan-2-ylcarbamate (1.75 g, 6.83 mmol) was stirred in 50% TFA/DCM (10 mL) for 1 h. The reaction mixture was concentrated and isolated as a clear oil, TFA salt. Purification by flash column chromatography (MeOH/DCM, 0-10%) afforded the title compound as a white solid (free base, 0.85 g, 5.44 mmol, 79%). $^1$H NMR (500 MHz, CDCl$_3$) δ 1.02 (t, J=7.45 Hz, 3 H) 1.78-2.01 (m, 6 H) 3.30-3.46 (m, 2 H) 3.51 (dt, J=12.20, 7.32 Hz, 1 H) 3.59 (dt, J=10.25, 6.59 Hz, 1 H) 4.14 (t, J=6.10 Hz, 1 H) 8.38 (br. s., 3 H).

Example 18

(S)-4-(1-oxo-1-(pyrrolidin-1-yl)butan-2-yl)-4,5-dihydropyrrolo[4,3,2-de][2,6]naphthyridin-3(1H)-one

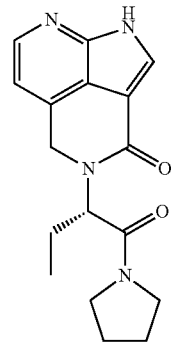 [SMILES: CC[C@@H](C(=O)N1CCCC1)N1Cc2ccnc3[nH]cc(c23)C1=O]

Step A: (S)-1-tert-butyl 3-methyl 4-((1-oxo-1-(pyrrolidin-1-yl)butan-2-ylamino)methyl)-1H-pyrrolo[2,3-b]pyridine-1,3-dicarboxylate

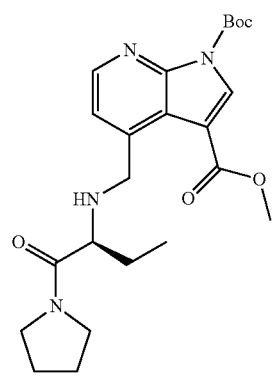 [SMILES: CC[C@H](NCc1ccnc2c1c(C(=O)OC)cn2C(=O)OC(C)(C)C)C(=O)N1CCCC1]

A mixture of sodium triacetoxyborohydride (279 mg, 1.315 mmol) and (S)-2-amino-1-(pyrrolidin-1-yl)butan-1-one (123 mg, 0.789 mmol) in DCE (2 mL) was stirred at room temperature for 30 min. The reaction mixture was cooled to 0° C. A solution of 1-tert-butyl 3-methyl 4-formyl-1H-pyrrolo[2,3-b]pyridine-1,3-dicarboxylate (200 mg, 0.657 mmol) in DCE (2 mL) was added, followed by acetic acid (1 drop). The reaction was stirred at 0° C. for 30 min and then at room temperature for 3 h. Purification by silica column chromatography (EtOAc/DCM, 0-10%) afforded the title compound as a yellow oil (83 mg, 28.4%). [M+H] calc'd for $C_{23}H_{32}N_4O_5$, 445; found, 445.5.

Step B: (S)-4-((1-oxo-1-(pyrrolidin-1-yl)butan-2-ylamino)methyl)-1H-pyrrolo[2,3-b]pyridine-3-carboxylic acid

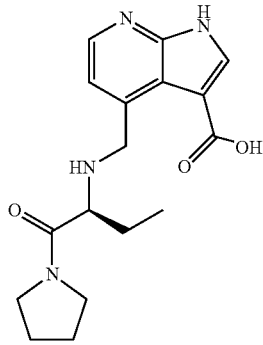 [SMILES: CC[C@H](NCc1ccnc2[nH]cc(C(=O)O)c12)C(=O)N1CCCC1]

To a 20 mL round bottom flask with a stirrer was added (S)-1-tert-butyl 3-methyl 4-((1-oxo-1-(pyrrolidin-1-yl)butan-2-ylamino)methyl)-1H-pyrrolo[2,3-b]pyridine-1,3-dicarboxylate (88 mg, 0.198 mmol), MeOH (1 mL) and THF (1 mL). Aqueous NaOH (12N, 1 mL) was added and the reaction mixture was stirred at 53° C. for 16 h. The solvent was removed and the resulting residue was further purified via preparative mass trigger LC-MS (AcCN/H₂O, 1-50%). The fractions were collected, concentrated, and dried in vacuo to afford the title compound as a yellow oil (6 mg, 9.17%). [M+H] calc'd for $C_{17}H_{22}N_4O_3$, 331; found, 331.6.

Step C: (S)-4-(1-oxo-1-(pyrrolidin-1-yl)butan-2-yl)-4,5-dihydropyrrolo[4,3,2-de][2,6]naphthyridin-3(1H)-one Into a 8 mL scintillation vial equipped for stirring was added (S)-4-((1-oxo-1-(pyrrolidin-1-yl)butan-2-ylamino)methyl)-1H-pyrrolo[2,3-b]pyridine-3-carboxylic acid (6 mg, 0.018 mmol). N,N-dimethylformamide (2 mL), HATU (8.29 mg, 0.022 mmol) and 4-methylmorpholine (2.2 mg, 0.022 mmol) were added and the solution was allowed to stir at room temperature for 1 h. The solvent was removed and the resulting residue was further purified via preparative mass trigger LC-MS (AcCN/H₂O, 5-90%). The fractions were collected, concentrated, and dried in vacuo to afford the title compound as a yellow solid (2.8 mg, 49.4%). ¹H NMR (500 MHz, CD₃OD) δ 0.97 (t, J=7.32 Hz, 3 H) 1.74-1.98 (m, 5 H) 1.98-2.14 (m, 1 H) 3.08-3.22 (m, 1 H) 3.37-3.47 (m, 1 H) 3.65-3.77 (m, 1 H) 4.07 (s, 1 H) 5.05 (s, 2 H) 5.62 (dd, J=8.54, 7.08 Hz, 1 H) 7.11 (d, J=4.88 Hz, 1 H) 7.80 (s, 1 H) 8.29 (br. s., 1 H). [M+H] calc'd for $C_{17}H_{20}N_4O_2$, 313; found, 313.6.

Preparation D:

(R)-2-amino-1-(pyrrolidin-1-yl)butan-1-one

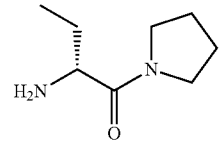

Step A: (R)-tert-butyl 1-oxo-1-(pyrrolidin-1-yl)butan-2-ylcarbamate

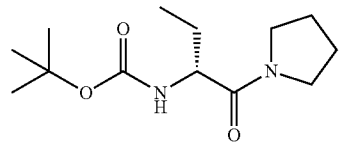 [SMILES: CC[C@@H](NC(=O)OC(C)(C)C)C(=O)N1CCCC1]

To a mixture of (R)-2-(tert-butoxycarbonylamino)butanoic acid (1.5 g, 7.38 mmol), HATU (3.37 g, 8.86 mmol) and pyrrolidine (1.303 mL, 14.76 mmol) in DCM (50 mL) was added Et₃N (2.057 mL, 14.76 mmol). The reaction mixture was stirred at room temperature for 5 h and then washed with saturated aqueous NaHCO₃ and brine. The organics were dried over MgSO₄ and concentrated. Purification by silica column chromatography (MeOH/DCM, 0-10%) afforded the title compound as a light yellow oil (1.6 g, 85%). ¹H NMR (500 MHz, CDCl₃) δ 0.88-1.04 (m, 3 H) 1.38-1.48 (m, 9 H) 1.52-1.64 (m, 1 H) 1.69-1.79 (m, 1 H) 1.82-1.92 (m, 2 H) 1.92-2.02 (m, 2 H) 3.36-3.47 (m, 2 H) 3.53 (dt, J=12.08, 7.14 Hz, 1 H) 3.65 (dt, J=10.01, 6.47 Hz, 1 H) 4.30-4.43 (m, 1 H) 5.37 (d, J=8.30 Hz, 1 H).

Step B: (R)-2-amino-1-(pyrrolidin-1-yl)butan-1-one (R)-tert-butyl 1-oxo-1-(pyrrolidin-1-yl)butan-2-ylcarbamate (1.6 g, 6.24 mmol) was stirred in 50% TFA/DCM (10 mL) for 1 h. The reaction mixture was concentrated and isolated as a clear oil, TFA salt. Purification by silica column chromatography (MeOH/DCM, 0-10%) afforded the title compound as a white solid (free base, 0.91 g, 5.82 mmol, 79%). ¹H NMR (400 MHz, CDCl₃) δ 1.03 (t, J=7.45 Hz, 3 H) 1.78-2.03 (m, 6 H) 3.29-3.46 (m, 2 H) 3.46-3.54 (m, 1 H) 3.54-3.66 (m, 1 H) 4.14 (t, J=6.19 Hz, 1 H).

Example 19

(R)-4-(1-oxo-1-(pyrrolidin-1-yl)butan-2-yl)-4,5-dihydropyrrolo[4,3,2-de][2,6]naphthyridin-3(1H)-one

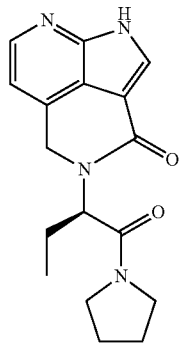 [SMILES: CC[C@H](C(=O)N1CCCC1)N1Cc2ccnc3[nH]cc(c23)C1=O]

Step A: (R)-1-tert-butyl 3-methyl 4-((1-oxo-1-(pyrrolidin-1-yl)butan-2-ylamino)methyl)-1H-pyrrolo[2,3-b]pyridine-1,3-dicarboxylate

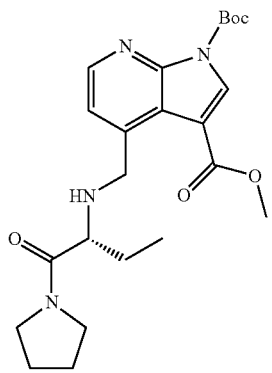 [SMILES: CC[C@@H](NCc1ccnc2c1c(C(=O)OC)cn2C(=O)OC(C)(C)C)C(=O)N1CCCC1]

A mixture of sodium triacetoxyborohydride (237 mg, 1.116 mmol) and (R)-2-amino-1-(pyrrolidin-1-yl)butan-1-one (131 mg, 0.837 mmol) in DCE (2 mL) was stirred at room temperature for 30 min. The reaction mixture was cooled to 0° C. A solution of 1-tert-butyl 3-methyl 4-formyl-1H-pyrrolo[2,3-b]pyridine-1,3-dicarboxylate (200 mg, 0.657 mmol) in DCE (2 mL) was added, followed by acetic acid (1 drop). The reaction was stirred at 0° C. for 30 min and then at room temperature for 3 h. Purification by silica column chromatography (EtOAc/DCM, 0-10%) afforded the title compound as a yellow oil (260 mg, 93%). [M+H] calc'd for $C_{23}H_{32}N_4O_5$, 445; found, 445.5.

Step B: (R)-4-((1-oxo-1-(pyrrolidin-1-yl)butan-2-ylamino)methyl)-1H-pyrrolo[2,3-b]pyridine-3-carboxylic acid

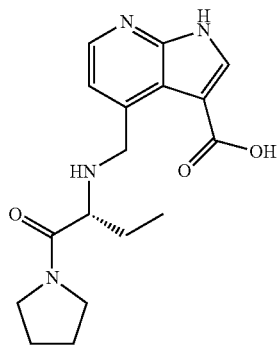 [SMILES: CC[C@@H](NCc1ccnc2[nH]cc(C(=O)O)c12)C(=O)N1CCCC1]

To a 20 mL round bottom flask with a stirrer was added (R)-1-tert-butyl 3-methyl 4-((1-oxo-1-(pyrrolidin-1-yl)butan-2-ylamino)methyl)-1H-pyrrolo[2,3-b]pyridine-1,3-dicarboxylate (150 mg, 0.337 mmol), MeOH (1 mL) and THF (1 mL). Aqueous NaOH (12 N, 1 mL) was added and the reaction mixture was stirred at 53° C. for 16 h. The solvent was removed and the resulting residue was further purified via preparative mass trigger LC-MS (AcCN/H$_2$O, 5-50%). The fractions were collected, concentrated, and dried in vacuo to afford the title compound as a yellow oil (8.7 mg, 0.026 mmol, 7.80%). [M+H] calc'd for $C_{17}H_{22}N_4O_3$, 331; found, 331.6.

Step C: (R)-4-(1-oxo-1-(pyrrolidin-1-yl)butan-2-yl)-4,5-dihydropyrrolo[4,3,2-de][2,6]naphthyridin-3(1H)-one To an 8 mL scintillation vial equipped for stirring was added (S)-4-((1-oxo-1-(pyrrolidin-1-yl)butan-2-ylamino)methyl)-1H-pyrrolo[2,3-b]pyridine-3-carboxylic acid (8.7 mg, 0.026 mmol). N,N-dimethylformamide (2 mL), HATU (12.02 mg, 0.032 mmol) and 4-methylmorpholine (3.20 mg, 0.022 mmol) were added and the solution was allowed to stir at room temperature for 1 h. The solvent was removed and the resulting residue was further purified via preparative mass trigger LC-MS (AcCN/H$_2$O, 5-90%). The fractions were collected, concentrated, and dried in vacuo to afford the title compound as a yellow solid (1.6 mg, 19.5%). $^1$H NMR (500 MHz, CD$_3$OD) δ 0.88-1.04 (m, 3 H) 1.75-1.98 (m, 4 H) 1.98-2.05 (m, 2 H) 3.43-3.50 (m, 3 H) 3.50-3.57 (m, 1 H) 5.07 (s, 2H) 5.62 (dd, J=8.79, 6.83 Hz, 1 H) 7.13 (d, J=4.88 Hz, 1 H) 7.81 (s, 1 H) 8.28 (d, J=5.37 Hz, 1 H). [M+H] calc'd for $C_{17}H_{20}N_4O_2$, 313; found, 313.6.

Preparation E:

(R)-2-amino-3-methyl-1-(pyrrolidin-1-yl)butan-1-one

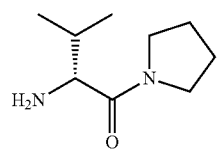

STEP A: (R)-tert-butyl 3-methyl-1-oxo-1-(pyrrolidin-1-yl)butan-2-ylcarbamate

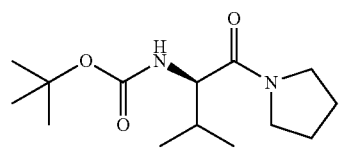 [SMILES: CC(C)[C@@H](NC(=O)OC(C)(C)C)C(=O)N1CCCC1]

To a mixture of (R)-2-(tert-butoxycarbonylamino)-3-methylbutanoic acid (1.0 g, 4.60 mmol), HATU (2.1 g, 5.52 mmol) and pyrrolidine (0.812 mL, 9.21 mmol) in DCM (30 mL) was added Et$_3$N (1.28 mL, 9.21 mmol). The reaction mixture was stirred at room temperature for 5 h and then washed with saturated aqueous NaHCO$_3$ and brine. The organics were dried over MgSO$_4$ and concentrated. Purification by silica column chromatography (MeOH/DCM, 0-10%) afforded the title compound as a light yellow oil (1.18 g, 95%). $^1$H NMR (400 MHz, CDCl$_3$) δ 0.95 (d, J=18.95 Hz, 3 H) 0.95 (d, J=5.31 Hz, 3 H) 1.30-1.53 (m, 9 H) 1.77-2.07 (m, 5 H) 3.33-3.59 (m, 3 H) 3.59-3.80 (m, 1 H) 4.25 (dd, J=9.35, 6.57 Hz, 1 H) 5.30 (d, J=9.09 Hz, 1 H).

Step B: (R)-2-amino-3-methyl-1-(pyrrolidin-1-yl)butan-1-one (R)-tert-butyl 1-oxo-1-(pyrrolidin-1-yl)butan-2-ylcarbamate (1.18 g, 4.37 mmol) was stirred in 50% TFA/DCM (10 mL) for 1 h. The reaction mixture was concentrated and isolated as a clear oil, TFA salt. Purification by flash column chromatography (MeOH/DCM, 0-10%) afforded the title compound as a white solid (free base, 0.69 g, 92%). $^1$H NMR (400 MHz, CDCl$_3$) δ 1.08 (d, J=7.07 Hz, 3 H) 1.06 (d, J=7.07 Hz, 3 H) 1.77-2.04 (m, 4 H) 2.12-2.26 (m, 1 H) 3.26-3.45 (m, 2 H) 3.45-3.58 (m, 1H) 3.63 (dt, J=9.98, 6.51 Hz, 1 H) 4.01 (d, J=5.56 Hz, 1 H).

Example 20

(R)-4-(3-methyl-1-oxo-1-(pyrrolidin-1-yl)butan-2-yl)-4,5-dihydropyrrolo[4,3,2-de][2,6]naphthyridin-3(1H)-one

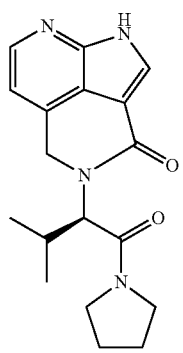 [SMILES: CC(C)[C@H](C(=O)N1CCCC1)N1Cc2ccnc3[nH]cc(c23)C1=O]

Step A: (R)-1-tert-butyl 3-methyl 4-((3-methyl-1-oxo-1-(pyrrolidin-1-yl)butan-2-ylamino)methyl)-1H-pyrrolo[2,3-b]pyridine-1,3-dicarboxylate

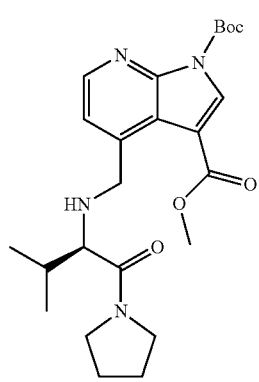 [SMILES: COC(=O)c1cn(C(=O)OC(C)(C)C)c2nccc(CN[C@@H](C(=O)N3CCCC3)C(C)C)c12]

A mixture of sodium triacetoxyborohydride (139 mg, 0.657 mmol) and (R)-2-amino-3-methyl-1-(pyrrolidin-1-yl)butan-1-one (84 mg, 0.493 mmol) in DCE (2 mL) was stirred at room temperature for 30 min. The reaction mixture was cooled to 0° C. A solution of 1-tert-butyl 3-methyl 4-formyl-1H-pyrrolo[2,3-b]pyridine-1,3-dicarboxylate (100 mg, 0.329 mmol) in DCE (2 mL) was added, followed by acetic acid (1 drop). The reaction was stirred at 0° C. for 30 min and then at room temperature for 3 h. Purification by silica column chromatography (EtOAc/DCM, 0-10%) afforded the title compound as a yellow oil (128 mg, 85%). [M+H] calc'd for C$_{24}$H$_{34}$N$_4$O$_5$, 459; found, 459.6.

Step B: (R)-4-((3-methyl-1-oxo-1-(pyrrolidin-1-yl)butan-2-ylamino)methyl)-1H-pyrrolo[2,3-b]pyridine-3-carboxylic acid

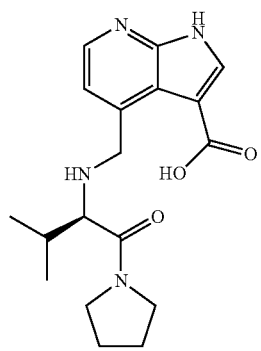 [SMILES: CC(C)[C@@H](NCc1ccnc2[nH]cc(C(=O)O)c12)C(=O)N1CCCC1]

To an 8 mL scintillation vial equipped for stirring was added (R)-1-tert-butyl 3-methyl 4-((3-methyl-1-oxo-1-(pyrrolidin-1-yl)butan-2-ylamino)methyl)-1H-pyrrolo[2,3-b]pyridine-1,3-dicarboxylate (134 mg, 0.292 mmol). Aqueous NaOH (12N, 2 mL) and MeOH (1 mL) were added and the solution was stirred at 53° C. for 48 h. The reaction mixture was purified via preparative mass trigger LC-MS (AcCN/H$_2$O, 5-90%). The fractions were collected, concentrated, and dried in vacuo to afford the title compound as a yellow oil.

Step C: (R)-4-(3-methyl-1-oxo-1-(pyrrolidin-1-yl)butan-2-yl)-4,5-dihydropyrrolo[4,3,2-de][2,6]naphthyridin-3(1H)-one In a manner similar to Step C of Example 19, (R)-4-((3-methyl-1-oxo-1-(pyrrolidin-1-yl)butan-2-ylamino)methyl)-1H-pyrrolo[2,3-b]pyridine-3-carboxylic acid was cyclized in a mixture of THF (2 mL), HATU (133 mg, 0.351 mmol) and 4-methylmorpholine (35.5 mg, 0.351 mmol) and the resulting product was purified via preparative mass trigger LC-MS (AcCN/H$_2$O, 1-50%). The fractions were collected, concentrated, and dried in vacuo to afford the title compound as a yellow oil (28 mg, 29.4% from Step B starting material). $^1$H NMR (400 MHz, CD$_3$OD) δ 0.92 (d, J=6.57 Hz, 3 H) 1.04 (d, J=6.32 Hz, 3 H) 1.78-1.94 (m, 3 H) 1.94-2.02 (m, 1 H) 2.02 (s, 1 H) 2.45-2.65 (m, 1 H) 3.38-3.56 (m, 2 H) 3.61-3.79 (m, 2 H) 5.04-5.15 (m, 1 H) 5.45 (d, J=11.12 Hz, 1 H) 7.30 (d, J=5.56 Hz, 1 H) 7.91 (s, 1 H) 8.35 (d, J=5.56 Hz, 1 H). [M+H] calc'd for C$_{18}$H$_{22}$N$_4$O$_2$, 327; found, 327.6.

Preparation F:

(R)-2-amino-4-methyl-1-(pyrrolidin-1-yl)pentan-1-one

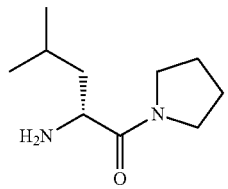

Step A: (R)-tert-butyl 4-methyl-1-oxo-1-(pyrrolidin-1-yl)pentan-2-ylcarbamate

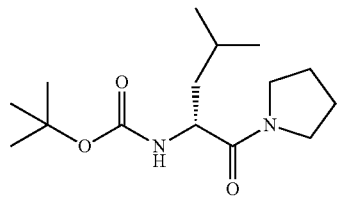 [SMILES: CC(C)C[C@@H](NC(=O)OC(C)(C)C)C(=O)N1CCCC1]

To a mixture of (R)-2-(tert-butoxycarbonylamino)-4-methylpentanoic acid (1.0 g, 4.32 mmol), HATU (1.97 g, 5.19 mmol) and pyrrolidine (0.76 mL, 8.65 mmol) in DCM (30 mL) was added Et$_3$N (1.2 mL, 8.65 mmol). The reaction mixture was stirred at room temperature for 5 h and then washed with saturated aqueous NaHCO$_3$ and brine. The organics were dried over MgSO$_4$ and concentrated. Purification by silica column chromatography (MeOH/DCM, 0-10%) afforded the title compound as a light yellow oil (1.17 g, 95%).

Step B: (R)-2-amino-4-methyl-1-(pyrrolidin-1-yl)pentan-1-one (R)-tert-Butyl 4-methyl-1-oxo-1-(pyrrolidin-1-yl)pentan-2-ylcarbamate was stirred in 50% TFA/DCM (10 mL) for 1 h. The reaction mixture was concentrated and isolated as clear oil, TFA salt. Purification by flash column chromatography (MeOH/DCM, 0-10%) afforded the title compound as a white solid (free base, 0.71 g, 93%). $^1$H NMR (400 MHz, CDCl$_3$) δ 0.96 (t, J=6.57 Hz, 6 H) 1.42-1.60 (m, 1 H) 1.75-2.04 (m, 6 H) 3.26-3.44 (m, 2 H) 3.45-3.56 (m, 1 H) 3.61 (dt, J=9.85, 6.57 Hz, 1 H) 4.15 (dd, J=8.84, 4.29 Hz, 1 H).

Example 21

(R)-4-(4-methyl-1-oxo-1-(pyrrolidin-1-yl)pentan-2-yl)-4,5-dihydropyrrolo[4,3,2-de][2,6]naphthyridin-3(1H)-one

Step A: (R)-1-tert-butyl 3-methyl 4-((4-methyl-1-oxo-1-(pyrrolidin-1-yl)pentan-2-ylamino)methyl)-1H-pyrrolo[2,3-b]pyridine-1,3-dicarboxylate

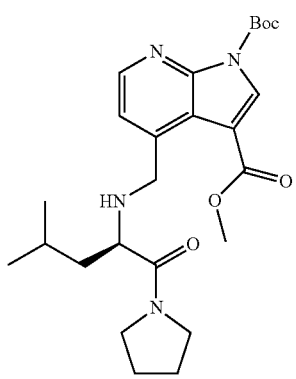 [SMILES: COC(=O)c1cn(C(=O)OC(C)(C)C)c2nccc(CN[C@H](CC(C)C)C(=O)N3CCCC3)c12]

A mixture of sodium triacetoxyborohydride (139 mg, 0.657 mmol) and (R)-2-amino-4-methyl-1-(pyrrolidin-1-yl)pentan-1-one (91 mg, 0.493 mmol) in DCE (2 mL) was stirred at room temperature for 30 min. The reaction mixture was cooled to 0° C. A solution of 1-tert-butyl 3-methyl 4-formyl-1H-pyrrolo[2,3-b]pyridine-1,3-dicarboxylate (100 mg, 0.329 mmol) in DCE (2 mL) was added, followed by acetic acid (1 drop). The reaction was stirred at 0° C. for 30 min and then at room temperature for 3 h. Purification by silica column chromatography (EtOAc/DCM, 0-10%) afforded the title compound as a yellow oil (160 mg, 93%). [M+H] calc'd for C$_{25}$H$_{36}$N$_4$O$_5$, 473; found, 473.7.

Step B: (R)-4-((4-methyl-1-oxo-1-(pyrrolidin-1-yl)pentan-2-ylamino)methyl)-1H-pyrrolo[2,3-b]pyridine-3-carboxylic acid

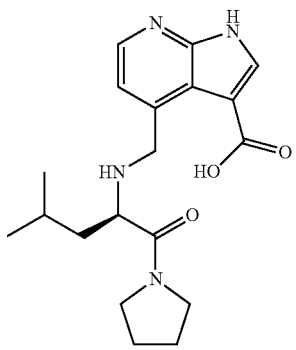 [SMILES: CC(C)C[C@@H](NCc1ccnc2[nH]cc(C(=O)O)c12)C(=O)N1CCCC1]

To an 8 mL scintillation vial equipped for stirring was added (R)-1-tert-butyl 3-methyl 4-((4-methyl-1-oxo-1-(pyrrolidin-1-yl)pentan-2-ylamino)methyl)-1H-pyrrolo[2,3-b]pyridine-1,3-dicarboxylate (160 mg, 0.339 mmol) under nitrogen. Aqueous NaOH (12N, 2 mL) and MeOH (1 mL) were added and the solution was stirred at 53° C. for 48 h. The reaction mixture was purified via preparative mass trigger LC-MS (AcCN/H$_2$O, 5-90%). The fractions were collected, concentrated, and dried in vacuo to afford the title compound as yellow oil.

Step C: (R)-4-(4-methyl-1-oxo-1-(pyrrolidin-1-yl)pentan-2-yl)-4,5-dihydropyrrolo[4,3,2-de][2,6]naphthyridin-3(1H)-one In a manner similar to Step C of Example 19, (R)-4-((4-methyl-1-oxo-1-(pyrrolidin-1-yl)pentan-2-ylamino)methyl)-1H-pyrrolo[2,3-b]pyridine-3-carboxylic acid was cyclized in a mixture of THF (2 mL), HATU (133 mg, 0.351 mmol) and 4-methylmorpholine (35.5 mg, 0.351 mmol) and the resulting product was purified via preparative mass trigger LC-MS (AcCN/H$_2$O, 1-50%). The fractions were collected, concentrated and dried in vacuo to afford the title compound as a yellow oil (53 mg, 46% from Step B starting material). $^1$H NMR (400 MHz, CDCl$_3$) δ 0.96 (t, J=6.57 Hz, 6 H) 1.42-1.60 (m, 1 H) 1.75-2.04 (m, 6 H) 3.26-3.44 (m, 2 H) 3.45-3.56 (m, 1 H) 3.61 (dt, J=9.85, 6.57 Hz, 1 H) 4.15 (dd, J=8.84, 4.29 Hz, 1 H). [M+H] calc'd for C$_{19}$H$_{24}$N$_4$O$_2$, 341; found, 341.6.

Preparation G:

(R)-2-amino-N-cyclopentyl-3-methylbutanamide

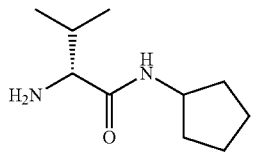

Step A: (R)-tert-butyl 1-(cyclopentylamino)-3-methyl-1-oxobutan-2-ylcarbamate

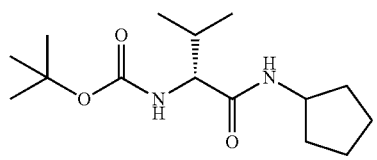 [SMILES: CC(C)[C@@H](NC(=O)OC(C)(C)C)C(=O)NC1CCCC1]

To a mixture of (R)-2-(tert-butoxycarbonylamino)-3-methylbutanoic acid (0.5 g, 2.301 mmol), HATU (1.05 g, 2.76 mmol) and cyclopentanamine (0.455 mL, 4.60 mmol) in DCM (20 mL) was added Et$_3$N (0.642 mL, 4.60 mmol). The reaction mixture was stirred at room temperature for 5 h, washed with saturated aqueous NaHCO$_3$ and brine, dried over MgSO$_4$, and concentrated. Purification by silica column chromatography (MeOH/DCM, 0-10%) afforded the title compound (0.61 g, 94%).

Step B:
(R)-2-amino-N-cyclopentyl-3-methylbutanamide (R)-tert-Butyl 1-(cyclopentylamino)-3-methyl-1-oxobutan-2-ylcarbamate was stirred in 50% TFA/DCM (10 mL) for 1 h. The reaction mixture was concentrated and isolated as a clear oil, TFA salt. Purification by flash column chromatography (MeOH/DCM, 0-10%) afforded the title compound as a white solid (free base, 0.37 g, 92%). $^1$H NMR (400 MHz, CDCl$_3$) δ 0.96-1.08 (m, 6 H) 1.35-1.51 (m, 1 H) 1.51-1.74 (m, 4 H) 1.90 (td, J=12.82, 6.19 Hz, 3 H) 2.08-2.23 (m, 1 H) 3.82 (d, J=6.82 Hz, 1 H) 4.02-4.21 (m, 1 H) 7.32-7.53 (m, 0 H) 7.40 (d, J=7.07 Hz, 1 H).

Example 22

(R)—N-cyclopentyl-3-methyl-2-(3-oxopyrrolo[4,3,2-de][2,6]naphthyridin-4(1H,3H,5H)-yl)butanamide

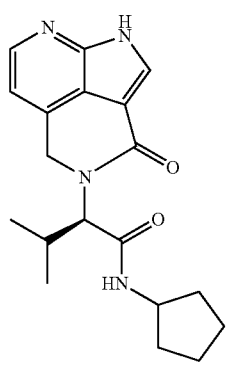 [SMILES: CC(C)[C@H](C(=O)NC1CCCC1)N1Cc2ccnc3[nH]cc(c23)C1=O]

Step A: (R)-1-tert-butyl 3-methyl 4-((1-(cyclopentylamino)-3-methyl-1-oxobutan-2-ylamino)methyl)-1H-pyrrolo[2,3-b]pyridine-1,3-dicarboxylate

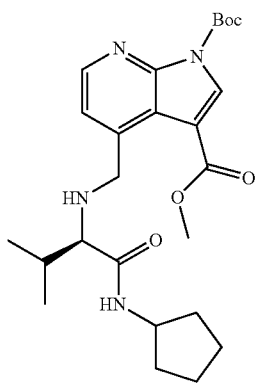 [SMILES: COC(=O)c1cn(C(=O)OC(C)(C)C)c2nccc(CN[C@@H](C(=O)NC3CCCC3)C(C)C)c12]

A mixture of sodium triacetoxyborohydride (104 mg, 0.493 mmol) and (R)-2-amino-N-cyclopentyl-3-methylbutanamide (68.1 mg, 0.370 mmol) in DCE (2 mL) was stirred at room temperature for 30 min. The reaction mixture was cooled to 0° C. A solution of 1-tert-butyl 3-methyl 4-formyl-1H-pyrrolo[2,3-b]pyridine-1,3-dicarboxylate (75 mg, 0.246 mmol) in DCE (2 mL) was added, followed by acetic acid (1 drop). The reaction mixture was stirred at 0° C. for 30 min and then at room temperature for 3 h. Purification by silica column chromatography (EtOAc/DCM, 0-10%) afforded the title compound as a yellow oil (105 mg, 90%). [M+H] calc'd for C$_{25}$H$_{36}$N$_4$O$_5$, 473; found, 473.7.

Step B: (R)-4-((1-(cyclopentylamino)-3-methyl-1-oxobutan-2-ylamino)methyl)-1H-pyrrolo[2,3-b]pyridine-3-carboxylic acid

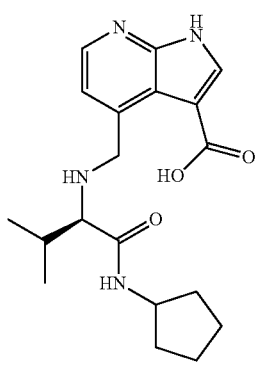 [SMILES: CC(C)[C@@H](NCc1ccnc2[nH]cc(C(=O)O)c12)C(=O)NC1CCCC1]

To an 8 mL scintillation vial equipped for stirring was added (R)-1-tert-butyl 3-methyl 4-((1-(cyclopentylamino)-3-methyl-1-oxobutan-2-ylamino)methyl)-1H-pyrrolo[2,3-b]pyridine-1,3-dicarboxylate (105 mg, 0.222 mmol) under nitrogen. Aqueous NaOH (12N, 2 mL) and MeOH (1 mL) were added and the solution was stirred at 53° C. for 48 h. The reaction mixture was purified via preparative mass trigger LC-MS (AcCN/H$_2$O, 5-90%). The fractions were collected, concentrated, and dried in vacuo to afford the title compound as yellow oil.

Step C: (R)—N-cyclopentyl-3-methyl-2-(3-oxopyrrolo[4,3,2-de][2,6]naphthyridin-4(1H,3H,5H)-yl)butanamide In a manner similar to Step C of Example 19, (R)-4-((1-(cyclopentylamino)-3-methyl-1-oxobutan-2-ylamino)methyl)-1H-pyrrolo[2,3-b]pyridine-3-carboxylic acid was cyclized in a mixture of THF (2 mL), HATU (101 mg, 0.267 mmol) and 4-methylmorpholine (27.0 mg, 0.267 mmol) and the resulting product was purified via preparative mass trigger LC-MS (AcCN/H$_2$O, 1-50%). The fractions were collected, concentrated and dried in vacuo to afford the title compound as a yellow oil (23 mg, 30% from Step B starting material). $^1$H NMR (400 MHz, CD$_3$OD) δ 0.99-1.04 (m, 3 H) 1.04-1.08 (m, 3 H) 1.28-1.38 (m, 1 H) 1.42-1.67 (m, 4 H) 1.72 (br. s., 2 H) 1.77-2.00 (m, 2 H) 2.79-2.90 (m, 1 H) 4.02-4.21 (m, 2 H) 5.12 (d, J=9.35 Hz, 1 H) 7.78 (d, J=5.31 Hz, 1 H) 7.93-8.08 (m, 1 H) 8.63 (d, J=5.30 Hz, 1 H). [M+H] calc'd for C$_{19}$H$_{24}$N$_4$O$_2$, 341; found, 341.4.

Preparation H:

(2R,3R)-2-amino-N-cyclopentyl-3-methylpentanamide

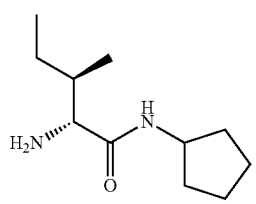

Step A: tert-butyl (2R,3R)-1-(cyclopentylamino)-3-methyl-1-oxopentan-2-ylcarbamate

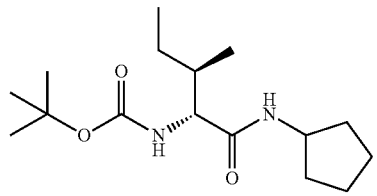 [SMILES: CC[C@@H](C)[C@@H](NC(=O)OC(C)(C)C)C(=O)NC1CCCC1]

To a mixture of (2R,3R)-2-(tert-butoxycarbonylamino)-3-methylpentanoic acid (0.5 g, 2.162 mmol, HATU (0.986 g, 2.59 mmol) and cyclopentanamine (0.427 mL, 4.32 mmol) in DCM (10 mL) was added Et$_3$N (0.603 mL, 4.32 mmol). The reaction mixture was stirred at room temperature for 5 h and then washed with saturated aqueous NaHCO$_3$ and brine. The organics were dried over MgSO$_4$ and concentrated. Purification by silica column chromatography (MeOH/DCM, 0-10%) afforded the title compound (0.56 g, 87%). $^1$H NMR (400 MHz, CDCl$_3$) δ 0.82-0.89 (m, 3 H) 0.92 (t, J=7.45 Hz, 3 H) 1.32-1.41 (m, 6 H) 1.44 (s, 9 H) 1.55-1.77 (m, 3 H) 1.84-2.04 (m, 2 H) 2.99 (d, J=4.29 Hz, 1 H) 3.96 (dd, J=8.72, 5.43 Hz, 1 H) 4.21 (dt, J=13.89, 6.95 Hz, 1 H) 5.02 (br. s., 1 H) 5.93 (br. s., 1 H).

Step B: (2R,3R)-2-amino-N-cyclopentyl-3-methylpentanamide

A mixture of tert-butyl (2R,3R)-1-(cyclopentylamino)-3-methyl-1-oxopentan-2-ylcarbamate and 50% TFA/DCM (10 mL) was stirred for 1 h. The reaction mixture was concentrated and isolated as a clear oil, TFA salt. Purification by flash column chromatography (MeOH/DCM, 0-10%) afforded the title compound as a white solid (free base, 0.34 g, 90%). Pure product by TLC (visualized by ninhydrin stain).

Example 23

(2R,3R)—N-cyclopentyl-3-methyl-2-(3-oxopyrrolo[4,3,2-de][2,6]naphthyridin-4(1H,3H,5H)-yl)pentanamide

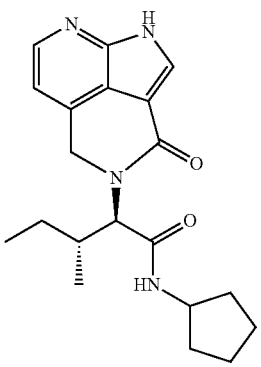 [SMILES: CC[C@@H](C)[C@H](C(=O)NC1CCCC1)N1Cc2ccnc3[nH]cc(c23)C1=O]

Step A: 1-tert-butyl 3-methyl 4-(((2R,3R)-1-(cyclopentylamino)-3-methyl-1-oxopentan-2-ylamino)methyl)-1H-pyrrolo[2,3-b]pyridine-1,3-dicarboxylate

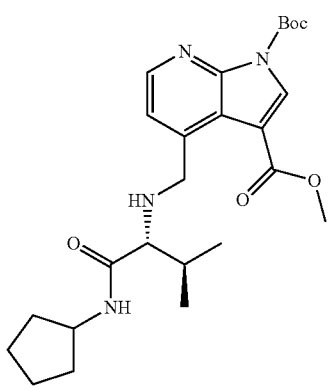

A mixture of sodium triacetoxyborohydride (104 mg, 0.493 mmol) and (2R,3R)-2-amino-N-cyclopentyl-3-methylpentanamide (48.9 mg, 0.246 mmol) in DCE (2 mL) was stirred at room temperature for 30 min. To this mixture was added 1-tert-butyl 3-methyl 4-formyl-1H-pyrrolo[2,3-b]pyridine-1,3-dicarboxylate (75 mg, 0.246 mmol). The reaction mixture was stirred at room temperature for 1 h and was subsequently concentrated to afford the title compound as a crude intermediate. [M+H] calc'd for $C_{26}H_{38}N_4O_5$, 487; found, 487.7.

Step B: 4-(((2R,3R)-1-(cyclopentylamino)-3-methyl-1-oxopentan-2-ylamino)methyl)-1H-pyrrolo[2,3-b]pyridine-3-carboxylic acid

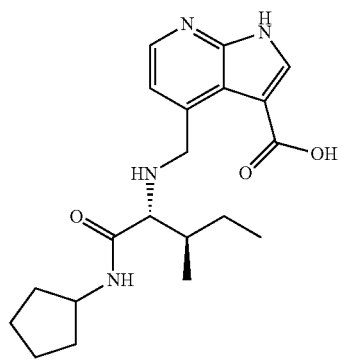 [SMILES: CC[C@@H](C)[C@@H](NCc1ccnc2[nH]cc(C(=O)O)c12)C(=O)NC1CCCC1]

To crude 1-tert-butyl 3-methyl 4-(((2R,3R)-1-(cyclopentylamino)-3-methyl-1-oxopentan-2-ylamino)methyl)-1H-pyrrolo[2,3-b]pyridine-1,3-dicarboxylate was added MeOH (1 mL) and aqueous NaOH (12N, 2 mL). The reaction mixture was stirred at 53° C. for 16 h and then purified via preparative mass trigger LC-MS (AcCN/H₂O, 5-90%). The fractions were collected, concentrated, and dried in vacuo to afford the title compound. [M+H] calc'd for $C_{20}H_{28}N_4O_3$, 373; found, 373.7.

Step C: (2R,3R)—N-cyclopentyl-3-methyl-2-(3-oxopyrrolo[4,3,2-de][2,6]naphthyridin-4(1H,3H,5H)-yl)pentanamide In a manner similar to Step C of Example 19, 4-(((2R,3R)-1-(cyclopentylamino)-3-methyl-1-oxopentan-2-ylamino) methyl)-1H-pyrrolo[2,3-b]pyridine-3-carboxylic acid was cyclized in a mixture of THF (2 mL), HATU (112 mg, 0.296 mmol) and 4-methylmorpholine (37.4 mg, 0.370 mmol) and the resulting product was purified via preparative mass trigger LC-MS (AcCN/H₂O, 5-50%). The fractions were collected, concentrated, and dried in vacuo to afford the title compound as a yellow oil (32 mg, 37% from Step A starting material). ¹H NMR (400 MHz, CD₃OD) δ 0.61-0.72 (m, 2 H) 0.90-1.06 (m, 5 H) 1.37-1.66 (m, 7 H) 1.66-1.77 (m, 2 H) 1.77-1.99 (m, 4 H) 3.98-4.22 (m, 1 H) 4.85-4.97 (m, 2 H) 5.21 (d, J=9.35 Hz, 1 H). [M+H] calc'd for $C_{20}H_{26}N_4O_2$, 355; found, 355.5.

Example 24

(2R,3S)—N-cyclopentyl-3-methyl-2-(3-oxopyrrolo[4,3,2-de][2,6]naphthyridin-4(1H,3H,5H)-yl)pentanamide

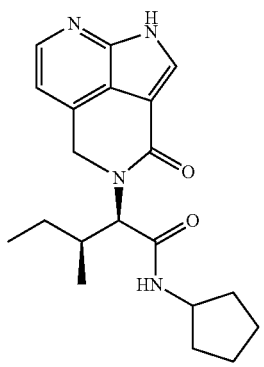 [SMILES: CC[C@H](C)[C@H](C(=O)NC1CCCC1)N1Cc2ccnc3[nH]cc(c23)C1=O]

Step A: (2R,3S)-2-((1-(tert-butoxycarbonyl)-3-(methoxycarbonyl)-1H-pyrrolo[2,3-b]pyridin-4-yl)methylamino)-3-methylpentanoic acid

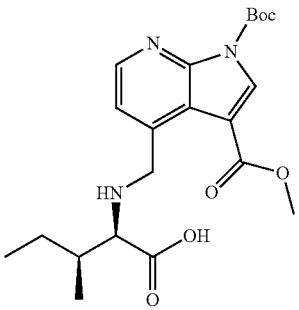 [SMILES: CC[C@H](C)[C@@H](NCc1ccnc2c1c(C(=O)OC)cn2C(=O)OC(C)(C)C)C(=O)O]

To a 10 mL round bottom flask was added sodium triacetoxyborohydride (104 mg, 0.493 mmol), (2R,3S)-2-amino-3-methylpentanoic acid (43.1 mg, 0.329 mmol), and DCM (2 mL). The mixture was stirred at room temperature for 30 min, after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture concentrated to afford the title compound, which was used in the next step without further purification. [M+H] calc'd for $C_{21}H_{29}N_3O_6$, 420; found, 420.6.

Step B: 1-tert-butyl 3-methyl 4-(((2R,3S)-1-(cyclopentylamino)-3-methyl-1-oxopentan-2-ylamino)methyl)-1H-pyrrolo[2,3-b]pyridine-1,3-dicarboxylate

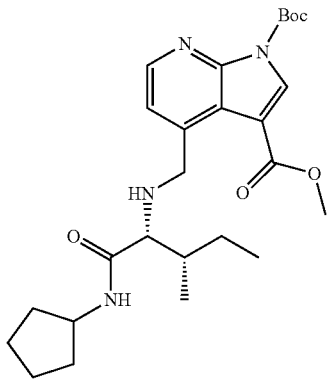 [SMILES: CC[C@H](C)[C@@H](NCc1ccnc2c1c(C(=O)OC)cn2C(=O)OC(C)(C)C)C(=O)NC1CCCC1]

To (2R,3S)-2-((1-(tert-butoxycarbonyl)-3-(methoxycarbonyl)-1H-pyrrolo[2,3-b]pyridin-4-yl)methylamino)-3-methylpentanoic acid was added THF (2 mL), followed by HATU (94 mg, 0.246 mmol), cyclopentanamine (70.0 mg, 0.822 mmol) and 4-methylmorpholine (83 mg, 0.822 mmol). The suspension was stirred at 43° C. for 36 h to afford the title compound, which was used in the next step without further purification. [M+H] calc'd for $C_{26}H_{38}N_4O_5$, 487; found, 487.7.

Step C: 4-(((2R,3S)-1-(cyclopentylamino)-3-methyl-1-oxopentan-2-ylamino)methyl)-1H-pyrrolo[2,3-b]pyridine-3-carboxylic acid

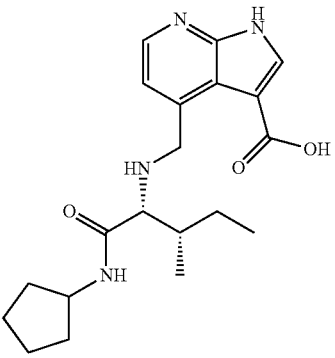 [SMILES: CC[C@H](C)[C@@H](NCc1ccnc2[nH]cc(C(=O)O)c12)C(=O)NC1CCCC1]

Crude 1-tert-butyl 3-methyl 4-(((2R,3S)-1-(cyclopentylamino)-3-methyl-1-oxopentan-2-ylamino)methyl)-1H-pyrrolo[2,3-b]pyridine-1,3-dicarboxylate was concentrated and re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for C$_{20}$H$_{28}$N$_4$O$_3$, 373; found, 373.7.

Step D: (2R,3S)—N-cyclopentyl-3-methyl-2-(3-oxopyrrolo[4,3,2-de][2,6]naphthyridin-4(1H,3H,5H)-yl)pentanamide In a manner similar to Step C of Example 19, 4-(((2R,3S)-1-(cyclopentylamino)-3-methyl-1-oxopentan-2-ylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol) and the resulting product was purified via preparative mass trigger LC-MS (AcCN/H$_2$O, 5-50%). The fractions were collected, concentrated, and dried in vacuo to afford the title compound as a yellow oil (6 mg, 10% from Step A starting material). $^1$H NMR (500 MHz, CD$_3$OD) δ 0.89 (d, J=6.35 Hz, 3 H) 0.95-1.06 (m, 3 H) 1.15-1.26 (m, 1 H) 1.35-1.45 (m, 1 H) 1.45-1.63 (m, 4 H) 1.70 (br. s., 1 H) 1.81-2.02 (m, 2 H) 2.10-2.19 (m, 1 H) 2.28 (br. s., 1 H) 3.34 (s, 1 H) 4.02-4.16 (m, 1 H) 5.04-5.18 (m, 1 H) 5.40-5.56 (m, 1 H) 7.29 (d, J=5.37 Hz, 1 H) 7.90 (s, 1 H) 8.34 (d, J=5.37 Hz, 1 H). [M+H] calc'd for C$_{20}$H$_{26}$N$_4$O$_2$, 355; found, 355.5.

Example 25

(R)—N-cyclopentyl-2-cyclopropyl-2-(3-oxopyrrolo[4,3,2-de][2,6]naphthyridin-4(1H,3H,5H)-yl)acetamide

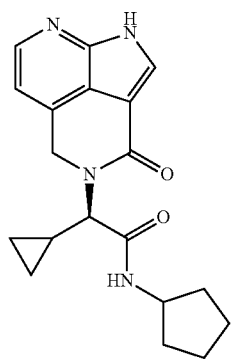 [SMILES: O=C(NC1CCCC1)[C@@H](C1CC1)N1Cc2ccnc3[nH]cc(c23)C1=O]

Step A: (R)-2-((1-(tert-butoxycarbonyl)-3-(methoxycarbonyl)-1H-pyrrolo[2,3-b]pyridin-4-yl)methylamino)-2-cyclopropylacetic acid

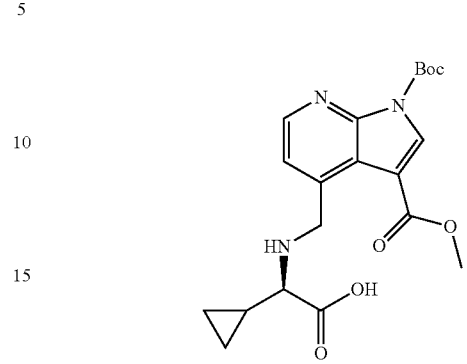

To a 10 mL round bottom flask was added sodium triacetoxyborohydride (104 mg, 0.493 mmol), (R)-2-amino-2-cyclopropylacetic acid (37.8 mg, 0.329 mmol), and DCM (2 mL). The reaction mixture was stirred at room temperature in for 30 min, after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture was concentrated to afford the title compound, which was used in the next step without further purification. [M+H] calc'd for C$_{20}$H$_{25}$N$_3$O$_6$, 404; found, 404.3.

Step B: (R)-1-tert-butyl 3-methyl 4-((2-(cyclopentylamino)-1-cyclopropyl-2-oxoethylamino)methyl)-1H-pyrrolo[2,3-b]pyridine-1,3-dicarboxylate

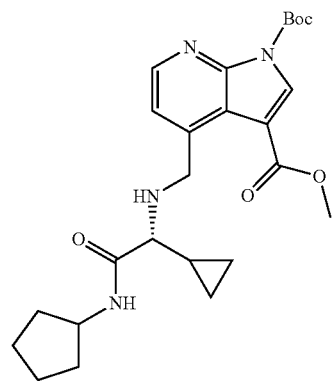 [SMILES: COC(=O)c1cn(C(=O)OC(C)(C)C)c2nccc(CN[C@@H](C(=O)NC3CCCC3)C3CC3)c12]

To (R)-2-((1-(tert-butoxycarbonyl)-3-(methoxycarbonyl)-1H-pyrrolo[2,3-b]pyridin-4-yl)methylamino)-2-cyclopropylacetic acid was added THF (2 mL), followed by HATU (94 mg, 0.246 mmol), cyclopentanamine (70.0 mg, 0.822 mmol) and 4-methylmorpholine (83 mg, 0.822 mmol). The suspension was stirred at 43° C. for 36 h to afford the title compound, which was used in the next step without further purification. [M+H] calc'd for C$_{25}$H$_{34}$N$_4$O$_5$, 471; found, 471.5.

Step C: (R)-4-((2-(cyclopentylamino)-1-cyclopropyl-2-oxoethylamino)methyl)-1H-pyrrolo[2,3-b]pyridine-3-carboxylic acid

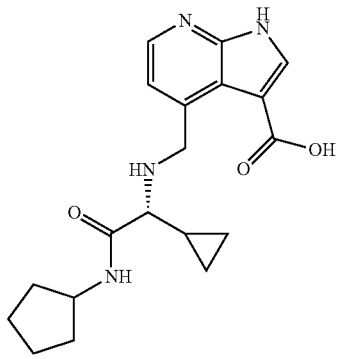 [SMILES: O=C(O)c1c[nH]c2nccc(CN[C@@H](C(=O)NC3CCCC3)C3CC3)c12]

Crude (R)-1-tert-butyl 3-methyl 4-((2-(cyclopentylamino)-1-cyclopropyl-2-oxoethylamino)methyl)-1H-pyrrolo[2,3-b]pyridine-1,3-dicarboxylate was concentrated and re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for $C_{19}H_{24}N_4O_3$, 357; found, 357.5.

Step D: (R)—N-cyclopentyl-2-cyclopropyl-2-(3-oxopyrrolo[4,3,2-de][2,6]naphthyridin-4(1H,3H,5H)-yl)acetamide In a manner similar to Step C of Example 19, (R)-4-((2-(cyclopentylamino)-1-cyclopropyl-2-oxoethylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol) and the resulting product was purified via preparative mass trigger LC-MS (AcCN/H$_2$O, 5-50%). The fractions were collected, concentrated, and dried in vacuo to afford the title compound as a yellow oil (4.4 mg, 8% from Step A starting material). $^1$H NMR (500 MHz, CD$_3$OD) δ 0.38 (d, J=5.37 Hz, 1 H) 0.73 (t, J=4.90 Hz, 1 H) 0.82 (br. s., 1 H) 1.45-1.57 (m, 2 H) 1.60 (s, 2 H) 1.73 (br. s., 2 H) 1.83-1.98 (m, 2 H) 3.09-3.22 (m, 1 H) 3.68-3.77 (m, 1 H) 4.13 (d, J=5.86 Hz, 1 H) 5.48-5.58 (m, 2 H) 7.29 (d, J=5.37 Hz, 1 H) 7.84 (s, 1 H) 8.35 (br. s., 1 H). [M+H] calc'd for $C_{19}H_{22}N_4O_2$, 339; found, 339.5.

Example 26

(R)—N-cyclopentyl-3,3-dimethyl-2-(3-oxopyrrolo[4,3,2-de][2,6]naphthyridin-4(1H,3H,5H)-yl)butanamide

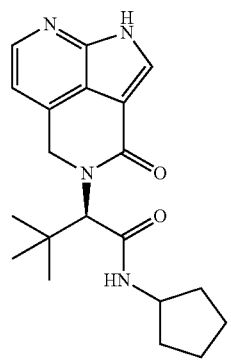 [SMILES: CC(C)(C)[C@H](C(=O)NC1CCCC1)N1Cc2ccnc3[nH]cc(c23)C1=O]

Step A: (R)-2-((1-(tert-butoxycarbonyl)-3-(methoxycarbonyl)-1H-pyrrolo[2,3-b]pyridin-4-yl)methylamino)-3,3-dimethylbutanoic acid

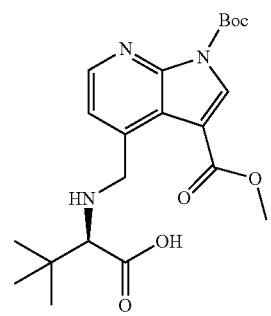 [SMILES: COC(=O)c1cn(C(=O)OC(C)(C)C)c2nccc(CN[C@@H](C(=O)O)C(C)(C)C)c12]

To a 10 mL round bottom flask was added sodium triacetoxyborohydride (104 mg, 0.493 mmol), (R)-2-amino-3,3-dimethylbutanoic acid (43.1 mg, 0.329 mmol) and DCM (2 mL). The reaction mixture were stirred at room temperature in for 30 min after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture was concentrated to afford the title compound, which was used in the next step without further purification. [M+H] calc'd for $C_{21}H_{29}N_3O_6$, 420; found, 420.3.

Step B: (R)-1-tert-butyl 3-methyl 4-((1-(cyclopentylamino)-3,3-dimethyl-1-oxobutan-2-ylamino)methyl)-1H-pyrrolo[2,3-b]pyridine-1,3-dicarboxylate

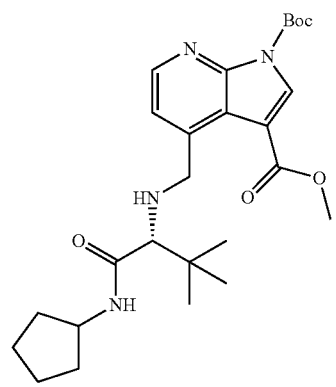 [SMILES: COC(=O)c1cn(C(=O)OC(C)(C)C)c2nccc(CN[C@@H](C(=O)NC3CCCC3)C(C)(C)C)c12]

To (R)-2-((1-(tert-butoxycarbonyl)-3-(methoxycarbonyl)-1H-pyrrolo[2,3-b]pyridin-4-yl)methylamino)-3,3-dimethylbutanoic acid was added THF (2 mL), HATU (94 mg, 0.246 mmol), cyclopentanamine (70.0 mg, 0.822 mmol) and 4-methylmorpholine (83 mg, 0.822 mmol). The suspension was stirred at 43° C. for 36 h to afford the title compound, which was used in the next step without further purification. [M+H] calc'd for $C_{26}H_{38}N_4O_5$, 487; found, 487.6.

Step C: (R)-4-((1-(cyclopentylamino)-3,3-dimethyl-1-oxobutan-2-ylamino)methyl)-1H-pyrrolo[2,3-b]pyridine-3-carboxylic acid

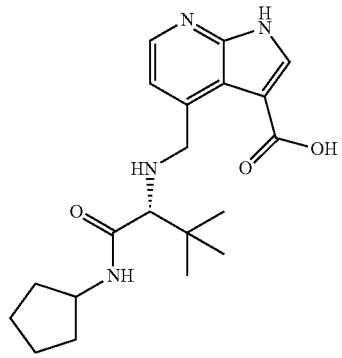 [SMILES: CC(C)(C)[C@@H](NCc1ccnc2[nH]cc(C(=O)O)c12)C(=O)NC1CCCC1]

Crude (R)-1-tert-butyl 3-methyl 4-((1-(cyclopentylamino)-3,3-dimethyl-1-oxobutan-2-ylamino)methyl)-1H-pyrrolo[2,3-b]pyridine-1,3-dicarboxylate was concentrated and was re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for C$_{20}$H$_{28}$N$_4$O$_3$, 373; found, 373.6.

Step D: (R)—N-cyclopentyl-3,3-dimethyl-2-(3-oxopyrrolo[4,3,2-de][2,6]naphthyridin-4(1H,3H,5H)-yl)butanamide In a manner similar to Step C of Example 19, (R)-4-((1-(cyclopentylamino)-3,3-dimethyl-1-oxobutan-2-ylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol), and the resulting product was purified via preparative mass trigger LC-MS (AcCN/H$_2$O, 5-50%). The fractions were collected, concentrated, and dried in vacuo to afford the title compound as a yellow oil (9.2 mg, 15.8% from Step A starting material). $^1$H NMR (400 MHz, CD$_3$OD) δ 1.16 (s, 9 H) 1.36-1.65 (m, 4 H) 1.65-1.77 (m, 2 H) 1.78-2.05 (m, 2 H) 4.11 (t, J=6.82 Hz, 1 H) 5.30-5.51 (m, 2 H) 5.51-5.69 (m, 1 H) 7.13-7.31 (m, 1 H) 7.25 (d, J=5.56 Hz, 1 H) 7.87 (s, 1 H) 8.32 (d, J=5.31 Hz, 1 H). [M+H] calc'd for C$_{20}$H$_{26}$N$_4$O$_2$, 355; found, 355.6.

Example 27

(R)—N,2-dicyclopentyl-2-(3-oxopyrrolo[4,3,2-de][2,6]naphthyridin-4(1H,3H,5H)-yl)acetamide

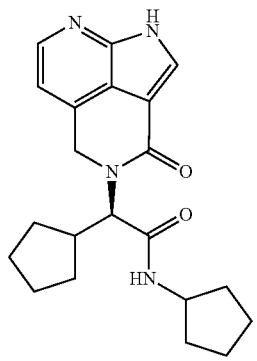 [SMILES: O=C(NC1CCCC1)[C@@H](C1CCCC1)N1Cc2ccnc3[nH]cc(c23)C1=O]

Step A: (R)-2-((1-(tert-butoxycarbonyl)-3-(methoxycarbonyl)-1H-pyrrolo[2,3-b]pyridin-4-yl)methylamino)-2-cyclopentylacetic acid

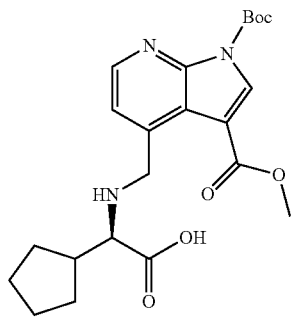 [SMILES: COC(=O)c1cn(C(=O)OC(C)(C)C)c2nccc(CN[C@@H](C(=O)O)C3CCCC3)c12]

To a 10 mL round bottom flask was added sodium triacetoxyborohydride (104 mg, 0.493 mmol), (R)-2-amino-2-cyclopentylacetic acid (47.1 mg, 0.329 mmol) and DCM (2 mL). The reaction mixture was stirred at room temperature for 30 min after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture was concentrated to afford the title compound, which was used in the next step without further purification. [M+H] calc'd for C$_{22}$H$_{29}$N$_3$O$_6$, 432; found, 432.4.

Step B: (R)-1-tert-butyl 3-methyl 4-((1-cyclopentyl-2-(cyclopentylamino)-2-oxoethylamino)methyl)-1H-pyrrolo[2,3-b]pyridine-1,3-dicarboxylate

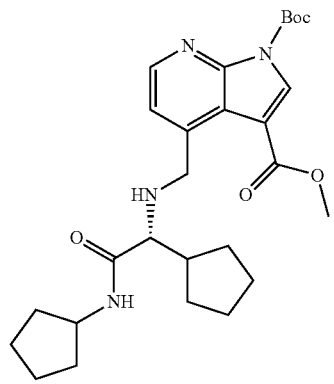 [SMILES: COC(=O)c1cn(C(=O)OC(C)(C)C)c2nccc(CN[C@@H](C(=O)NC3CCCC3)C3CCCC3)c12]

To (R)-2-((1-(tert-butoxycarbonyl)-3-(methoxycarbonyl)-1H-pyrrolo[2,3-b]pyridin-4-yl)methylamino)-2-cyclopentylacetic acid was added THF (2 mL), HATU (94 mg, 0.246 mmol), cyclopentanamine (70.0 mg, 0.822 mmol) and 4-methylmorpholine (83 mg, 0.822 mmol). The suspension was stirred at 43° C. for 36 h to afford the title compound, which was used in the next step without further purification. [M+H] calc'd for C$_{27}$H$_{38}$N$_4$O$_5$, 499; found, 499.6.

Step C: (R)-4-((1-cyclopentyl-2-(cyclopentylamino)-2-oxoethylamino)methyl)-1H-pyrrolo[2,3-b]pyridine-3-carboxylic acid

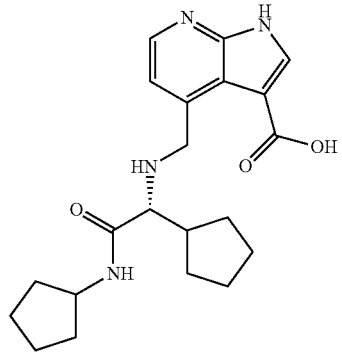 [SMILES: O=C(O)c1c[nH]c2nccc(CN[C@@H](C(=O)NC3CCCC3)C3CCCC3)c12]

Crude (R)-1-tert-butyl 3-methyl 4-((1-cyclopentyl-2-(cyclopentylamino)-2-oxoethylamino)methyl)-1H-pyrrolo[2,3-b]pyridine-1,3-dicarboxylate was concentrated and re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for $C_{21}H_{28}N_4O_3$, 384; found, 384.6.

Step D: (R)—N,2-dicyclopentyl-2-(3-oxopyrrolo[4,3,2-de][2,6]naphthyridin-4(1H,3H,5H)-yl)acetamide In a manner similar to Step C of Example 19, (R)-4-((1-cyclopentyl-2-(cyclopentylamino)-2-oxoethylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol), and the resulting product was purified via preparative mass trigger LC-MS (AcCN/H$_2$O, 5-50%). The fractions were collected, concentrated, and dried in vacuo to afford the title compound as a yellow oil (11 mg, 18.7% from Step A starting material). $^1$H NMR (400 MHz, CD$_3$OD) δ 1.22-1.34 (m, 1 H) 1.34-1.45 (m, 2 H) 1.54-1.78 (m, 10 H) 1.78-2.00 (m, 3 H) 2.65-2.84 (m, 1 H) 4.00-4.15 (m, 1 H) 5.08 (d, J=11.37 Hz, 1 H) 5.21 (s, 1 H) 5.47 (s, 1 H) 7.12-7.36 (m, 1 H) 7.24 (d, J=5.31 Hz, 1 H) 7.86 (s, 1 H) 8.32 (d, J=5.31 Hz, 1 H). [M+H] calc'd for $C_{21}H_{26}N_4O_2$, 367; found, 367.6.

Example 28

(R)—N-cyclopentyl-4,4,4-trifluoro-2-(3-oxopyrrolo[4,3,2-de][2,6]naphthyridin-4(1H,3H,5H)-yl)butanamide

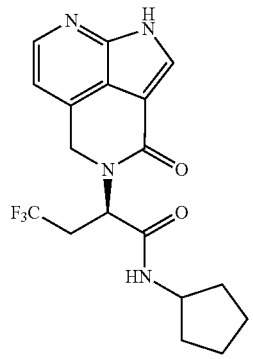 [SMILES: O=C(NC1CCCC1)[C@@H](CC(F)(F)F)N1Cc2ccnc3[nH]cc(c23)C1=O]

Step A: (R)-2-((1-(tert-butoxycarbonyl)-3-(methoxycarbonyl)-1H-pyrrolo[2,3-b]pyridin-4-yl)methylamino)-4,4,4-trifluorobutanoic acid

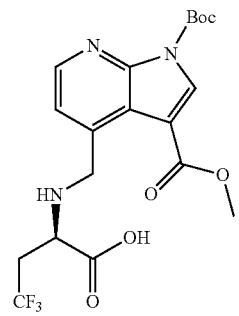 [SMILES: COC(=O)c1cn(C(=O)OC(C)(C)C)c2nccc(CN[C@H](CC(F)(F)F)C(=O)O)c12]

To a 10 mL round bottom flask was added sodium triacetoxyborohydride (104 mg, 0.493 mmol), 2-amino-4,4,4-trifluorobutanoic acid (51.6 mg, 0.329 mmol) and DCM (2 mL). The reaction mixture was stirred for 30 min after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture was concentrated to afford the title compound, which was used in the next step without further purification. [M+H] calc'd for $C_{19}H_{22}F_3N_3O_6$, 446; found, 446.5.

Step B: (R)-1-tert-butyl 3-methyl 4-((1-(cyclopentylamino)-4,4,4-trifluoro-1-oxobutan-2-ylamino)methyl)-1H-pyrrolo[2,3-b]pyridine-1,3-dicarboxylate

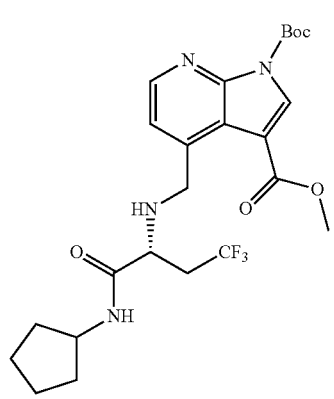 [SMILES: COC(=O)c1cn(C(=O)OC(C)(C)C)c2nccc(CN[C@H](CC(F)(F)F)C(=O)NC3CCCC3)c12]

To (R)-2-((1-(tert-butoxycarbonyl)-3-(methoxycarbonyl)-1H-pyrrolo[2,3-b]pyridin-4-yl)methylamino)-4,4,4-trifluorobutanoic acid was added THF (2 mL), HATU (94 mg, 0.246 mmol), cyclopentanamine (70.0 mg, 0.822 mmol) and 4-methylmorpholine (83 mg, 0.822 mmol). The resulting suspension was stirred at 43° C. for 36 h to afford the title compound, which was used in the next step without further purification. [M+H] calc'd for $C_{24}H_{31}F_3N_4O_5$, 513; found, 513.6.

Step C: (R)-4-((1-(cyclopentylamino)-4,4,4-trifluoro-1-oxobutan-2-ylamino)methyl)-1H-pyrrolo[2,3-b]pyridine-3-carboxylic acid

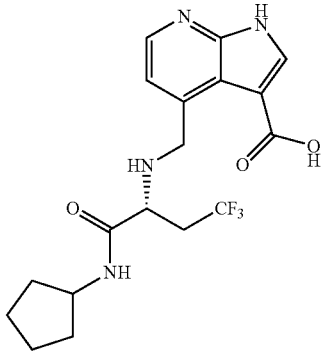 [SMILES: O=C(O)c1c[nH]c2nccc(CN[C@H](CC(F)(F)F)C(=O)NC3CCCC3)c12]

Crude (R)-1-tert-butyl 3-methyl 4-((1-(cyclopentylamino)-4,4,4-trifluoro-1-oxobutan-2-ylamino)methyl)-1H-pyrrolo[2,3-b]pyridine-1,3-dicarboxylate was concentrated and re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for C$_{18}$H$_{21}$F$_3$N$_4$O$_3$, 399; found, 399.6.

Step D: (R)—N-cyclopentyl-4,4,4-trifluoro-2-(3-oxopyrrolo[4,3,2-de][2,6]naphthyridin-4(1H,3H,5H)-yl)butanamide In a manner similar to Step C of Example 19, (R)-4-((1-(cyclopentylamino)-4,4,4-trifluoro-1-oxobutan-2-ylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol) and the resulting product was purified via preparative mass trigger LC-MS (AcCN/H$_2$O, 5-50%). The fractions were collected, concentrated, and dried in vacuo to afford the title compound as a yellow oil (4.5 mg, 7.2% from Step A starting material). $^1$H NMR (400 MHz, CD$_3$OD) δ 1.32-1.62 (m, 4 H) 1.62-1.78 (m, 2 H) 1.82-2.05 (m, 2 H) 2.87-3.07 (m, 1 H) 3.07-3.21 (m, 1 H) 4.10-4.24 (m, 1 H) 5.13 (d, J=19.20 Hz, 1 H) 5.26 (d, J=18.95 Hz, 1 H) 5.41 (dd, J=8.08, 5.31 Hz, 1 H) 7.24 (d, J=5.31 Hz, 1 H) 7.90 (s, 1 H) 8.36 (d, J=5.05 Hz, 1 H). [M+H] calc'd for C$_{18}$H$_{19}$F$_3$N$_4$O$_2$, 381; found, 381.5.

Preparation I:

(R)-2-amino-N-cyclopentyl-3-hydroxy-3-methylbutanamide

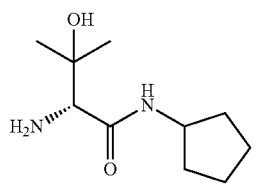

Step A: (R)-tert-butyl 1-(cyclopentylamino)-3-hydroxy-3-methyl-1-oxobutan-2-ylcarbamate

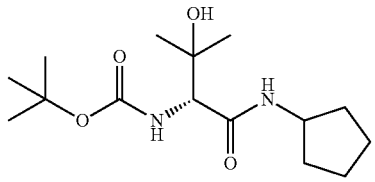 [SMILES: CC(C)(C)OC(=O)N[C@@H](C(=O)NC1CCCC1)C(C)(C)O]

To a mixture of (R)-2-(tert-butoxycarbonylamino)-3-hydroxy-3-methylbutanoic acid (0.5 g, 2.144 mmol), HATU (0.978 g, 2.57 mmol) and cyclopentanamine (0.423 mL, 4.29 mmol) in DCM (10 mL) was added Et$_3$N (0.598 mL, 4.29 mmol). The reaction mixture was stirred at room temperature for 5 h and then washed with saturated aqueous NaHCO$_3$ and brine. The organics were dried over MgSO$_4$, concentrated, and purified by silica column chromatography (MeOH/DCM, 0-10%) to afford the title compound (0.6 g, 93%).

Step B: (R)-2-amino-N-cyclopentyl-3-hydroxy-3-methylbutanamide

A mixture of (R)-tert-butyl 1-(cyclopentylamino)-3-hydroxy-3-methyl-1-oxobutan-2-ylcarbamate and 50% TFA/DCM (10 mL) was stirred for 1 h. The resulting product was concentrated and isolated as clear oil, TFA salt. Purification by flash column chromatography (MeOH/DCM, 0-10%) afforded the title compound as a white solid (free base, 0.37 g, 93%). $^1$H NMR (400 MHz, DMSO-d$_6$) δ 1.13 (s, 3 H) 1.23 (s, 3 H) 1.40 (s, 2 H) 1.44-1.69 (m, 4 H) 1.73-2.01 (m, 2 H) 3.48 (s, 1 H) 3.89-4.16 (m, 1 H) 5.33 (s, 1 H) 7.87-7.89 (m, 2 H) 8.33 (d, J=7.33 Hz, 1 H).

Example 29

(R)—N-cyclopentyl-3-hydroxy-3-methyl-2-(3-oxopyrrolo[4,3,2-de][2,6]naphthyridin-4(1H,3H,5H)-yl)butanamide

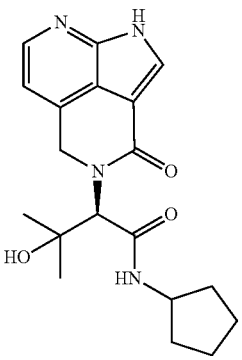 [SMILES: CC(C)(O)[C@H](C(=O)NC1CCCC1)N1Cc2ccnc3[nH]cc(c23)C1=O]

Step A: (R)-1-tert-butyl 3-methyl 4-((1-(cyclopentylamino)-3-hydroxy-3-methyl-1-oxobutan-2-ylamino)methyl)-1H-pyrrolo[2,3-b]pyridine-1,3-dicarboxylate

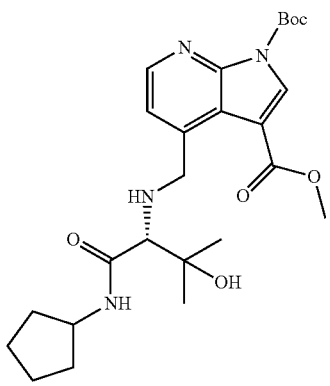 [SMILES: COC(=O)c1cn(C(=O)OC(C)(C)C)c2nccc(CN[C@@H](C(=O)NC3CCCC3)C(C)(C)O)c12]

A mixture of sodium triacetoxyborohydride (104 mg, 0.493 mmol) and (R)-2-amino-N-cyclopentyl-3-hydroxy-3-methylbutanamide (49.4 mg, 0.246 mmol) in DCE (2 mL) was stirred at room temperature for 30 min. 1-tert-Butyl 3-methyl 4-formyl-1H-pyrrolo[2,3-b]pyridine-1,3-dicarboxylate (75 mg, 0.246 mmol) was added and the reaction mixture was stirred at room temperature for 1 h. Following reaction, the mixture was concentrated to afford the title compound. [M+H] calc'd for $C_{25}H_{36}N_4O_6$, 489; found, 489.3.

Step B: (R)-4-((1-(cyclopentylamino)-3-hydroxy-3-methyl-1-oxobutan-2-ylamino)methyl)-1H-pyrrolo[2,3-b]pyridine-3-carboxylic acid

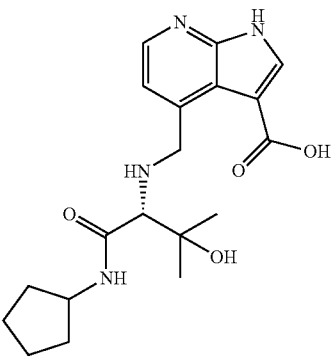 [SMILES: CC(C)(O)[C@@H](NCc1ccnc2[nH]cc(C(=O)O)c12)C(=O)NC1CCCC1]

To (R)-1-tert-butyl 3-methyl 4-((1-(cyclopentylamino)-3-hydroxy-3-methyl-1-oxobutan-2-ylamino)methyl)-1H-pyrrolo[2,3-b]pyridine-1,3-dicarboxylate was added MeOH (1 mL) and aqueous NaOH (12N, 2 mL). The reaction mixture was stirred at 53° C. for 16 h and the resulting product was purified via preparative mass trigger LC-MS (AcCN/H$_2$O, 5-90%). The fractions were collected, concentrated, and dried in vacuo to afford the title compound. [M+H] calc'd for $C_{19}H_{26}N_4O_4$, 375; found, 374.5.

Step C: (R)—N-cyclopentyl-3-hydroxy-3-methyl-2-(3-oxopyrrolo[4,3,2-de][2,6]naphthyridin-4(1H,3H,5H)-yl)butanamide In a manner similar to Step C of Example 19, (R)-4-((1-(cyclopentylamino)-3-hydroxy-3-methyl-1-oxobutan-2-ylamino)methyl)-1H-pyrrolo[2,3-b]pyridine-3-carboxylic acid was cyclized in a mixture of THF (2 mL), HATU (112 mg, 0.296 mmol) and 4-methylmorpholine (37.4 mg, 0.370 mmol) and the resulting product was purified via preparative mass trigger LC-MS (AcCN/H$_2$O, 5-50%). The fractions were collected, concentrated, and dried in vacuo to afford the title compound as a yellow oil (6.5 mg, 7.4% from Step A starting material). $^1$H NMR (500 MHz, CD$_3$OD) δ 1.20 (s, 3 H) 1.37-1.41 (m, 3 H) 1.41-1.79 (m, 5 H) 1.85-2.00 (m, 3 H) 4.19 (s, 1 H) 5.14-5.26 (m, 1 H) 5.35 (s, 1 H) 5.64-5.77 (m, 1 H) 7.22 (d, J=5.37 Hz, 1 H) 7.89 (s, 1 H) 8.31 (d, J=5.37 Hz, 1 H). [M+H] calc'd for $C_{19}H_{24}N_4O_3$, 357; found, 357.5.

Preparation J: (R)-2-amino-3-cyano-N-cyclopentylpropanamide

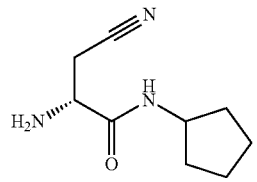 [SMILES: N#CC[C@@H](N)C(=O)NC1CCCC1]

Step A: (R)-tert-butyl 3-cyano-1-(cyclopentylamino)-1-oxopropan-2-ylcarbamate

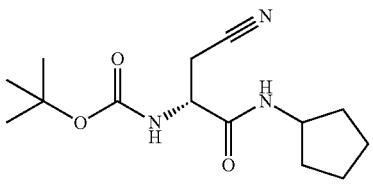 [SMILES: CC(C)(C)OC(=O)N[C@H](CC#N)C(=O)NC1CCCC1]

To a mixture of (R)-2-(tert-butoxycarbonylamino)-3-cyanopropanoic acid (0.5 g, 2.334 mmol), HATU (0.986 g, 2.59 mmol) and cyclopentanamine (0.461 mL, 4.67 mmol) in DCM (10 mL) was added Et$_3$N (0.651 mL, 4.67 mmol). The reaction mixture was stirred at room temperature for 5 h and then washed with saturated aqueous NaHCO$_3$ and brine. The organics were dried over MgSO$_4$ and concentrated. Purification by silica column chromatography (MeOH/DCM, 0-10%) afforded the title compound (0.61 g, 93%). $^1$H NMR (400 MHz, CD$_3$OD) δ1.50 (s, 9 H) 1.57-1.73 (m, 4 H) 1.79-1.87 (m, 3 H) 1.89-2.02 (m, 1 H) 2.05-2.19 (m, 3 H) 2.76-2.95 (m, 1 H) 3.87 (t, J=7.07 Hz, 1 H).

Step B: (R)-2-amino-3-cyano-N-cyclopentylpropanamide

A mixture of (R)-tert-butyl 3-cyano-1-(cyclopentylamino)-1-oxopropan-2-ylcarbamate and 50% TFA/DCM (10 mL) was stirred for 1 h. Following reaction, the mixture was concentrated to afford the title compound as a clear oil (TFA salt, 0.265 g, 41%). The product was pure by TLC (visualized by ninhydrin stain).

Preparation K:

5-chloro-4-formyl-1-tosyl-1H-pyrrolo[2,3-b]pyridine-3-carboxylic acid

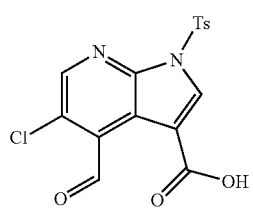 [SMILES: Cc1ccc(S(=O)(=O)n2cc(C(=O)O)c3c(C=O)c(Cl)cnc32)cc1]

Step A: 5-chloro-3-iodo-1-tosyl-1H-pyrrolo[2,3-b]pyridine-4-carbaldehyde

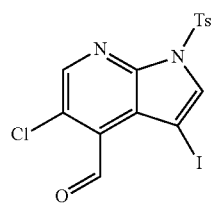 [SMILES: Cc1ccc(S(=O)(=O)n2cc(I)c3c(C=O)c(Cl)cnc32)cc1]

To a solution of 5-chloro-1H-pyrrolo[2,3-b]pyridine-4-carbaldehyde (5.0 g, 27.7 mmol) in EtOH (100 mL) was added iodine (8.43 g, 33.2 mmol), sodium iodide (4.98 g, 33.2 mmol), and aqueous NaOH (1N, 35 mL, 35 mmol). After stirring for 4 h at room temperature, the reaction mixture was diluted with water (200 mL). An orange precipitate was collected by filtration and dried under vacuum. The solid was dissolved in DMF (60 mL) and sodium hydride (60%, 1.33 g, 33.2 mmol) was slowly added. The deep red solution was stirred for 30 min at room temperature. Tosyl chloride (5.81 g, 30.5 mmol) was added and the mixture was stirred at room temperature for 2 h. The mixture was diluted with EtOAc and the reaction was quenched with water. The organics were separated, washed with aqueous NaHSO$_3$ (0.1 N) and brine, dried over MgSO$_4$, and concentrated. Purification by silica gel chromatography (3:1:1 hexane/DCM/EtOAc) gave the title compound as a yellow solid (8.96 g, 70%). $^1$H NMR (500 MHz, DMSO-d$_6$) δ 3.15 (s, 3 H), 8.24 (d, J=8.5 Hz, 2 H), 8.81 (d, J=8.5 Hz, 2 H), 9.17 (s, 1 H), 9.38 (s, 1 H), 11.81 (s, 1 H). [M+H] calc'd for C$_{15}$H$_{10}$ClIN$_2$O$_3$S, 461, 463; found, 461, 463.

Step B: 5-chloro-4-formyl-1-tosyl-1H-pyrrolo[2,3-b]pyridine-3-carboxylic acid

Lithium chloride (1.05 g, 24.7 mmol) and lithium formate monohydrate (1.73 g, 24.7 mmol) were combined in a dry sealable tube under nitrogen. DMF (20 mL), 5-chloro-3-iodo-1-tosyl-1H-pyrrolo[2,3-b]pyridine-4-carbaldehyde (3.8 g, 8.25 mmol), acetic anhydride (1.56 mL, 16.5 mmol) and palladium acetate (185 mg, 0.83 mmol) were added. DIPEA (2.87 mL) was added, and the reaction tube was sealed and heated at 52° C. for 3 h. The reaction mixture was taken up in MeOH/DCM (20%) and filtered to remove the insoluble black carbon material. The yellow solution was concentrated in vacuo, dissolved in MeOH/DCM (10%), and washed with aqueous HCl (0.1N). The aqueous layer was extracted with MeOH/DCM (10%, 2×). The organics were combined, dried over MgSO$_4$, and concentrated in vacuo. Purification by silica gel chromatography (10-15% MeOH/DCM) gave the title compound as a light tan solid (2.34 g, 75%). $^1$H NMR (500 MHz, CD$_3$OD) δ 3.15 (s, 3H), 8.24 (d, J=8.5 Hz, 2H), 8.81 (d, J=8.5 Hz, 2H), 9.17 (s, 1H), 9.38 (s, 1H), 11.81 (s, 1H). [M+H] calc'd for C$_{16}$H$_{11}$ClN$_2$O$_5$S, 379, 381; found, 379, 381.

Example 30

(R)-2-(6-chloro-3-oxopyrrolo[4,3,2-de][2,6]naphthyridin-4(1H,3H,5H)-yl)-3-cyano-N-cyclopentylpropanamide

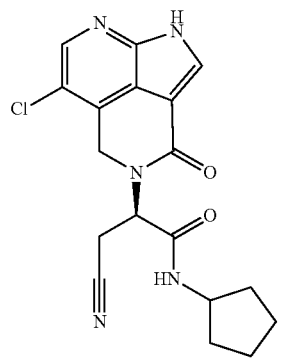 [SMILES: N#CC[C@H](C(=O)NC1CCCC1)N1Cc2c(Cl)cnc3[nH]cc(c23)C1=O]

Step A: (R)-5-chloro-4-((3-cyano-1-(cyclopentylamino)-1-oxopropan-2-ylamino)methyl)-1-tosyl-1H-pyrrolo[2,3-b]pyridine-3-carboxylic acid

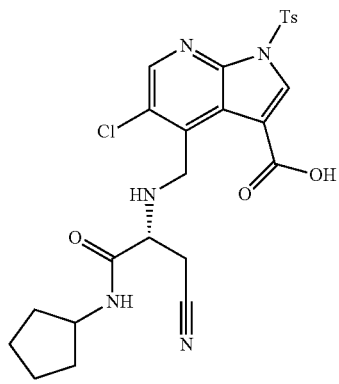 [SMILES: Cc1ccc(S(=O)(=O)n2cc(C(=O)O)c3c(CN[C@H](CC#N)C(=O)NC4CCCC4)c(Cl)cnc32)cc1]

A mixture of sodium triacetoxyborohydride (26.5 mg, 0.125 mmol) and (R)-2-amino-3-cyano-N-cyclopentylpropanamide (22.70 mg, 0.125 mmol) in DCM (1 mL) was stirred at room temperature for 10 min. The reaction mixture was cooled to 0° C. A solution of 5-chloro-4-formyl-1-tosyl-1H-pyrrolo[2,3-b]pyridine-3-carboxylic acid (30 mg, 0.063 mmol) in DCM (1 mL) was added. The reaction mixture was stirred at 0° C. for 20 min and then concentrated to afford the title compound. [M+H] calc'd for $C_{26}H_{28}ClN_5O_5S$, 544; found, 544.2.

Step B: (R)-2-(6-chloro-3-oxo-1-tosylpyrrolo[4,3,2-de][2,6]naphthyridin-4(1H,3H,5H)-yl)-3-cyano-N-cyclopentylpropanamide

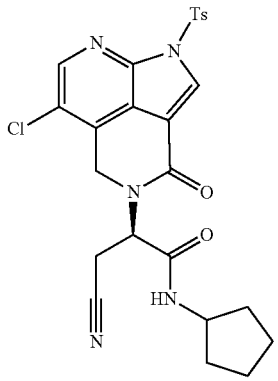 [SMILES: Cc1ccc(S(=O)(=O)n2cc3c4c(c(Cl)cnc42)CN([C@H](CC#N)C(=O)NC2CCCC2)C3=O)cc1]

A mixture of (R)-5-chloro-4-((3-cyano-1-(cyclopentylamino)-1-oxopropan-2-ylamino)methyl)-1-tosyl-1H-pyrrolo[2,3-b]pyridine-3-carboxylic acid, THF (5 mL), HATU (28.6 mg, 0.075 mmol) and 4-methylmorpholine (19.01 mg, 0.188 mmol) was stirred at room temperature for 2 h. The product was purified via preparative mass trigger LC-MS (AcCN/H$_2$O, 5-90%). The fractions were collected, concentrated, and dried in vacuo to afford the title compound. [M+H] calc'd for $C_{25}H_{24}ClN_5O_4S$, 526; found, 526.2.

Step C: (R)-2-(6-chloro-3-oxopyrrolo[4,3,2-de][2,6]naphthyridin-4(1H,3H,5H)-yl)-3-cyano-N-cyclopentylpropanamide To a solution of (R)-2-(6-chloro-3-oxo-1-tosylpyrrolo[4,3,2-de][2,6]naphthyridin-4(1H,3H,5H)-yl)-3-cyano-N-cyclopentylpropanamide in MeOH (2 mL) was added aqueous NaOH (1N, 0.5 mL). The reaction mixture was stirred for 20 min and the product was purified via preparative mass trigger LC-MS (AcCN/H$_2$O, 5-50%). The fractions were collected, concentrated, and dried in vacuo to afford the title compound as a yellow oil (0.5 mg, 2.1% from Step A starting material). $^1$H NMR (400 MHz, CD$_3$OD) δ 1.37-1.72 (m, 4 H) 1.83-1.95 (m, 4 H) 3.22-3.26 (m, 2 H) 3.69-3.76 (m, 1 H) 5.11 (s, 1 H) 5.14-5.17 (m, 1 H) 5.18 (s, 1 H) 7.88 (s, 1 H) 8.27 (s, 1 H). [M+H] calc'd for $C_{18}H_{18}ClN_5O_2$, 372; found, 372.4.

Example 31

N-cyclopentyl-1-(3-oxopyrrolo[4,3,2-de][2,6]naphthyridin-4(1H,3H,5H)-yl)cyclopentanecarboxamide

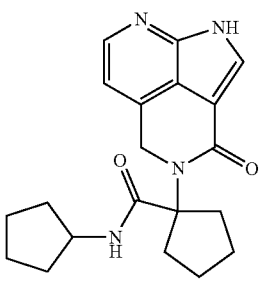 [SMILES: O=C1c2c[nH]c3nccc(c23)CN1C1(C(=O)NC2CCCC2)CCCC1]

Step A: 1-((1-(tert-butoxycarbonyl)-3-(methoxycarbonyl)-1H-pyrrolo[2,3-b]pyridin-4-yl)methylamino)cyclopentanecarboxylic acid

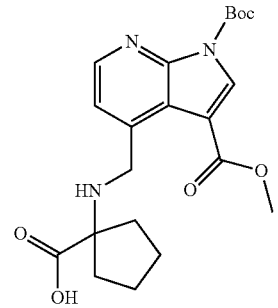

To a 10 mL round bottom flask was added sodium triacetoxyborohydride (104 mg, 0.493 mmol) and 1-aminocyclopentanecarboxylic acid (42.4 mg, 0.329 mmol) in DCM (2 mL). The reaction mixture was stirred at room temperature for 30 min after which was added 1-tert-butyl 3-methyl 4-formyl-1H-pyrrolo[2,3-b]pyridine-1,3-dicarboxylate (50 mg, 0.164 mmol) in DCM (2 mL). The reaction was stirred at room temperature for 2 h and then quenched with MeOH (3 drops). The mixture was concentrated to afford the title compound, which was used in the next step without further purification. [M+H] calc'd for $C_{21}H_{27}N_3O_6$, 418; found, 418.3.

Step B: 1-tert-butyl 3-methyl 4-((1-(cyclopentylcarbamoyl)cyclopentylamino)methyl)-1H-pyrrolo[2,3-b]pyridine-1,3-dicarboxylate

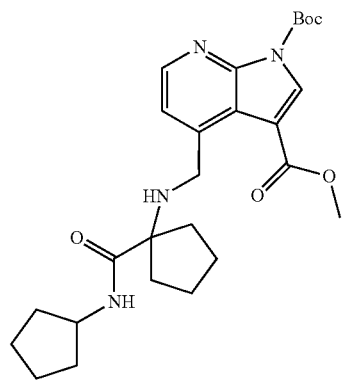

To 1-((1-(tert-butoxycarbonyl)-3-(methoxycarbonyl)-1H-pyrrolo[2,3-b]pyridin-4-yl)methylamino)cyclopentanecarboxylic acid was added THF (2 mL), HATU (94 mg, 0.246 mmol), cyclopentanamine (70.0 mg, 0.822 mmol) and 4-methylmorpholine (83 mg, 0.822 mmol). The suspension was stirred at 43° C. for 36 h to afford the title compound, which was used in the next step without further purification. [M+H] calc'd for $C_{26}H_{36}N_4O_5$, 485; found, 485.4.

Step C: 4-((1-(cyclopentylcarbamoyl)cyclopentylamino)methyl)-1H-pyrrolo[2,3-b]pyridine-3-carboxylic acid

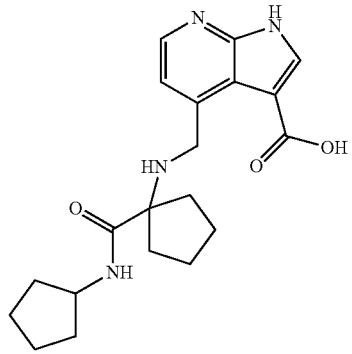

Crude 1-tert-butyl 3-methyl 4-((1-(cyclopentylcarbamoyl)cyclopentylamino)methyl)-1H-pyrrolo[2,3-b]pyridine-1,3-dicarboxylate was concentrated and re-dissolved in MeOH (1 mL). Aqueous NaOH (12N, 2 mL) was added and the reaction mixture was stirred at 53° C. for 16 h. The product was purified via preparative mass trigger LC-MS (AcCN/H$_2$O, 5-50%). The fractions were collected, concentrated, and dried in vacuo to afford the title compound. [M+H] calc'd for C$_{20}$H$_{26}$N$_4$O$_3$, 371; found, 371.6.

Step D: N-cyclopentyl-1-(3-oxopyrrolo[4,3,2-de][2,6]naphthyridin-4(1H,3H,5H)-yl)cyclopentanecarboxamide In a manner similar to Step C of Example 19, 4-(1-(cyclopentylcarbamoyl)cyclo-pentylamino)methyl)-1H-pyrrolo[2,3-b]pyridine-3-carboxylic acid was cyclized in a mixture of THF (2 mL), HATU (94 mg, 0.246 mmol) and 4-methylmorpholine (83 mg, 0.822 mmol) and the product was purified via preparative mass trigger LC-MS (AcCN/H$_2$O, 5-50%). The fractions were collected, concentrated, and dried in vacuo to afford the title compound as a yellow oil (2.7 mg, 4.8% from Step A starting material). $^1$H NMR (500 MHz, CD$_3$OD) δ 1.45 (d, J=7.32 Hz, 1 H) 1.52 (d, J=4.88 Hz, 1 H) 1.61 (br. s., 1 H) 1.79 (br. s., 2 H) 1.82-1.91 (m, 1 H) 1.96-2.02 (m, 1 H) 2.06-2.23 (m, 4 H) 2.50 (d, J=13.18 Hz, 1 H) 2.98 (br. s., 1 H) 3.21-3.29 (m, 2 H) 3.38-3.42 (m, 1 H) 4.03-4.17 (m, 1 H) 5.29 (s, 1 H) 7.20 (br. s., 1 H) 7.75 (s, 1 H) 8.31 (br. s., 1 H). [M+H] calc'd for C$_{20}$H$_{24}$N$_4$O$_2$, 353; found, 353.5.

Preparation L:

(R)-2-(6-chloro-3-oxopyrrolo[4,3,2-de][2,6]naphthyridin-4(1H,3H,5H)-yl)-3-methylbutanoic acid

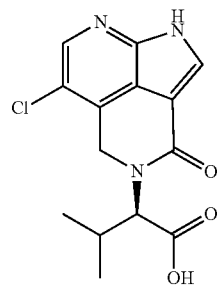 [SMILES: CC(C)[C@H](C(=O)O)N1Cc2c(Cl)cnc3[nH]cc(c23)C1=O]

Step A: (R)-tert-butyl 2-((5-chloro-3-formyl-1-tosyl-1H-pyrrolo[2,3-b]pyridin-4-yl)methylamino)-3-methylbutanoate

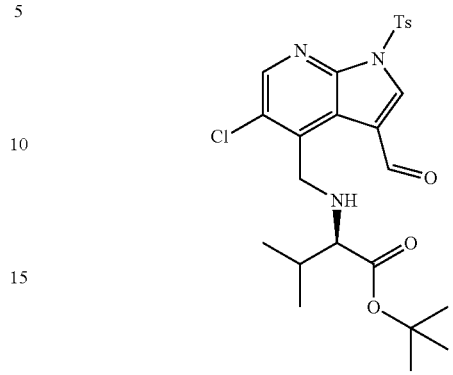

Sodium triacetoxyborohydride (517 mg, 2.44 mmol) and D-valine-tert-butyl ester, HCl salt (512 mg, 2.44 mmol) were combined in DCM (15 mL). The reaction mixture was stirred at room temperature for 20 min and was cooled to 0° C. 5-Chloro-4-formyl-1-tosyl-1H-pyrrolo[2,3-b]pyridine-3-carboxylic acid (660 mg, 1.74 mmol) was added and the reaction was stirred at 0° C. for 1 h. The solution was concentrated in vacuo to give the title compound as a yellow foam, which was used in the next step without further purification.

Step B: (R)-tert-butyl 2-(6-chloro-3-oxo-1-tosylpyrrolo[4,3,2-de][2,6]naphthyridin-4(1H,3H,5H)-yl)-3-methylbutanoate

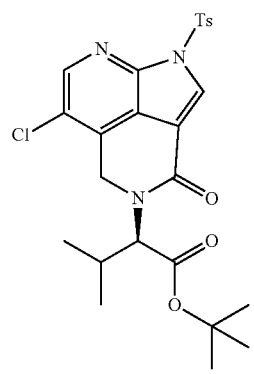 [SMILES: Cc1ccc(S(=O)(=O)n2cc3c4c(c(Cl)cnc42)CN([C@@H](C(=O)OC(C)(C)C)C(C)C)C3=O)cc1]

(R)-tert-butyl 2-((5-chloro-3-formyl-1-tosyl-1H-pyrrolo[2,3-b]pyridin-4-yl)methylamino)-3-methylbutanoate was re-dissolved in THF (40 mL). HATU (994 mg, 2.61 mmol) and N-methylmorpholine (291 μL, 2.61 mmol) were added and the reaction mixture was stirred at 50° C. for 2 h. Additional HATU (497 mg, 1.30 mmol) and N-methylmorpholine (85 μL, 1.30 mmol) were added and the reaction mixture was stirred for an additional 2 h at 50° C. The reaction mixture was subsequently cooled, diluted with EtOAc, and washed with brine. The organics were dried over MgSO$_4$ and concentrated in vacuo. Purification by silica gel chromatography (1:2:2 EtOAc/Hexanes/DCM) gave the title compound as a yellow solid (660 mg, 73% from Step A starting material). $^1$H NMR (500 MHz, CDCl$_3$) δ 0.80 (d, J=7.0 Hz, 3H), 1.01 (d, J=7.0 Hz, 3H), 1.36 (s, 9H), 2.29-2.36 (m, 1H), 2.34 (s, 3H), 4.77-5.04 (m, 3H), 7.44 (d, J=8.5 Hz, 2H), 8.06 (d, J=8.5 Hz, 2H), 8.28 (s, 1H), 8.47 (s, 1H). [M+H] calc'd for C$_{25}$H$_{28}$ClN$_3$O$_5$S, 518, 520; found, 518, 520.

Step C: (R)-2-(6-chloro-3-oxopyrrolo[4,3,2-de][2,6]naphthyridin-4(1H,3H,5H)-yl)-3-methylbutanoic acid A mixture of (R)-tert-butyl 2-(6-chloro-3-oxo-1-tosylpyrrolo[4,3,2-de][2,6]naphthyridin-4(1H,3H,5H)-yl)-3-methylbutanoate (650 mg, 1.25 mmol), EtOH (4 mL), and aqueous NaOH (1N, 2 mL) was stirred at room temperature for 40 min. The mixture was subsequently diluted with DCM and washed with brine. The organics were dried over $MgSO_4$ and concentrated in vacuo. Purification by silica gel chromatography (5% MeOH/DCM) gave a yellow oil (425 mg), which was dissolved in 50% TFA/DCM. The solution was stirred at room temperature for 1 h, concentrated, and dried under vacuum to give the title compound as a yellow solid (360 mg, 93%). $^1$H NMR (500 MHz, $CD_3OD$) δ 0.91 (d, J=7.0 Hz, 3H), 1.11 (d, J=7.0 Hz, 3H), 2.36-2.47 (m, 1H), 4.80-5.08 (m, 3H), 7.76 (s, 1H), 8.19 (s, 1H). [M+H] calc'd for $C_{14}H_{14}ClN_3O_3$, 308, 310; found, 308, 310.

Example 32

(R)-2-(6-chloro-3-oxopyrrolo[4,3,2-de][2,6]naphthyridin-4(1H,3H,5H)-yl)-N-(cyanomethyl)-3-methylbutanamide

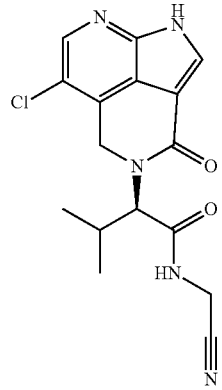 [SMILES: CC(C)[C@H](C(=O)NCC#N)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), 2-aminoacetonitrile (3.64 mg, 0.065 mmol) and HATU (14.83 mg, 0.039 mmol) were added and the solution was stirred at 25° C. for 1 h. The reaction mixture was purified via preparative mass trigger LC-MS (AcCN/$H_2O$, 5-50%). The fractions were collected, concentrated, and dried in vacuo to afford the title compound as a yellow oil (3.8 mg, 33.8%). $^1$H NMR (400 MHz, $CD_3OD$) δ 0.85-0.97 (m, 3 H) 1.02 (d, J=6.57 Hz, 1 H) 1.07 (d, J=6.32 Hz, 2 H) 2.53 (dt, J=11.18, 6.54 Hz, 1 H) 3.52-3.86 (m, 2 H) 4.89-5.04 (m, 1 H) 5.07 (d, J=11.37 Hz, 1 H) 5.51 (d, J=10.86 Hz, 1 H) 7.80-7.89 (m, 1 H) 8.13-8.34 (m, 1 H). [M+H] calc'd for $C_{16}H_{16}ClN_5O_2$, 346; found, 346.4.

Example 33

1-((R)-2-(6-chloro-3-oxopyrrolo[4,3,2-de][2,6]naphthyridin-4(1H,3H,5H)-yl)-3-methylbutanoyl)pyrrolidine-3-carbonitrile

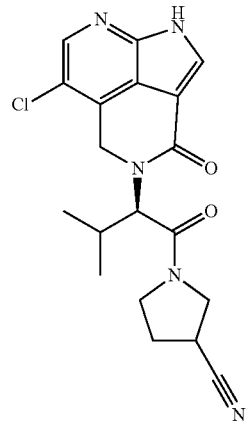 [SMILES: CC(C)[C@H](C(=O)N1CCC(C#N)C1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), pyrrolidine-3-carbonitrile (3.12 mg, 0.032 mmol) and HATU (14.83 mg, 0.039 mmol) were added and the solution was stirred at 25° C. for 1 h. The reaction mixture was purified via preparative mass trigger LC-MS (AcCN/$H_2O$, 5-50%). The fractions were collected, concentrated, and dried in vacuo to afford the title compound as a yellow oil (1.3 mg, 10.4%). $^1$H NMR (400 MHz, $CD_3OD$) δ 0.92 (s, 3 H) 1.00-1.12 (m, 3 H) 2.27-2.35 (m, 1 H) 2.56 (d, J=6.57 Hz, 1 H) 3.40 (d, J=6.82 Hz, 1 H) 3.51-3.68 (m, 1 H) 3.74 (d, J=6.57 Hz, 1 H) 3.79-3.94 (m, 1 H) 3.96-4.03 (m, 1 H) 4.88-5.00 (m, 2 H) 5.03-5.23 (m, 1 H) 5.39-5.48 (m, 1 H) 7.87 (d, J=12.63 Hz, 1 H) 8.21-8.30 (m, 1 H). [M+H] calc'd for $C_{19}H_{20}ClN_5O_2$, 386; found, 386.4.

Example 34

(R)-1-(2-(6-chloro-3-oxopyrrolo[4,3,2-de][2,6]naphthyridin-4(1H,3H,5H)-yl)-3-methylbutanoyl)piperidine-4-carbonitrile

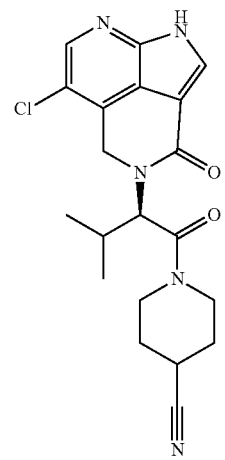 [SMILES: CC(C)[C@H](C(=O)N1CCC(C#N)CC1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), piperidine-4-carbonitrile (3.58 mg, 0.032 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a yellow oil (3.3 mg, 25.4%). $^1$H NMR (400 MHz, CD$_3$OD) δ 0.84-0.93 (m, 3 H) 0.96-1.08 (m, 3 H) 1.42-1.60 (m, 1 H) 1.72-1.82 (m, 2 H) 1.82-2.00 (m, 1 H) 2.49-2.66 (m, 1 H) 2.92-3.07 (m, 1 H) 3.49-3.73 (m, 2 H) 3.78-4.00 (m, 1 H) 4.00-4.11 (m, 1 H) 4.90 (d, J=7.58 Hz, 1 H) 4.92-5.01 (m, 1 H) 5.53 (dd, J=10.86, 3.54 Hz, 1 H) 7.82-7.92 (m, 1 H) 8.15-8.30 (m, 1 H). [M+H] calc'd for C$_{20}$H$_{22}$ClN$_5$O$_2$, 400; found, 400.4.

Example 35

(R)-2-(6-chloro-3-oxopyrrolo[4,3,2-de][2,6]naphthyridin-4(1H,3H,5H)-yl)-N-(4-cyanophenyl)-3-methylbutanamide

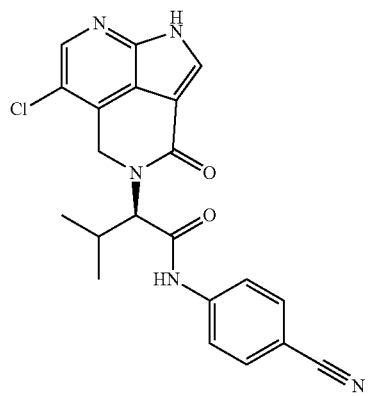 [SMILES: CC(C)[C@H](C(=O)Nc1ccc(C#N)cc1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), 4-aminobenzonitrile (7.68 mg, 0.065 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a yellow oil (2 mg, 15.1%). $^1$H NMR (400 MHz, CD$_3$OD) δ 0.90-1.03 (m, 3 H) 1.07-1.15 (m, 3 H) 2.59 (dt, J=11.24, 6.63 Hz, 1 H) 5.01 (d, J=19.45 Hz, 1 H) 5.21 (d, J=11.12 Hz, 1 H) 5.42 (d, J=19.45 Hz, 1 H) 7.64-7.66 (m, 1 H) 7.66-7.68 (m, 1 H) 7.80-7.82 (m, 1 H) 7.82-7.84 (m, 1 H) 7.86 (s, 1 H) 8.25 (s, 1 H). [M+H] calc'd for C$_{21}$H$_{18}$ClN$_5$O$_2$, 408; found, 408.4.

Example 36

(R)-2-(6-chloro-3-oxopyrrolo[4,3,2-de][2,6]naphthyridin-4(1H,3H,5H)-yl)-N-(3-cyanophenyl)-3-methylbutanamide

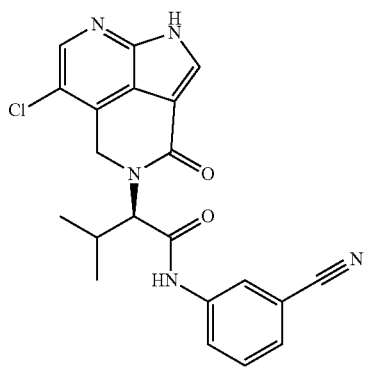 [SMILES: CC(C)[C@H](C(=O)Nc1cccc(C#N)c1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), 3-aminobenzonitrile (7.68 mg, 0.065 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a yellow oil (1.8 mg, 13.58%). $^1$H NMR (400 MHz, CD$_3$OD) δ 1.00 (d, J=6.60 Hz, 3 H) 1.12 (d, J=6.57 Hz, 3 H) 2.60 (s, 1 H) 5.02 (d, J=19.71 Hz, 1 H) 5.20 (d, J=11.12 Hz, 1 H) 5.43 (d, J=19.71 Hz, 1 H) 7.43 (dt, J=7.77, 1.42 Hz, 1 H) 7.48 (t, J=7.96 Hz, 1 H) 7.81-7.85 (m, 1 H) 7.86 (s, 1 H) 8.08 (t, J=1.64 Hz, 1 H) 8.25 (s, 1 H). [M+H] calc'd for C$_{21}$H$_{18}$ClN$_5$O$_2$, 408; found, 408.4.

Example 37

(R)-2-(6-chloro-3-oxopyrrolo[4,3,2-de][2,6]naphthyridin-4(1H,3H,5H)-yl)-N—((S)-1-cyanobutan-2-yl)-3-methylbutanamide

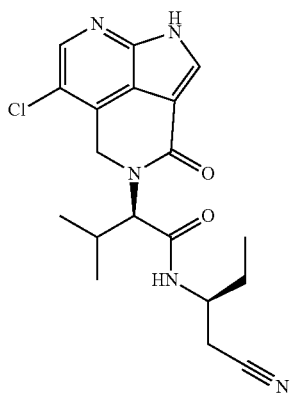 [SMILES: CC[C@@H](CC#N)NC(=O)[C@@H](C(C)C)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), (S)-3-aminopentanenitrile (3.19 mg, 0.032 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a yellow oil (3.1 mg, 24.6%). $^1$H NMR (400 MHz, CD$_3$OD) δ 0.93 (d, J=6.57 Hz, 3 H) 0.97 (t, J=7.33 Hz, 3 H) 1.07 (d, J=6.57 Hz, 3 H) 1.51-1.69 (m, 2 H) 2.44-2.58 (m, 2 H) 2.58-2.72 (m, 1 H) 4.07 (br. s., 1 H) 4.86-4.97 (m, 1 H) 5.08 (d, J=11.12 Hz, 1 H) 5.31 (d, J=19.71 Hz, 1 H) 7.84 (s, 1 H) 8.23 (s, 1 H). [M+H] calc'd for C$_{19}$H$_{22}$ClN$_5$O$_2$, 388; found, 388.4.

Example 38

(R)-2-(6-chloro-3-oxopyrrolo[4,3,2-de][2,6]naphthyridin-4(1H,3H,5H)-yl)-N—((R)-1-cyanobutan-2-yl)-3-methylbutanamide

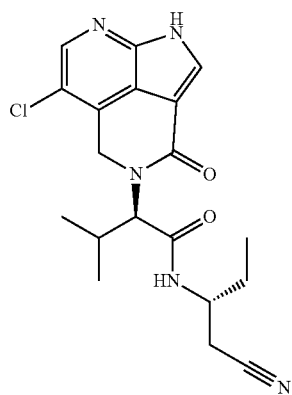 [SMILES: CC[C@H](CC#N)NC(=O)[C@@H](C(C)C)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), (R)-3-aminopentanenitrile (3.19 mg, 0.032 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a yellow oil (2.9 mg, 23.01%). $^1$H NMR (400 MHz, CD$_3$OD) δ 0.82 (t, J=7.45 Hz, 3 H) 0.89-0.99 (m, 3 H) 1.11 (d, J=6.57 Hz, 3 H) 1.44-1.68 (m, 2 H) 2.41-2.56 (m, 1 H) 2.63 (dd, J=16.93, 7.33 Hz, 1 H) 2.76 (dd, J=16.93, 5.05 Hz, 1 H) 3.99 (d, J=10.61 Hz, 1 H) 4.95 (d, J=19.96 Hz, 1 H) 5.05 (d, J=11.37 Hz, 1 H) 5.35 (d, J=19.71 Hz, 1 H) 7.85 (s, 1 H) 8.20-8.27 (m, 1 H). [M+H] calc'd for C$_{19}$H$_{22}$ClN$_5$O$_2$, 388; found, 388.4.

Example 39

(R)-1-(2-(6-chloro-3-oxopyrrolo[4,3,2-de][2,6]naphthyridin-4(1H,3H,5H)-yl)-3-methylbutanoyl)azetidine-3-carbonitrile

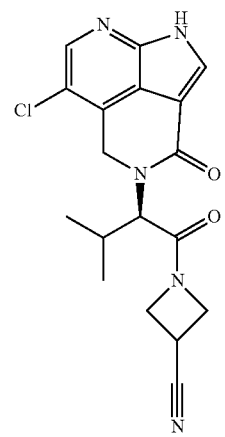 [SMILES: CC(C)[C@H](C(=O)N1CC(C#N)C1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3-methylbutanoic acid (10 mg, 0.032 mmol). THF (0.5 mL), azetidine-3-carbonitrile (2.7 mg, 0.032 mmol), 4-methylmorpholine (4.93 mg, 0.049 mmol) and HATU (14.83 mg, 0.039 mmol) were added and the solution was stirred at 25° C. for 1 h. The reaction mixture was purified via preparative mass trigger LC-MS (AcCN/H$_2$O, 5-50%). The fractions were collected, concentrated, and dried in vacuo to afford the title compound as a semi-solid (3.7 mg, 30.6%). $^1$H NMR (400 MHz, CD$_3$OD) δ 0.94 (t, J=6.32 Hz, 3 H) 1.07 (dd, J=18.19, 6.32 Hz, 3 H) 2.44-2.59 (m, 1 H) 3.47-3.79 (m, 1 H) 4.15-4.40 (m, 2 H) 4.57 (dt, J=9.73, 4.99 Hz, 1 H) 4.63-4.78 (m, 1 H) 4.84 (d, J=19.71 Hz, 1 H) 5.06-5.30 (m, 2 H) 7.82 (d, J=11.37 Hz, 1 H) 8.25 (d, J=5.56 Hz, 1 H). [M+H] calc'd for C$_{18}$H$_{18}$ClN$_5$O$_2$, 372; found, 372.4.

Preparation M:

(R)-2-(6-chloro-3-oxopyrrolo[4,3,2-de][2,6]naphthyridin-4(1H,3H,5H)-yl)-3,3-dimethylbutanoic acid

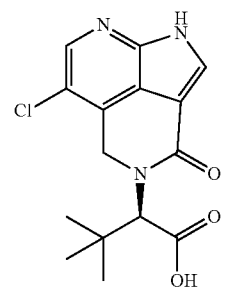 [SMILES: CC(C)(C)[C@H](C(=O)O)N1Cc2c(Cl)cnc3[nH]cc(c23)C1=O]

Step A: (R)-4-((1-(benzyloxy)-3,3-dimethyl-1-oxobutan-2-ylamino)methyl)-5-chloro-1-tosyl-1H-pyrrolo[2,3-b]pyridine-3-carboxylic acid

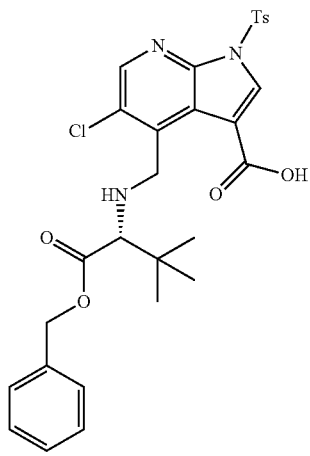 [SMILES: Cc1ccc(S(=O)(=O)n2cc(C(=O)O)c3c(CN[C@@H](C(=O)OCc4ccccc4)C(C)(C)C)c(Cl)cnc32)cc1]

To a 10 mL round bottom flask was added sodium triacetoxyborohydride (86 mg, 0.407 mmol), (R)-benzyl 2-amino-3,3-dimethylbutanoate (130 mg, 0.407 mmol) and DCM (2 mL). The mixture was stirred at room temperature for 10 min and then cooled to 0° C. 5-Chloro-4-formyl-1-tosyl-1H-pyrrolo[2,3-b]pyridine-3-carboxylic acid (130 mg, 0.271 mmol) was added and the reaction mixture was stirred at 0° C. for 20 min to afford the title compound. [M+H] calc'd for $C_{29}H_{30}ClN_3O_6S$, 584; found, 584.0.

Step B: (R)-benzyl 2-(6-chloro-3-oxo-1-tosylpyrrolo[4,3,2-de][2,6]naphthyridin-4(1H,3H,5H)-yl)-3,3-dimethylbutanoate

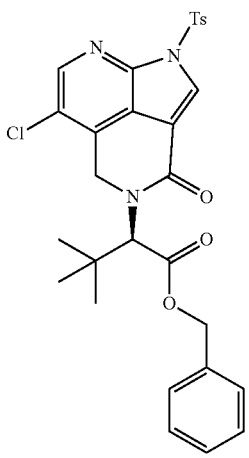 [SMILES: Cc1ccc(S(=O)(=O)n2cc3c4c(c(Cl)cnc42)CN([C@@H](C(=O)OCc2ccccc2)C(C)(C)C)C3=O)cc1]

Crude (R)-4-((1-(benzyloxy)-3,3-dimethyl-1-oxobutan-2-ylamino)methyl)-5-chloro-1-tosyl-1H-pyrrolo[2,3-b]pyridine-3-carboxylic acid was heated in HATU (124 mg, 0.326 mmol) and 4-methylmorpholine (82 mg, 0.814 mmol) at reflux for 3 h. The reaction mixture was subsequently concentrated and dried in vacuo to afford the title compound. [M+H] calc'd for $C_{29}H_{28}ClN_3O_5S$, 566; found, 566.0.

Step C: (R)-2-(6-chloro-3-oxopyrrolo[4,3,2-de][2,6]naphthyridin-4(1H,3H,5H)-yl)-3,3-dimethylbutanoic acid Crude (R)-benzyl 2-(6-chloro-3-oxo-1-tosylpyrrolo[4,3,2-de][2,6]naphthyridin-4(1H,3H,5H)-yl)-3,3-dimethylbutanoate was dissolved in MeOH/THF (50%, 5 mL). Aqueous NaOH (1N, 2 mL) was added. The reaction mixture was stirred at 50° C. for 16 h and was purified via preparative mass trigger LC-MS (AcCN/H₂O, 20-50%). The fractions were collected, concentrated, and dried in vacuo to afford the title compound as a yellow oil (34 mg, 38.9% from Step A starting material). $^1$H NMR (400 MHz, CD₃OD) δ 1.22-1.32 (m, 9 H) 4.92 (br. s., 1 H) 5.18 (d, J=18.95 Hz, 1 H) 5.33 (d, J=18.95 Hz, 1 H) 7.88 (s, 1 H) 8.29 (s, 1 H). [M+H] calc'd for $C_{15}H_{16}ClN_3O_3$, 322; found, 322.5.

Example 40

(R)-2-(6-chloro-3-oxopyrrolo[4,3,2-de][2,6]naphthyridin-4(1H,3H,5H)-yl)-N-(2-cyanoethyl)-3,3-dimethylbutanamide

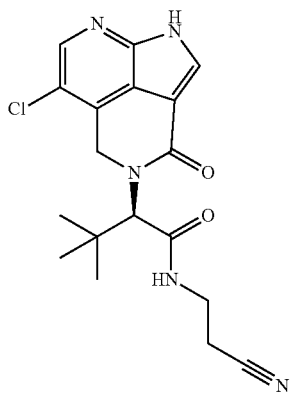 [SMILES: CC(C)(C)[C@H](C(=O)NCCC#N)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3,3-dimethylbutanoic acid (5 mg, 0.016 mmol). DMF (0.5 mL), 3-aminopropanenitrile (1.089 mg, 0.016 mmol), HOBt (3.57 mg, 0.023 mmol), EDC (4.47 mg, 0.023 mmol) and N,N-dimethylpyridin-4-amine (1.898 mg, 0.016 mmol) were added and the solution was stirred at 25° C. for 4 h. The reaction mixture was purified via preparative mass trigger LC-MS (AcCN/H₂O, 20-50%). The fractions were collected, concentrated, and dried in vacuo to afford the title compound as a yellow oil (3.2 mg, 55.1%). $^1$H NMR (500 MHz, CD₃OD) δ 1.19 (s, 9 H) 2.63-2.72 (m, 2 H) 3.38-3.53 (m, 2 H) 4.89 (br. s., 1 H) 5.29 (d, J=19.04 Hz, 1 H)

5.41 (d, J=19.00 Hz, 2 H) 7.85 (s, 1 H) 8.24 (s, 1 H) 8.55 (d, J=4.88 Hz, 1 H). [M+H] calc'd for C$_{18}$H$_{20}$ClN$_5$O$_2$, 374; found, 374.5.

Example 41

(R)-1-(2-(6-chloro-3-oxopyrrolo[4,3,2-de][2,6]naphthyridin-4(1H,3H,5H)-yl)-3,3-dimethylbutanoyl)azetidine-3-carbonitrile

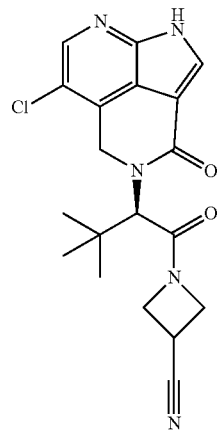 [SMILES: CC(C)(C)[C@H](C(=O)N1CC(C#N)C1)N1Cc2c(Cl)cnc3[nH]cc(c23)C1=O]

To an 8 mL scintillation vial equipped for stirring was added (R)-2-(6-chloro-3-oxopyrrolo[4,3,2-de][2,6]naphthyridin-4(1H,3H,5H)-yl)-3,3-dimethylbutanoic acid (25 mg, 0.078 mmol) under nitrogen. THF (0.5 mL), azetidine-3-carbonitrile hydrochloride (18.45 mg, 0.155 mmol), HATU and 4-methylmorpholine (11.79 mg, 0.117 mmol) were added and the solution was stirred at 25° C. for 1 h. The reaction mixture was purified via preparative mass trigger LC-MS (AcCN/H$_2$O, 15-40%). The fractions were collected, concentrated, and dried in vacuo to afford the title compound as a yellow semi-solid (4.1 mg, 13.7%). $^1$H NMR (400 MHz, CD$_3$OD) δ 1.17 (s, 9 H) 3.50-3.78 (m, 1 H) 4.17 (br. s., 1 H) 4.25-4.37 (m, 1 H) 4.41-4.69 (m, 2 H) 5.17-5.30 (m, 2 H) 5.44 (s, 1 H) 7.87 (br. s., 1 H) 8.25 (s, 1 H). [M+H] calc'd for C$_{19}$H$_{20}$ClN$_5$O$_2$, 386; found, 386.4.

Preparation N:

5-fluoro-4-formyl-1-tosyl-1H-pyrrolo[2,3-b]pyridine-3-carboxylic acid

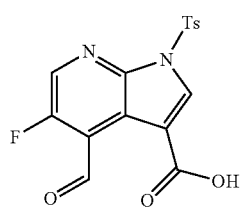 [SMILES: Cc1ccc(S(=O)(=O)n2cc(C(=O)O)c3c(C=O)c(F)cnc32)cc1]

Step A:
(5-fluoro-1H-pyrrolo[2,3-b]pyridin-4-yl)methanol

To an oven-dried 200 mL round bottom flask equipped for stirring was added methyl 5-fluoro-1H-pyrrolo[2,3-b]pyridine-4-carboxylate (2.4 g, 12.36 mmol) under nitrogen. THF (100 mL) was added and the colorless solution was cooled to 0° C. Lithium aluminum hydride (27.2 mL, 27.2 mmol) was added and the solution was stirred at 0° C. for 3 h. The reaction was quenched with EtOAc (100 mL); brine (100 mL) was added, and the aqueous phase was extracted three times with EtOAc. The organics were dried over Na$_2$SO$_4$ and concentrated to afford the title compound as a yellow fine powder (2.01 g, 98%). $^1$H NMR (400 MHz, CD$_3$OD) δ 4.96 (d, J=1.26 Hz, 2 H) 6.72 (d, J=3.54 Hz, 1 H) 7.44 (d, J=3.54 Hz, 1 H) 8.06 (d, J=2.78 Hz, 1 H). [M+H] calc'd for C$_8$H$_7$FN$_2$O, 167; found, 167.5.

Step B:
5-fluoro-1H-pyrrolo[2,3-b]pyridine-4-carbaldehyde

To a 250 mL round bottom flask equipped with a stirring bar was added (5-fluoro-1H-pyrrolo[2,3-b]pyridin-4-yl)methanol (2.01 g, 12.10 mmol) in THF (100 mL) under nitrogen. Manganese dioxide (10.52 g, 121 mmol) was added and the reaction mixture was stirred at 60° C. for 2 h. The organics were filtered through a pad of Celite, rinsed with EtOAc (100 mL) and concentrated. The resulting solid was triturated with EtOAc (50 mL) and filtered to give the title compound as a light yellow solid (1.3 g, 65.5%). $^1$H NMR (400 MHz, CD$_3$OD) δ 4.59 (s, 1 H) 5.34 (d, J=3.54 Hz, 1 H) 5.86-6.08 (m, 1 H) 6.58 (d, J=3.28 Hz, 1 H). [M+H] calc'd for C$_8$H$_5$FN$_2$O, 165; found, 165.5.

Step C: 5-fluoro-3-iodo-1H-pyrrolo[2,3-b]pyridine-4-carbaldehyde

To a solution of 5-fluoro-1H-pyrrolo[2,3-b]pyridine-4-carbaldehyde (2.45 g, 14.93 mmol) in EtOH (20 mL) was added iodine (4.55 g, 17.91 mmol), sodium iodide (2.68 g, 17.91 mmol) and aqueous NaOH (1N, 15 mL). The reaction mixture was stirred for 4 h at 25° C. and diluted with aqueous NaHSO₃ (0.1N). An orange precipitate was collected by filtration and dried under vacuum to afford the title compound as a yellow solid (6.54 g, 82%). [M+H] calc'd for $C_8H_4FIN_2O$, 291; found, 291.5.

Step D: 5-fluoro-3-iodo-1-tosyl-1H-pyrrolo[2,3-b]pyridine-4-carbaldehyde

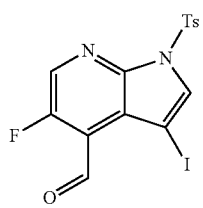

To a solution of 5-fluoro-3-iodo-1H-pyrrolo[2,3-b]pyridine-4-carbaldehyde in DMF (12 mL) was added NaOH (0.716 g, 17.91 mmol). The deep red solution was stirred for 30 min after which 4-methylbenzene-1-sulfonyl chloride (3.13 g, 16.42 mmol) was added. The reaction mixture was stirred for 2 h, subsequently diluted with EtOAc, and washed with water and brine. The extracts were dried over MgSO₄ and concentrated. Purification by silica column chromatography (DCM, 100%) afforded the title compound as light yellow solid (3.65 g, 55%). ¹H NMR (400 MHz, DMSO-d₆) δ 2.36 (s, 3 H) 7.45 (m, J=8.08 Hz, 2 H) 8.02 (m, J=8.34 Hz, 2 H) 8.42 (s, 1 H) 8.59 (d, J=2.53 Hz, 1 H) 11.13 (s, 1 H). [M+H] calc'd for $C_{15}H_{10}FIN_2O_3S$, 445; found, 445.1.

Step E: 5-fluoro-4-formyl-1-tosyl-1H-pyrrolo[2,3-b]pyridine-3-carboxylic acid

Lithium chloride (0.472 g, 11.14 mmol) and lithium formate (0.579 g, 11.14 mmol) were combined in a sealable dried tube. DMF (10 mL), 5-fluoro-3-iodo-1-tosyl-1H-pyrrolo[2,3-b]pyridine-4-carbaldehyde (1.650 g, 3.71 mmol), acetic anhydride (0.702 mL, 7.43 mmol) and diacetoxypalladium (0.083 g, 0.371 mmol) were added. N-Ethyl-N-isopropylpropan-2-amine (1.294 mL, 7.43 mmol) was added and the mixture was sealed and heated at 56° C. for 3 h. The reaction mixture was taken up in MeOH/DCM (20%) and filtered. The yellow solution was concentrated and the residue was dissolved in MeOH/DCM (10%) and washed with aqueous HCl (0.1N). The aqueous phase was extracted two more times. The organics were combined, dried over MgSO₄ and concentrated to an orange oil, which was triturated in ether (300 mL). The precipitate was filtered and dried in vacuo to afford the title compound as light yellow solid (1.15 g, 77%). ¹H NMR (400 MHz, DMSO-d₆) δ 2.37 (s, 3 H) 7.47 (d, J=8.08 Hz, 2 H) 8.10 (d, J=8.10 Hz, 2 H) 8.54-8.65 (m, 2 H) 10.60 (s, 1 H) 13.45 (br. s., 1 H). [M+H] calc'd for $C_{15}H_{10}FIN_2O_3S$, 363; found, 363.4.

Preparation O:

(R)-2-(6-fluoro-3-oxopyrrolo[4,3,2-de][2,6]naphthyridin-4(1H,3H,5H)-yl)-3-methylbutanoic acid

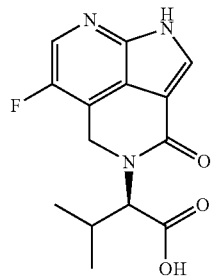 [SMILES: CC(C)[C@H](C(=O)O)N1Cc2c(F)cnc3[nH]cc(c23)C1=O]

Step A: (R)-4-((1-tert-butoxy-3-methyl-1-oxobutan-2-ylamino)methyl)-5-fluoro-1-tosyl-1H-pyrrolo[2,3-b]pyridine-3-carboxylic acid

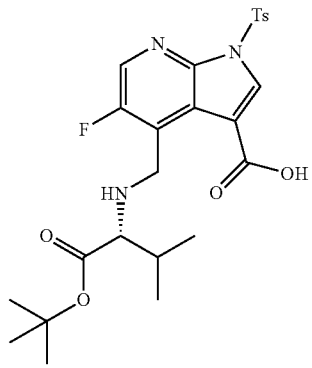 [SMILES: Cc1ccc(S(=O)(=O)n2cc(C(=O)O)c3c(CN[C@@H](C(=O)OC(C)(C)C)C(C)C)c(F)cnc32)cc1]

A mixture of sodium triacetoxyborohydride (1.143 g, 5.39 mmol), (R)-tert-butyl 2-amino-3-methylbutanoate hydrochloride (1.131 g, 5.39 mmol) and DCM (20 mL) was stirred at room temperature for 10 min. The reaction mixture was cooled to 0° C. 5-fluoro-4-formyl-1-tosyl-1H-pyrrolo[2,3-b]pyridine-3-carboxylate (1.299 g, 3.60 mmol) was added and the reaction was stirred at 0° C. for 20 min to afford the title compound. [M+H] calc'd for $C_{25}H_{30}FN_3O_6S$, 520; found, 520.2.

Step B: (R)-tert-butyl 2-(6-fluoro-3-oxo-1-tosylpyrrolo[4,3,2-de][2,6]naphthyridin-4(1H,3H,5H)-yl)-3-methylbutanoate

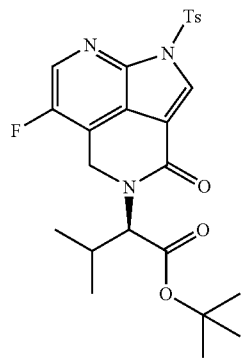 [SMILES: Cc1ccc(S(=O)(=O)n2cc3c4c(c(F)cnc42)CN([C@@H](C(=O)OC(C)(C)C)C(C)C)C3=O)cc1]

Crude (R)-4-((1-tert-butoxy-3-methyl-1-oxobutan-2-ylamino)methyl)-5-fluoro-1-tosyl-1H-pyrrolo[2,3-b]pyridine-3-carboxylic acid was heated in HATU (2.60 g, 7.19 mmol) and 4-methylmorpholine (1.091 g, 10.79 mmol) at reflux for 3 h. The reaction was incomplete by LC-MS. HATU (1.37 g, mmol, 3.79 mmol) and 4-methylmorpholine (1.091 g, 10.79 mmol) were added and the reaction mixture was stirred at reflux for 16 h. Following reaction, the mixture was washed with aqueous NaHCO₃ (sat.) and extracted with DCM. The organics were washed with brine, dried over Na₂SO₄, and concentrated to a brown oil. Purification by silica column chromatography (EtOAc/DCM, 0-20%) afforded the title compound as a white foam. (0.933 g, 51.7%). $^1$H NMR (400 MHz, DMSO-d$_6$) δ 0.80 (d, J=6.57 Hz, 3 H) 1.02 (d, J=6.57 Hz, 3 H) 1.39 (s, 9 H) 2.31-2.39 (m, 4 H) 4.77 (d, J=10.61 Hz, 1 H) 5.02 (d, J=7.58 Hz, 2 H) 7.46 (d, J=7.83 Hz, 2 H) 8.08 (d, J=8.34 Hz, 2 H) 8.29 (s, 1 H) 8.44 (d, J=2.78 Hz, 1 H). [M+H] calc'd for $C_{25}H_{28}FN_3O_5S$, 502; found, 502.3.

Step C: (R)-tert-butyl 2-(6-fluoro-3-oxopyrrolo[4,3,2-de][2,6]naphthyridin-4(1H,3H,5H)-yl)-3-methylbutanoate

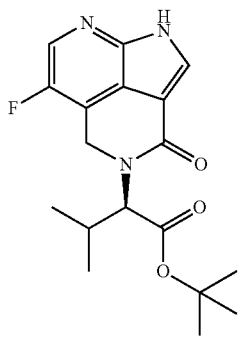 [SMILES: CC(C)[C@H](C(=O)OC(C)(C)C)N1Cc2c(F)cnc3[nH]cc(c23)C1=O]

To a stirred solution of (R)-tert-butyl 2-(6-fluoro-3-oxo-1-tosylpyrrolo[4,3,2-de][2,6]naphthyridin-4(1H,3H,5H)-yl)-3-methylbutanoate (933 mg, 1.860 mmol) in MeOH (4 mL) was added aqueous NaOH (1N, 2 mL). The reaction mixture was stirred at 25° C. for 40 min. The reaction was partitioned between DCM and brine. The organics were dried over MgSO₄ and concentrated. Purification by silica column chromatography (MeOH/DCM, 0-5%) afforded the title compound as a yellow oil (0.39 g, 60.4%). [M+H] calc'd for $C_{18}H_{22}FN_3O_3$, 348; found, 348.5.

Step D: (R)-2-(6-fluoro-3-oxopyrrolo[4,3,2-de][2,6]naphthyridin-4(1H,3H,5H)-yl)-3-methylbutanoic acid (R)-tert-Butyl 2-(6-fluoro-3-oxopyrrolo[4,3,2-de][2,6]naphthyridin-4(1H,3H,5H)-yl)-3-methylbutanoate was stirred in DCM/TFA (50%, 10 mL) for 1 h, concentrated and dried in vacuo to afford the title compound as a beige solid (0.32 g, 59.1%). $^1$H NMR (400 MHz, DMSO-d$_6$) δ 0.84 (d, J=6.30 Hz, 3 H) 1.04 (d, J=6.32 Hz, 3 H) 2.39 (dt, J=10.61, 6.57 Hz, 1 H) 4.83 (d, J=10.61 Hz, 1 H) 5.04 (d, J=9.60 Hz, 2 H) 7.98 (s, 1 H) 8.26 (s, 1 H) 12.39 (br. s., 1 H). [M+H] calc'd for $C_{14}H_{14}FN_3O_3$, 292; found, 292.5.

Example 42

(R)-1-(2-(6-fluoro-3-oxopyrrolo[4,3,2-de][2,6]naphthyridin-4(1H,3H,5H)-yl)-3-methylbutanoyl)azetidine-3-carbonitrile

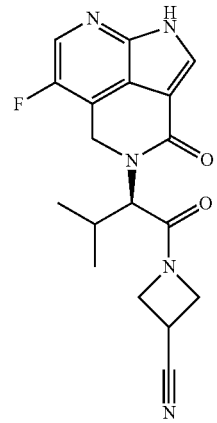 [SMILES: CC(C)[C@H](C(=O)N1CC(C#N)C1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (60 mg, 0.206 mmol). DMF (0.5 mL), azetidine-3-carbonitrile hydrochloride (0.309, 36.6 mg), HOBt (47.3 mg, 0.309 mmol), EDC (59.2 mg, 0.309 mmol) and N,N-dimethylpyridin-4-amine (37.7 mg, 0.309 mmol) were added and the solution was stirred at 25° C. for 4 h. The reaction mixture was purified via preparative mass trigger LC-MS (AcCN/H₂O, 20-50%). The fractions were collected, concentrated, and dried in vacuo to afford the title compound as a TFA salt. The residue was further purified using silica column chromatography (MeOH/DCM, 0-10%) which gave the title compound as a white solid (free base, 25.2 mg, 34.4%). $^1$H NMR (400 MHz, DMSO-d$_6$) δ 0.78 (dd, J=6.57, 3.79 Hz, 3 H) 0.95 (dd, J=13.01, 6.44 Hz, 3 H) 1.09 (t, J=6.95 Hz, 1 H) 3.53-3.86 (m, 1 H) 3.94-4.10 (m, 1 H) 4.10-4.29 (m, 2 H) 4.29-4.48 (m, 1 H) 4.87 (dd, J=18.82, 8.21 Hz, 1 H) 4.96-5.14 (m, 2 H) 7.99 (dd, J=5.43, 2.40 Hz, 1 H) 8.25 (t, J=2.78 Hz, 1 H) 12.39 (br. s., 1 H). [M+H] calc'd for $C_{18}H_{18}FN_5O_2$, 356; found, 356.5.

Example 43

(R)-2-(6-fluoro-3-oxopyrrolo[4,3,2-de][2,6]naphthyridin-4(1H,3H,5H)-yl)-3-methylbutanoic acid

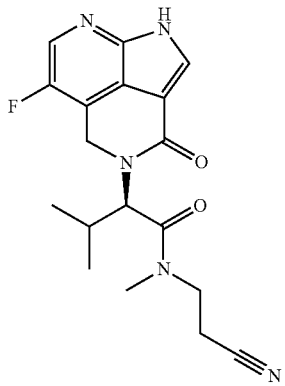 [SMILES: CC(C)[C@H](C(=O)N(C)CCC#N)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), 3-(methylamino)propanenitrile (0.077, 6.5 mg), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a yellow oil (6.1 mg, 33.1%). $^1$H NMR (400 MHz, CD$_3$OD) δ 0.79-0.93 (m, 3 H) 0.97-1.06 (m, 3 H) 2.49-2.67 (m, 1 H) 2.71-2.80 (m, 2 H) 3.00 (s, 1 H) 3.24 (s, 2 H) 3.57-4.02 (m, 2 H) 4.99 (s, 1 H) 5.08-5.22 (m, 1 H) 5.52-5.63 (m, 1 H) 7.80-7.96 (m, 1 H) 8.16 (d, J=3.03 Hz, 1 H). [M+H] calc'd for C$_{18}$H$_{20}$FN$_5$O$_2$, 358; found, 358.4.

Example 44

(2R)-2-(6-fluoro-3-oxopyrrolo[4,3,2-de][2,6]naphthyridin-4(1H,3H,5H)-yl)-3-methyl-N-(tetrahydrofuran-3-yl)butanamide

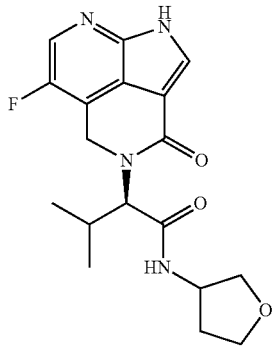 [SMILES: CC(C)[C@H](C(=O)NC1CCOC1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), tetrahydrofuran-3-amine (0.077, 6.7 mg), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (7.3 mg, 39.3%). $^1$H NMR (400 MHz, CD$_3$OD) δ 0.93 (d, J=6.57 Hz, 3 H) 1.04 (dd, J=6.57, 2.78 Hz, 3 H) 1.74-1.95 (m, 1 H) 2.21 (d, J=7.83 Hz, 1 H) 2.42-2.54 (m, 1 H) 3.50-3.67 (m, 1 H) 3.69-3.97 (m, 3 H) 4.37 (td, J=3.85, 1.89 Hz, 1 H) 4.96-5.12 (m, 2 H) 5.36-5.52 (m, 1 H) 7.86 (s, 1 H) 8.17 (d, J=3.28 Hz, 1 H). [M+H] calc'd for C$_{18}$H$_{21}$FN$_4$O$_3$, 361; found, 361.4.

Example 45

(R)-2-(6-fluoro-3-oxopyrrolo[4,3,2-de][2,6]naphthyridin-4(1H,3H,5H)-yl)-3-methyl-N-(1,1-dioxidotetrahydrothien-3-yl)butanamide

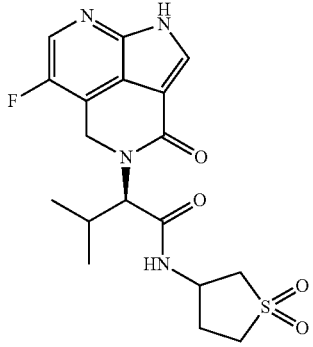 [SMILES: CC(C)[C@H](C(=O)NC1CCS(=O)(=O)C1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), 1,1-dioxidotetrahydrothien-3-ylamine (10.4 mg, 0.077), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (5.1 mg, 24.3%). $^1$H NMR (400 MHz, CD$_3$OD) δ 0.93 (dd, J=6.57, 1.26 Hz, 3 H) 1.05 (dd, J=6.32, 3.79 Hz, 3 H) 2.06-2.28 (m, 1 H) 2.40-2.59 (m, 2 H) 2.98 (td, J=12.57, 7.45 Hz, 1 H) 3.04-3.18 (m, 1 H) 3.21-3.29 (m, 1 H) 3.35-3.53 (m, 1 H) 4.51-4.66 (m, 1 H) 4.95-5.12 (m, 2 H) 5.40 (dd, J=19.20, 13.39 Hz, 1 H) 7.83-7.89 (m, 1 H) 8.17 (dd, J=3.28, 1.52 Hz, 1 H). [M+H] calc'd for C$_{18}$H$_{21}$FN$_4$O$_4$S, 409; found, 409.3.

Example 46

(R)-2-(6-fluoro-3-oxopyrrolo[4,3,2-de][2,6]naphthyridin-4(1H,3H,5H)-yl)-3-methyl-N-(2-(methylsulfonyl)ethyl)butanamide

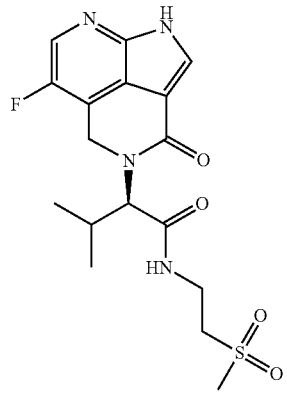 [SMILES: CC(C)[C@H](C(=O)NCCS(C)(=O)=O)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol) under nitrogen. DMF (0.5 mL), 2-(methylsulfonyl)ethanamine hydrochloride (8.2 mg, 0.051 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (8 mg, 39.2%). $^1$H NMR (400 MHz, CD$_3$OD) δ 0.91 (d, J=6.82 Hz, 3 H) 1.05 (d, J=6.32 Hz, 3 H) 2.50 (dq, J=17.94, 6.57 Hz, 1 H) 2.92 (s, 3 H) 3.22-3.28 (m, 1 H) 3.33-3.38 (m, 1 H) 3.61 (dt, J=14.40, 6.57 Hz, 1 H) 3.73 (dt, J=14.40, 6.57 Hz, 1 H) 4.94-5.13 (m, 2 H) 5.19-5.40 (m, 1 H) 7.85 (s, 1 H) 8.17 (d, J=3.28 Hz, 1 H). [M+H] calc'd for C$_{17}$H$_{21}$FN$_4$O$_4$S, 398; found, 398.3.

Preparation P:

(1,1-dioxo-hexahydro-6-thiopyran-4-yl)-amine hydrochloride

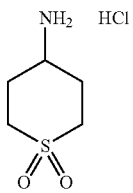

To a 100 mL round bottom flask equipped for stirring was added benzyl-(1,1-dioxo-hexahydro-6-thiopyran-4-yl)-amine (500 mg, 2.089 mmol) and palladium on carbon (111 mg, 1.045 mmol) under nitrogen. Methanol (15 mL) and aqueous HCl (4N, 0.172 mL, 2.089 mmol) were added and the solution was stirred at 60° C. for 48 h. The reaction mixture was filtered through Celite and concentrated to afford the title compound as an orange solid (241 mg, 62.1%). $^1$H NMR (400 MHz, DMSO-d$_6$) δ 1.88-2.12 (m, 2 H) 2.26 (d, J=11.87 Hz, 2 H) 3.08-3.22 (m, 2 H) 3.23-3.29 (m, 2 H) 3.39 (br. s., 1 H) 8.34 (br. s., 2 H).

Example 47

(R)—N-(1,1-dioxidotetrahydro-2H-thiopyran-4-yl)-2-(6-fluoro-3-oxopyrrolo[4,3,2-de][2,6]naphthyridin-4(1H,3H,5H)-yl)-3-methylbutanamide

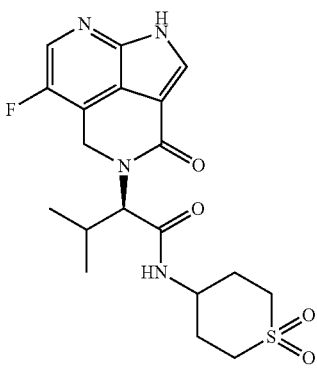 [SMILES: CC(C)[C@H](C(=O)NC1CCS(=O)(=O)CC1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol) under nitrogen. DMF (0.5 mL), (1,1-dioxo-hexahydro-6-thiopyran-4-yl)-amine hydrochloride (10 mg, 0.051 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a yellow oil (6.4 mg, 29.4%). $^1$H NMR (500 MHz, CD$_3$OD) δ 0.93 (d, J=6.83 Hz, 3 H) 1.04 (dd, J=6.35, 2.93 Hz, 3 H) 1.61-1.80 (m, 1 H) 1.89-2.01 (m, 1 H) 2.06-2.30 (m, 4 H) 2.36-2.54 (m, 2 H) 3.32-3.38 (m, 1 H) 4.19-4.38 (m, 1 H) 4.93-5.11 (m, 2 H) 5.45 (dd, J=18.79, 5.13 Hz, 1 H) 7.86 (s, 1 H) 8.17 (d, J=2.93 Hz, 1 H). [M+H] calc'd for C$_{19}$H$_{23}$FN$_4$O$_4$S, 423; found, 423.3.

Example 48

4-{(1R)-1-[(1,1-dioxidothiomorpholin-4-yl)carbonyl]-2-methylpropyl}-6-fluoro-4,5-dihydropyrrolo[4,3,2-de][2,6]naphthyridin-3(1H)-one

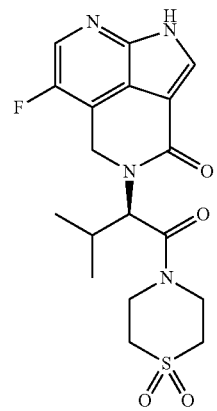 [SMILES: CC(C)[C@H](C(=O)N1CCS(=O)(=O)CC1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), thiomorpholine 1,1-dioxide hydrochloride (8.84 mg, 0.51 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (9.8 mg, 46.6%). $^1$H NMR (400 MHz, CD$_3$OD) δ 0.92 (d, J=6.82 Hz, 3 H) 1.02 (d, J=6.32 Hz, 3 H) 2.60 (dt, J=10.61, 6.57 Hz, 1 H) 2.90-3.03 (m, 1 H) 3.03-3.25 (m, 3 H) 3.86-4.01 (m, 1 H) 4.13 (ddd, J=14.78, 8.59, 2.40 Hz, 1 H) 4.21-4.41 (m, 2 H) 4.92-5.06 (m, 1 H) 5.06-5.18 (m, 1 H) 5.57 (d, J=10.61 Hz, 1 H) 7.89 (s, 1 H) 8.18 (d, J=3.28 Hz, 1 H). [M+H] calc'd for C$_{18}$H$_{21}$FN$_4$O$_4$S, 409; found, 409.3.

Example 49

(R)—N-(cyclopropylmethoxy)-2-(6-fluoro-3-oxopyrrolo[4,3,2-de][2,6]naphthyridin-4(1H,3H,5H)-yl)-3-methylbutanamide

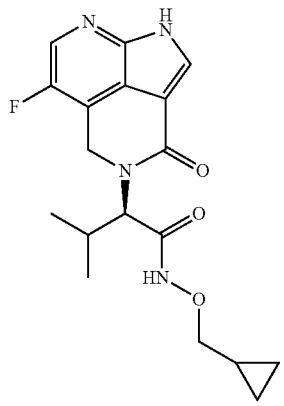 [SMILES: CC(C)[C@H](C(=O)NOCC1CC1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), O-(cyclopropylmethyl)hydroxylamine hydrochloride (6.4 mg, 0.051 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (5 mg, 23%). $^1$H NMR (400 MHz, CD$_3$OD) δ 0.16-0.24 (m, 2 H) 0.39-0.55 (m, 2 H) 0.93 (d, J=6.57 Hz, 3 H) 1.05 (d, J=6.32 Hz, 3 H) 1.06-1.15 (m, 1 H) 2.53 (dt, J=11.24, 6.51 Hz, 1 H) 3.55-3.73 (m, 2 H) 4.94 (d, J=11.37 Hz, 1 H) 5.07 (d, J=19.20 Hz, 1 H) 5.46 (d, J=18.44 Hz, 1 H) 7.86 (s, 1 H) 8.17 (d, J=3.28 Hz, 1 H). [M+H] calc'd for C$_{18}$H$_{21}$FN$_4$O$_3$, 361; found, 361.4.

Preparation Q:

3,3-difluorocyclopentanamine

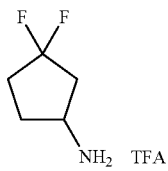

Step A: tert-butyl 3,3-difluorocyclopentylcarbamate

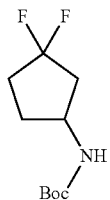

Deoxofluor™ (0.658 mL, 5.02 mmol) was added dropwise to a solution of tert-butyl 3-oxocyclopentylcarbamate (0.5 g, 2.509 mmol) in DCM (12 mL) at 0° C. After complete addition, the reaction mixture was allowed to warm up to room temperature and was stirred for 18 h. The reaction mixture was poured slowly into ice-cold aqueous NaHCO$_3$ (sat.). The aqueous layer was extracted 3 times with DCM. The combined organic layers were dried over MgSO$_4$, concentrated, and dried in vacuo. Purification by silica column chromatography (MeOH/DCM, 0-5%) afforded the title compound as a yellow oil (0.52 g, 94%).

Step B: 3,3-difluorocyclopentanamine

A mixture of tert-butyl 3,3-difluorocyclopentylcarbamate and DCM/TFA (50%, 7 mL) was stirred at 25° C. for 30 min. The reaction mixture was concentrated down and dried in vacuo to afford the title compound as an orange semi-solid, TFA salt (0.51 g, 99%). $^1$H NMR (400 MHz, DMSO-d$_6$) δ 1.69-1.88 (m, 1 H) 2.00-2.22 (m, 3 H) 2.22-2.38 (m, 1 H) 2.56 (d, J=6.32 Hz, 1 H) 3.71 (d, J=5.31 Hz, 1 H) 8.20 (br. s., 3 H).

Example 50

(2R)—N-(3,3-difluorocyclopentyl)-2-(6-fluoro-3-oxopyrrolo[4,3,2-de][2,6]naphthyridin-4(1H,3H,5H)-yl)-3-methylbutanamide

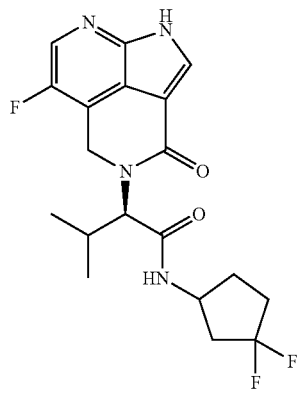 [SMILES: CC(C)[C@H](C(=O)NC1CCC(F)(F)C1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol) under nitrogen. DMF (0.5 mL), 3,3-difluorocyclopentanamine (11.2 mg, 0.051 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a brown oil (8 mg, 39.4%). $^1$H NMR (500 MHz, CD$_3$OD) δ 0.93 (d, J=6.83 Hz, 3 H) 1.04 (dd, J=6.35, 2.93 Hz, 3 H) 1.62-1.80 (m, 1 H) 1.87-2.02 (m, 1 H) 2.14-2.28 (m, 2 H) 2.35-2.58 (m, 2 H) 3.35 (s, 1 H) 4.22-4.35 (m, 1 H) 4.94-5.10 (m, 2 H) 5.45 (dd, J=18.79, 5.13 Hz, 1 H) 7.86 (s, 1 H) 8.17 (d, J=2.93 Hz, 1 H). [M+H] calc'd for C$_{19}$H$_{21}$F$_3$N$_4$O$_2$, 395; found, 395.4.

Preparation R:

3-(fluoromethyl)azetidine-3-carbonitrile, TFA salt

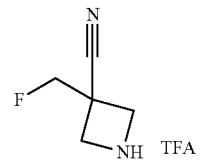

STEP A: tert-butyl 3-cyano-3-(fluoromethyl)azetidine-1-carboxylate

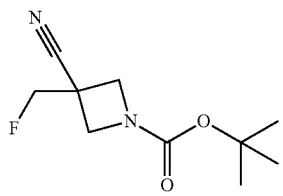

To an oven-dried 25 mL round bottom flask equipped for stirring was added diisopropylamine (0.659 mL, 4.66 mmol) under nitrogen. THF (5 mL) was added and the colorless solution was cooled to 0° C. To this solution was added n-BuLi (2.92 mL, 4.66 mmol) and the solution was stirred at 0° C. for 30 min. The solution was cooled to −78° C. and a solution of tert-butyl 3-cyanoazetidine-1-carboxylate (0.5 g, 2.74 mmol) in THF (3 mL) was added and the solution was stirred at −78° C. for 30 min. Bromofluoromethane (0.403 g, 3.57 mmol) was added at −78° C. dropwise. The reaction mixture was stirred for 30 min and then allowed to warm to 25° C. and stirred for 16 h. The reaction mixture was quenched at 0° C. with aqueous NH$_4$Cl (5 mL) and extracted with DCM (3×). The extracts were dried over Na$_2$SO$_4$. Purification by silica column chromatography (MeOH/DCM, 0-5%) afforded the title compound as a yellow oil (0.52 g, 94%).

Step B: 3-(fluoromethyl)azetidine-3-carbonitrile, TFA salt

A mixture of tert-butyl 3-cyano-3-(fluoromethyl)azetidine-1-carboxylate and DCM/TFA (50%, 5 mL) at 25° C. for 30 min. The reaction mixture was concentrated and dried under high vacuum to afford the title compound as an orange semi solid (145 mg, 0.687 mmol, 25%). $^1$H NMR (400 MHz, CDCl$_3$) δ 1.47 (dd, J=5.05, 2.02 Hz, 9 H) 4.03 (br. s., 2 H) 4.29 (br. s., 2 H) 4.62 (br. s., 1 H) 4.73 (br. s., 1 H).

Example 51

(R)-3-(fluoromethyl)-1-(3-methyl-2-(3-oxopyrrolo[4,3,2-de][2,6]naphthyridin-4(1H,3H,5H)-yl)butanoyl)azetidine-3-carbonitrile

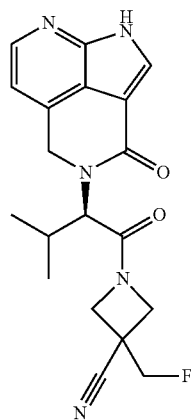 [SMILES: CC(C)[C@H](C(=O)N1CC(C#N)(CF)C1)N1Cc2ccnc3[nH]cc(c23)C1=O]

To an 8 mL scintillation vial equipped for stirring was added (R)-3-methyl-2-(3-oxopyrrolo[4,3,2-de][2,6]naphthyridin-4(1H,3H,5H)-yl)butanoic acid (80 mg, 0.293 mmol) under nitrogen. DMF (0.5 mL), 3-(fluoromethyl)azetidine-3-carbonitrile (93 mg, 0.439 mmol), HOBt (67.2 mg, 0.439 mmol), EDC (84 mg, 0.439 mmol) and N,N-dimethylpyridin-4-amine (53.6 mg, 0.439 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (34.5 mg, 25.3%). $^1$H NMR (400 MHz, DMSO-d$_6$) δ 0.78 (dd, J=6.57, 3.79 Hz, 3 H) 0.97 (dd, J=12.88, 6.32 Hz, 3 H) 2.30-2.41 (m, 1 H) 3.99 (dd, J=9.98, 4.42 Hz, 1 H) 4.22 (d, J=9.35 Hz, 2 H) 4.36 (s, 1 H) 4.62-4.71 (m, 1 H) 4.76-4.88 (m, 2 H) 4.87-5.03 (m, 1 H) 5.02-5.09 (m, 1 H) 7.09 (t, J=4.80 Hz, 1 H) 7.88 (dd, J=5.56, 2.27 Hz, 1 H) 8.27 (t, J=5.31 Hz, 1 H) 12.25 (d, J=8.84 Hz, 1 H). [M+H] calc'd for C$_{19}$H$_{20}$FN$_5$O$_2$, 370; found, 370.5.

Preparation S: 3-cyano-3-methylazetidine, TFA salt

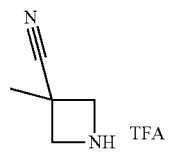

Step A: tert-butyl 3-cyano-3-methylazetidine-1-carboxylate

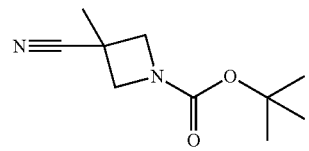

To an oven-dried 25 mL round bottom flask equipped for stirring was added diisopropylamine (1.318 mL, 9.33 mmol) under nitrogen. THF (10 mL) was added and the colorless solution was cooled to 0° C. n-BuLi in hexanes (1.6N, 5.83 mL, 9.33 mmol) was added dropwise and the solution was stirred at 0° C. for 30 min. The solution was cooled to −78° C. and a solution of tert-butyl 3-cyanoazetidine-1-carboxylate (1 g, 5.49 mmol) in THF (3 mL) was added and the solution was stirred at −78° C. for 30 min. Iodomethane (0.445 mL, 7.13 mmol) was added dropwise at −78° C. The reaction mixture was stirred for 30 min; it was then allowed to slowly warm up to 25° C. and was stirred for 16 h. The reaction mixture was quenched at 0° C. with aqueous ammonium chloride (5 mL) and was extracted with DCM (3 times). The extracts were dried over Na$_2$SO$_4$. Purification by silica column chromatography (MeOH/DCM, 0-5%) afforded the title compound as a yellow oil (0.35 g, 32%). $^1$H NMR (500 MHz, CDCl$_3$) δ 1.45 (s, 9 H) 1.67 (s, 3 H) 3.80 (d, J=8.30 Hz, 2 H) 4.29 (d, J=8.79 Hz, 2 H).

Step B: 3-cyano-3-methylazetidine, TFA salt

A mixture of tert-butyl 3-cyano-3-methylazetidine-1-carboxylate (0.345 g, 1.758 mmol) and DCM/TFA (50%, 7 mL) was stirred at 25° C. for 30 min. The reaction mixture was concentrated and dried in vacuo to afford the title compound as an orange semi-solid (0.22 g, 1.139 mmol, 64.8%). $^1$H NMR (400 MHz, DMSO-d$_6$) δ 1.65 (s, 3 H) 3.92 (d, J=11.12 Hz, 2 H) 4.34 (d, J=11.12 Hz, 2 H) 9.23 (br. s., 2 H).

Example 52

(R)-1-(2-(6-fluoro-3-oxopyrrolo[4,3,2-de][2,6]naphthyridin-4(1H,3H,5H)-yl)-3-methylbutanoyl)-3-methylazetidine-3-carbonitrile

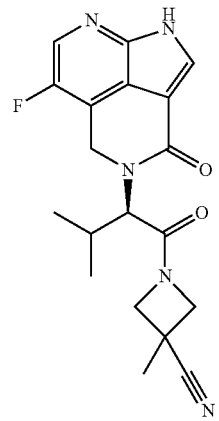 [SMILES: CC(C)[C@H](C(=O)N1CC(C)(C#N)C1)N1Cc2c(F)cnc3[nH]cc(c23)C1=O]

To an 8 mL scintillation vial equipped for stirring was added (R)-2-(6-fluoro-3-oxopyrrolo[4,3,2-de][2,6]naphthyridin-4(1H,3H,5H)-yl)-3-methylbutanoic acid (15 mg, 0.051 mmol). DMF (0.5 mL), 3-cyano-3-methylazetidine (15 mg, 0.077 mmol), HOBt (11.83 mg, 0.077 mmol), EDC (14.81 mg, 0.077 mmol) and N,N-dimethylpyridin-4-amine (9.44 mg, 0.077 mmol) were added and the solution was stirred at 25° C. for 4 h. The reaction mixture was purified via preparative mass trigger LC-MS (AcCN/H$_2$O, 20-50%). The fractions were collected and lyophilized to afford the title compound as a white solid (9 mg, 47.3%). $^1$H NMR (400 MHz, DMSO-d$_6$) δ 0.79 (dd, J=6.69, 2.91 Hz, 3 H) 0.96 (dd, J=9.09, 6.57 Hz, 3 H) 1.41-1.73 (m, 3 H) 2.26-2.44 (m, 1 H) 3.85 (dd, J=15.66, 9.85 Hz, 1 H) 4.06 (d, J=9.35 Hz, 2 H) 4.61 (s, 1 H) 4.88 (dd, J=19.20, 6.82 Hz, 1 H) 5.03 (d, J=11.12 Hz, 1 H) 5.07-5.18 (m, 1 H) 7.99 (t, J=3.16 Hz, 1 H) 8.25 (t, J=2.65 Hz, 1 H) 12.40 (br. s., 1 H). [M+H] calc'd for C$_{19}$H$_{20}$FN$_5$O$_2$, 370; found, 370.5

Example 53

(R)-3-methyl-1-(3-methyl-2-(3-oxopyrrolo[4,3,2-de][2,6]naphthyridin-4(1H,3H,5H)-yl)butanoyl)azetidine-3-carbonitrile

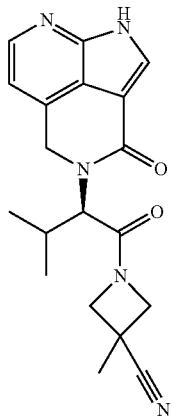 [SMILES: CC(C)[C@H](C(=O)N1CC(C)(C#N)C1)N1Cc2ccnc3[nH]cc(c23)C1=O]

To an 8 mL scintillation vial equipped for stirring was added (R)-3-methyl-2-(3-oxopyrrolo[4,3,2-de][2,6]naphthyridin-4(1H,3H,5H)-yl)butanoic acid (80 mg, 0.293 mmol). DMF (0.5 mL), 3-cyano-3-methylazetidine (85 mg, 0.439 mmol), HOBt (67.2 mg, 0.439 mmol), EDC (84 mg, 0.439 mmol) and N,N-dimethylpyridin-4-amine (53.6 mg, 0.439 mmol) were added and the solution was stirred at 25° C. for 4 h. The fractions were collected and lyophilized to afford the title compound as a white solid (31.5 mg, 30.6%). $^1$H NMR (400 MHz, DMSO-d$_6$) δ 0.78 (dd, J=6.82, 3.28 Hz, 3 H) 0.96 (dd, J=8.59, 6.32 Hz, 3 H) 1.44-1.68 (m, 3 H) 2.26-2.44 (m, 1 H) 3.84 (dd, J=9.47, 5.18 Hz, 1 H) 3.99-4.14 (m, 1 H) 4.21 (dd, J=9.47, 5.68 Hz, 1 H) 4.34-4.65 (m, 1 H) 4.85 (dd, J=19.45, 5.56 Hz, 1 H) 4.96-5.11 (m, 2 H) 7.08 (d, J=5.05 Hz, 1 H) 7.86 (d, J=4.04 Hz, 1 H) 8.26 (dd, J=4.80, 3.28 Hz, 1 H) 12.22 (br. s., 1 H). [M+H] calc'd for C$_{19}$H$_{21}$N$_5$O$_2$, 352; found, 352.5.

PREPARATION T: (R)-2-((3-(methoxycarbonyl)-1H-pyrrolo[2,3-b]pyridin-4-yl)methylamino)butanoic acid compound with 2,2,2-trifluoroacetic acid (1:1)

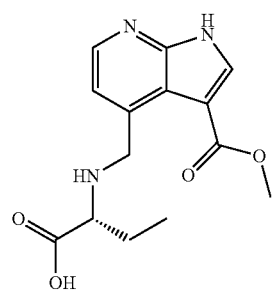 [SMILES: CC[C@@H](NCc1ccnc2[nH]cc(C(=O)OC)c12)C(=O)O]

STEP A: (R)-1-tert-butyl 3-methyl 4-((1-tert-butoxy-1-oxobutan-2-ylamino)methyl)-1H-pyrrolo[2,3-b]pyridine-1,3-dicarboxylate

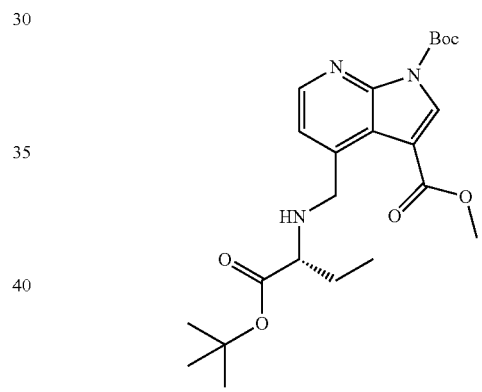

Sodium triacetoxyborohydride (9.86 mmol) and (R)-tert-butyl 2-aminobutanoate hydrochloride (5.59 mmol) were added to a 100 mL round bottom flask, followed by DCE (20 mL). The reaction mixture was stirred at room temperature for 30 min and cooled to 0° C. A solution of 1-tert-butyl 3-methyl 4-formyl-1H-pyrrolo[2,3-b]pyridine-1,3-dicarboxylate (3.29 mmol) in DCE (20 mL) was added. The reaction mixture was stirred at 0° C. for 30 min and at room temperature for 3 h. Purification by silica column chromatography (EtOAc/DCM, 0-10%) afforded the title compound as a yellow oil (1.4 g, 95%). [M+H] calc'd for C$_{23}$H$_{33}$N$_3$O$_6$, 448; found, 448.6.

STEP B: (R)-2-((3-(methoxycarbonyl)-1H-pyrrolo[2,3-b]pyridin-4-yl)methylamino)butanoic acid compound with 2,2,2-trifluoroacetic acid (1:1)

To a 100 mL round bottom flask equipped for stirring was added (R)-1-tert-butyl 3-methyl 4-((1-tert-butoxy-1-oxobutan-2-ylamino)methyl)-1H-pyrrolo[2,3-b]pyridine-1,3-dicarboxylate (1.45 g, 3.24 mmol) and DCM (10 mL). TFA (10 mL) was added and the reaction mixture was stirred at room temperature for 30 min. The reaction mixture was concentrated and dried in vacuo to afford the title compound as a yellow oil (1.3 g, 99%) (TFA salt). [M+H] calc'd for C$_{14}$H$_{17}$N$_3$O$_4$, 292; found, 292.6.

Examples 54 to 74

Compounds in Examples 54 to 74 were made in accordance with the following General Procedure A.

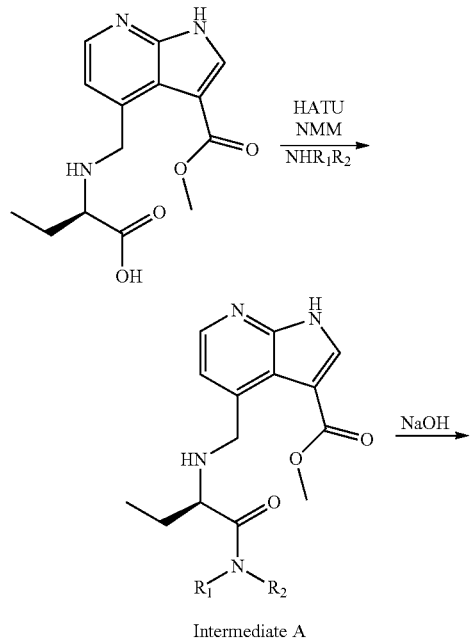

Intermediate A

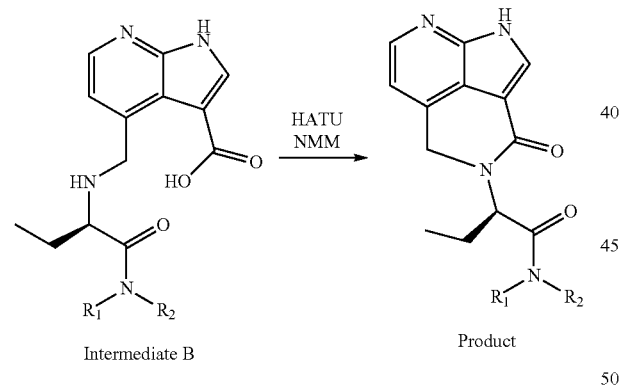

Intermediate B    Product

To an 8 mL scintillation vial equipped for stirring was added (R)-2-((3-(methoxycarbonyl)-1H-pyrrolo[2,3-b]pyridin-4-yl)methylamino)butanoic acid (43.4 mg, 0.149 mmol) and HATU (68.0 mg, 0.179 mmol). THF (2 mL), 4-methylmorpholine (0.049 mL, 0.447 mmol) and an appropriate amine, NHR$_1$R$_2$ (0.447 mmol) were added. The suspension was stirred at room temperature for 4 h and then concentrated to afford crude intermediate A, which was subsequently redissolved in MeOH (1 mL). Aqueous NaOH (12N, 2 mL) was added and the reaction mixture was stirred at 53° C. for 16 h. This residue was purified via preparative mass trigger LC-MS (AcCN/H$_2$O, 1-50%). The fractions were collected, concentrated, and dried in vacuo to afford intermediate B, which was cyclized in a mixture of THF (2 mL), HATU (68.0 mg, 0.179 mmol) and 4-methylmorpholine (0.049 mL, 0.447 mmol) at room temperature for 4 to 16 h. The product was purified via preparative mass trigger LC-MS (AcCN/H$_2$O, 1-50%). The fractions were collected, concentrated, and dried in vacuo to afford the title compound.

Example 54

(R)-4-(1-morpholino-1-oxobutan-2-yl)-4,5-dihydropyrrolo[4,3,2-de][2,6]naphthyridin-3(1 H)-one

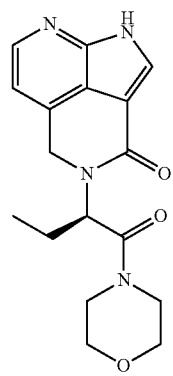 [SMILES: CC[C@H](C(=O)N1CCOCC1)N1Cc2ccnc3[nH]cc(c23)C1=O]

The title compound was prepared in accordance with General Procedure A, using morpholine as the amine, NHR$_1$R$_2$ (2.1 mg, 4.2% for 3 steps). $^1$H NMR (400 MHz, CD$_3$OD) δ 0.96 (t, J=7.45 Hz, 3 H) 1.99-2.13 (m, 2 H) 3.43-3.51 (m, 1 H) 3.53-3.62 (m, 2 H) 3.62-3.73 (m, 4 H) 5.06 (d, J=10.86 Hz, 2 H) 5.66-5.78 (m, 1 H) 7.21 (d, J=5.31 Hz, 1 H) 7.86 (s, 1 H) 8.32 (d, J=5.31 Hz, 1 H). [M+H] calc'd for C$_{17}$H$_{20}$N$_4$O$_3$, 329; found, 329.6.

Example 55

(R)-4-(1-(4-methylpiperazin-1-yl)-1-oxobutan-2-yl)-4,5-dihydropyrrolo[4,3,2-de][2,6]naphthyridin-3(1 H)-one

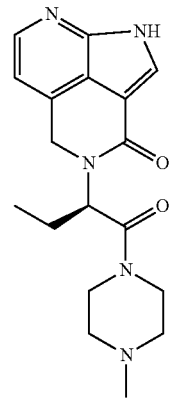 [SMILES: CC[C@H](C(=O)N1CCN(C)CC1)N1Cc2ccnc3[nH]cc(c23)C1=O]

The title compound was prepared in accordance with General Procedure A, using 1-methylpiperazine as the amine, NHR$_1$R$_2$ (3.2 mg, 6.3% for 3 steps). $^1$H NMR (400 MHz, CD$_3$OD) δ -0.52 (t, J=7.33 Hz, 3 H) 0.42-0.60 (m, 2 H) 1.33 (s, 3 H) 1.43 (d, J=12.88 Hz, 3 H) 1.58-1.74 (m, 1 H) 1.84-1.93 (m, 3 H) 1.93-2.05 (m, 2 H) 4.28 (s, 1 H) 5.64 (d, J=5.31

Hz, 1H) 6.34 (s, 1 H) 6.81 (d, J=5.05 Hz, 1 H). [M+H] calc'd for $C_{18}H_{23}N_5O_2$, 342; found, 342.6.

Example 56

4-((2R)-1-(3-hydroxypyrrolidin-1-yl)-1-oxobutan-2-yl)-4,5-dihydropyrrolo[4,3,2-de][2,6]naphthyridin-3(1H)-one

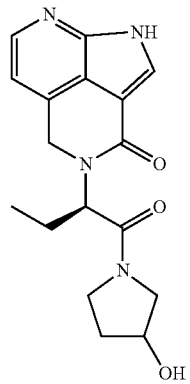 [SMILES: CC[C@H](C(=O)N1CCC(O)C1)N1Cc2ccnc3[nH]cc(c23)C1=O]

The title compound was prepared in accordance with General Procedure A, using 1-pyrrolidin-3-ol as the amine, $NHR_1R_2$ (16 mg, 32.7%, 3 steps). $^1$H NMR (400 MHz, $CD_3OD$) δ 0.90-1.08 (m, 3 H) 1.82-2.12 (m, 4 H) 2.91 (s, 1 H) 3.41-3.67 (m, 2 H) 3.74 (t, J=11.60 Hz, 2H) 4.28-4.50 (m, 1 H) 4.85-4.98 (m, 2 H) 7.13 (d, J=5.31 Hz, 1 H) 7.81 (t, J=3.41 Hz, 1 H) 8.28 (d, J=5.81 Hz, 1 H). [M+H] calc'd for $C_{17}H_{20}N_4O_3$, 329; found, 329.6.

Example 57

(R)—N-cyclopentyl-2-(3-oxopyrrolo[4,3,2-de][2,6]naphthyridin-4(1H,3H,5H)-yl)butanamide

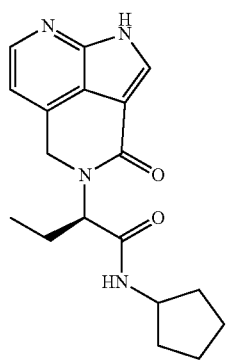 [SMILES: CC[C@H](C(=O)NC1CCCC1)N1Cc2ccnc3[nH]cc(c23)C1=O]

The title compound was prepared in accordance with General Procedure A, using cyclopentanamine as $NHR_1R_2$ (6.3 mg, 13%, 3 steps). $^1$H NMR (400 MHz, $CD_3OD$) δ 0.98 (q, J=7.50 Hz, 3 H) 1.38-1.52 (m, 2 H) 1.52-1.63 (m, 2 H) 1.63-1.79 (m, 2 H) 1.80-2.01 (m, 2H) 2.12-2.17 (m, 2 H) 3.99-4.19 (m, 1 H) 5.23 (dd, J=9.35, 6.82 Hz, 1 H) 5.27-5.37 (m, 1 H) 5.48 (s, 2 H) 7.23 (d, J=5.56 Hz, 1 H) 7.85 (s, 1 H) 8.32 (d, J=5.56 Hz, 1 H). [M+H] calc'd for $C_{18}H_{22}N_4O_2$, 327; found, 327.6.

Example 58

4-((2R)-1-(3-(4-fluorophenyl)pyrrolidin-1-yl)-1-oxobutan-2-yl)-4,5-dihydropyrrolo[4,3,2-de][2,6]naphthyridin-3(1H)-one

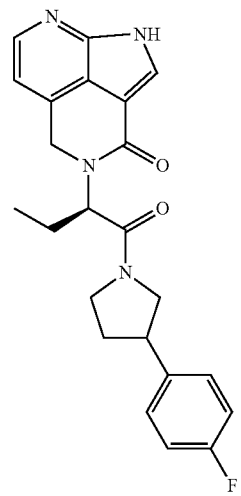 [SMILES: CC[C@H](C(=O)N1CCC(c2ccc(F)cc2)C1)N1Cc2ccnc3[nH]cc(c23)C1=O]

The title compound was prepared in accordance with General Procedure A, using 3-(4-fluorophenyl)pyrrolidine as the amine, $NHR_1R_2$ (14 mg, 23.1%, 3 steps). $^1$H NMR (400 MHz, $CD_3OD$) δ 0.89-1.06 (m, 3 H) 1.80 (s, 2 H) 2.19-2.39 (m, 2 H) 3.33-3.55 (m, 2 H) 3.56-3.65 (m, 1 H) 3.68-3.83 (m, 1 H) 3.84-3.96 (m, 1 H) 3.98-4.24 (m, 1 H) 5.03-5.35 (m, 2 H) 6.68-6.83 (m, 1 H) 6.86-6.99 (m, 1 H) 6.99-7.09 (m, 2 H) 7.10-7.37 (m, 1 H) 7.78-7.95 (m, 1 H) 8.34 (d, J=5.31 Hz, 1 H). [M+H] calc'd for $C_{23}H_{23}FN_4O_2$, 407; found, 407.6.

Example 59

4-((2R)-1-(3-(dimethylamino)pyrrolidin-1-yl)-1-oxobutan-2-yl)-4,5-dihydropyrrolo[4,3,2-de][2,6]naphthyridin-3(1H)-one

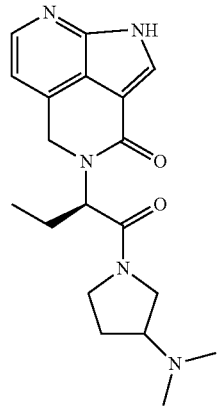 [SMILES: CC[C@H](C(=O)N1CCC(N(C)C)C1)N1Cc2ccnc3[nH]cc(c23)C1=O]

The title compound was prepared in accordance with General Procedure A, using N,N-dimethylpyrrolidin-3-amine as NHR₁R₂ (20 mg, 37.8%, 3 steps). ¹H NMR (400 MHz, CD₃OD) δ 0.87-1.05 (m, 3 H) 1.88-2.12 (m, 2 H) 2.12-2.26 (m, 1 H) 2.43 (d, J=8.84 Hz, 1 H) 2.64-2.85 (m, 3 H) 2.85-3.02 (m, 4 H) 3.43-3.68 (m, 1 H) 3.68-3.90 (m, 1 H) 3.90-4.03 (m, 1 H) 4.03-4.26 (m, 0 H) 4.99-5.19 (m, 2 H) 5.51-5.71 (m, 1 H) 7.08-7.25 (m, 1 H) 7.79-7.92 (m, 1 H) 8.32 (d, J=5.31 Hz, 1 H). [M+H] calc'd for $C_{19}H_{25}N_5O_2$, 356; found, 356.6.

Example 60

4-((2R)-1-(3-(methoxymethyl)pyrrolidin-1-yl)-1-oxobutan-2-yl)-4,5-dihydropyrrolo[4,3,2-de][2,6]naphthyridin-3(1 H)-one

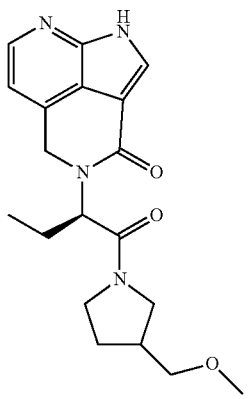 [SMILES: CC[C@H](C(=O)N1CCC(COC)C1)N1Cc2ccnc3[nH]cc(c23)C1=O]

The title compound was prepared in accordance with General Procedure A, using 3-(methoxymethyl)pyrrolidine as the amine, NHR₁R₂ (12 mg, 22.6%, 3 steps). ¹H NMR (400 MHz, CD₃OD) δ 0.98 (td, J=7.39, 1.89 Hz, 3 H) 1.62-1.80 (m, 1 H) 1.85-2.12 (m, 5 H) 2.35-2.60 (m, 1 H) 3.32-3.35 (m, 3 H) 3.37-3.51 (m, 2 H) 3.52-3.70 (m, 1 H) 3.70-3.85 (m, 1 H) 5.06-5.29 (m, 2 H) 5.53-5.69 (m, 1 H) 7.19-7.35 (m, 1 H) 7.89 (s, 1 H) 8.34 (d, J=5.31 Hz, 1H). [M+H] calc'd for $C_{19}H_{24}N_4O_3$, 357; found, 357.6.

Example 61

4-((2R)-1-(3-methylpiperidin-1-yl)-1-oxobutan-2-yl)-4,5-dihydropyrrolo[4,3,2-de][2,6]naphthyridin-3(1 H)-one

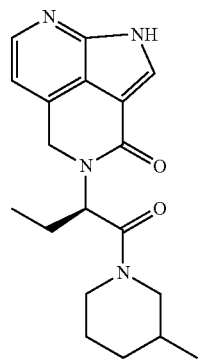 [SMILES: CC[C@H](C(=O)N1CCCC(C)C1)N1Cc2ccnc3[nH]cc(c23)C1=O]

The title compound was prepared in accordance with General Procedure A, using 3-methylpiperidine as the amine, NHR₁R₂ (10.8 mg, 21.3%, 3 steps). ¹H NMR (400 MHz, CD₃OD) δ 0.71 (d, J=6.32 Hz, 1 H) 0.83-1.04 (m, 7 H) 1.14 (br. s., 1 H) 1.68 (d, J=10.36 Hz, 2 H) 1.81-2.07 (m, 2 H) 2.54-2.77 (m, 1 H) 2.95-3.10 (m, 1 H) 4.01 (d, J=14.65 Hz, 1 H) 4.20-4.51 (m, 1 H) 4.89-5.04 (m, 1 H) 5.04-5.18 (m, 1 H) 5.71-5.87 (m, 1 H) 7.19-7.26 (m, 1 H) 7.89 (d, J=4.80 Hz, 1 H) 8.33 (d, J=5.31 Hz, 1 H). [M+H] calc'd for $C_{19}H_{24}N_4O_2$, 341; found, 341.6.

Example 62

(R)-4-(1-(4-(2-hydroxypropan-2-yl)piperidin-1-yl)-1-oxobutan-2-yl)-4,5-dihydropyrrolo[4,3,2-de][2,6]naphthyridin-3(1 H)-one

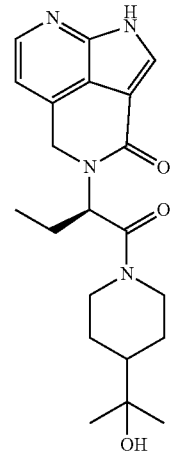 [SMILES: CC[C@H](C(=O)N1CCC(C(C)(C)O)CC1)N1Cc2ccnc3[nH]cc(c23)C1=O]

The title compound was prepared in accordance with General Procedure A, using 2-(piperidin-4-yl)propan-2-ol as the amine, NHR₁R₂ (10 mg, 17.5%, 3 steps). ¹H NMR (400 MHz, CD₃OD) δ 0.80 (s, 3 H) 0.85 (s, 3 H) 0.92-1.00 (m, 3 H) 1.43-1.56 (m, 1 H) 1.60 (d, J=13.89 Hz, 1 H) 1.77 (d, J=12.88 Hz, 1 H) 1.83-1.95 (m, 2 H) 1.95-2.06 (m, 2 H) 2.48-2.66 (m, 1 H) 2.86-3.07 (m, 1 H) 4.16 (d, J=15.66 Hz, 1 H) 4.64 (d, J=14.15 Hz, 1 H) 4.87-5.03 (m, 1 H) 5.03-5.19 (m, 1 H) 5.75 (t, J=7.58 Hz, 1 H) 7.23 (d, J=5.31 Hz, 1 H) 7.81-7.94 (m, 1 H) 8.23-8.37 (m, 1 H). [M+H] calc'd for $C_{21}H_{28}N_4O_3$, 385; found, 385.6.

Example 63

(R)-4-(1-(4-(methylsulfonyl)piperazin-1-yl)-1-oxobutan-2-yl)-4,5-dihydropyrrolo[4,3,2-de][2,6]naphthyridin-3(1 H)-one

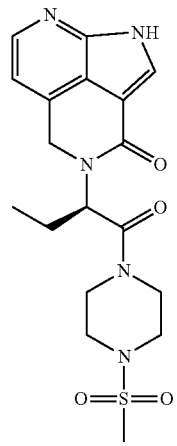 [SMILES: CC[C@H](C(=O)N1CCN(S(C)(=O)=O)CC1)N1Cc2ccnc3[nH]cc(c23)C1=O]

The title compound was prepared in accordance with General Procedure A, using 1-(methylsulfonyl)piperazine as the amine, NHR$_1$R$_2$ (7.3 mg, 12.1%, 3 steps). $^1$H NMR (400 MHz, CD$_3$OD) δ 0.97 (t, J=7.45 Hz, 3 H) 1.85-2.06 (m, 2 H) 2.75 (s, 3 H) 3.06 (br.s., 1 H) 3.09-3.19 (m, 1 H) 3.26 (dd, J=3.16, 1.64 Hz, 2 H) 3.68 (br. s., 1 H) 3.74 (br. s., 1 H) 3.79 (br. s., 2 H) 4.96-5.14 (m, 2 H) 5.76 (dd, J=8.34, 6.82 Hz, 1 H) 7.23 (d, J=5.31 Hz, 1 H) 7.89 (s, 1 H) 8.32 (d, J=5.56 Hz, 1 H). [M+H] calc'd for C$_{18}$H$_{23}$N$_5$O$_4$S, 406; found, 406.6.

Example 64

(R)-4-(1-oxo-1-(4-(pyridin-2-yl)piperazin-1-yl)butan-2-yl)-4,5-dihydropyrrolo[4,3,2-de][2,6]naphthyridin-3(1H)-one

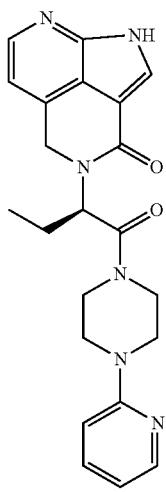 [SMILES: CC[C@H](C(=O)N1CCN(c2ccccn2)CC1)N1Cc2ccnc3[nH]cc(c23)C1=O]

The title compound was prepared in accordance with General Procedure A, using 1-(pyridin-2-yl)piperazine as the amine, NHR$_1$R$_2$ (5.2%, 3 steps). $^1$H NMR (400 MHz, CD$_3$OD) δ 0.88-1.04 (m, 3 H) 1.93-2.09 (m, 2 H) 3.54-3.63 (m, 1 H) 3.69 (d, J=11.12 Hz, 1 H) 3.72-3.87 (m, 3 H) 3.87-3.95 (m, 2 H) 3.98 (br. s., 1 H) 5.05 (q, J=19.28 Hz, 2 H) 5.80 (dd, J=8.34, 6.82 Hz, 1 H) 6.99 (t, J=6.69 Hz, 1 H) 7.14 (d, J=5.05 Hz, 1 H) 7.33 (d, J=9.35 Hz, 1 H) 7.84 (s, 1 H) 7.92 (dd, J=6.32, 1.26 Hz, 1 H) 8.01 (ddd, J=9.22, 7.20, 1.77 Hz, 1 H) 8.29 (d, J=5.30 Hz, 1 H). [M+H] calc'd for C$_{22}$H$_{24}$N$_6$O$_2$, 405; found, 405.6.

Example 65

(R)—N-cyclopropyl-2-(3-oxopyrrolo[4,3,2-de][2,6]naphthyridin-4(1H,3H,5H)-yl)butanamide

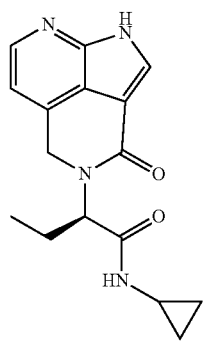 [SMILES: CC[C@H](C(=O)NC1CC1)N1Cc2ccnc3[nH]cc(c23)C1=O]

The title compound was prepared in accordance with General Procedure A, using cyclopropanamine as NHR$_1$R$_2$ (1.7 mg, 2.2%, 3 steps). $^1$H NMR (400 MHz, CD$_3$OD) δ 0.44-0.53 (m, 2 H) 0.96 (t, J=7.33 Hz, 3 H) 2.66-2.73 (m, 4 H) 3.71-3.81 (m, 1 H) 5.05-5.29 (m, 1 H) 5.44-5.52 (m, 2 H) 7.52 (dd, J=8.46, 4.42 Hz, 1 H) 8.43 (dd, J=8.34, 1.26 Hz, 1 H) 8.73 (d, J=3.54 Hz, 1 H). [M+H] calc'd for C$_{16}$H$_{18}$N$_4$O$_2$, 299; found, 299.6.

Example 66

(R)—N-(cyclopropylmethyl)-2-(3-oxopyrrolo[4,3,2-de][2,6]naphthyridin-4(1H,3H,5H)-yl)butanamide

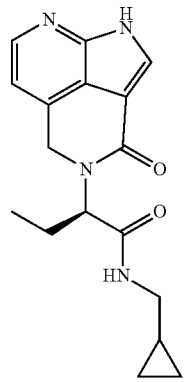 [SMILES: CC[C@H](C(=O)NCC1CC1)N1Cc2ccnc3[nH]cc(c23)C1=O]

The title compound was prepared in accordance with General Procedure A, using cyclopropylmethanamine as NHR$_1$R$_2$ (9 mg, 11.2%, 3 steps). $^1$H NMR (400 MHz, CD$_3$OD) δ 0.13-0.22 (m, 2 H) 0.40-0.48 (m, 2 H) 0.90-1.06 (m, 4 H) 1.86-2.01 (m, 1 H) 2.05-2.16 (m, 1 H) 3.06 (d, J=6.82 Hz, 2 H) 5.04-5.13 (m, 1 H) 5.13-5.22 (m, 1 H) 5.28 (dd, J=9.47, 6.69 Hz, 1 H) 7.14 (d, J=5.05 Hz, 1 H) 7.81 (s, 1 H) 8.29 (d, J=4.80 Hz, 1 H). [M+H] calc'd for C$_{17}$H$_{20}$N$_4$O$_2$, 313; found, 313.6.

Example 67

(R)—N-isobutyl-2-(3-oxopyrrolo[4,3,2-de][2,6]naphthyridin-4(1H,3H,5H)-yl)butanamide

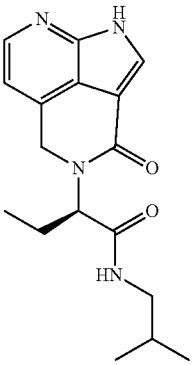 [SMILES: CC[C@H](C(=O)NCC(C)C)N1Cc2ccnc3[nH]cc(c23)C1=O]

The title compound was prepared in accordance with General Procedure A, using 2-methylpropan-1-amine as NHR$_1$R$_2$ (5.2 mg, 6.4%, 3 steps). $^1$H NMR (400 MHz, CD$_3$OD) δ 0.87 (d, J=6.32 Hz, 6 H) 0.99 (t, J=7.45 Hz, 3 H) 1.78 (dt, J=13.58, 6.73 Hz, 1 H) 1.95 (ddd, J=14.15, 9.35, 7.33 Hz, 1 H) 2.11 (dt, J=14.65, 7.33 Hz, 1 H) 3.01 (dd, J=6.95, 1.64 Hz, 2 H) 5.04-5.19 (m, 1 H) 5.19-5.32 (m, 2 H) 7.24 (d, J=5.31 Hz, 1 H) 7.87 (s, 1 H) 8.33 (d, J=5.56 Hz, 1 H). [M+H] calc'd for C$_{17}$H$_{22}$N$_4$O$_2$, 315; found, 315.6.

Example 68

(R)—N-isobutyl-N-methyl-2-(3-oxopyrrolo[4,3,2-de][2,6]naphthyridin-4(1H,3H,5H)-yl)butanamide

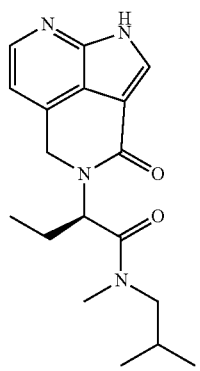 [SMILES: CC[C@H](C(=O)N(C)CC(C)C)N1Cc2ccnc3[nH]cc(c23)C1=O]

The title compound was prepared in accordance with General Procedure A, using N,2-dimethylpropan-1-amine as $NHR_1R_2$ (10.5 mg, 12.4%, 3 steps). $^1$H NMR (400 MHz, $CD_3OD$) δ 0.85 (td, J=6.95, 6.06 Hz, 5 H) 0.90-1.09 (m, 4 H) 1.84-2.09 (m, 4 H) 2.94 (s, 1 H) 3.05-3.16 (m, 2 H) 3.24 (dd, J=7.45, 3.92 Hz, 1 H) 3.46 (dd, J=14.27, 8.21 Hz, 1 H) 5.11 (s, 1 H) 5.68-5.90 (m, 1 H) 7.15-7.33 (m, 1 H) 7.88 (d, J=3.28 Hz, 1 H) 8.32 (dd, J=5.31, 3.03 Hz, 1 H). [M+H] calc'd for $C_{18}H_{24}N_4O_2$, 329; found, 329.6.

Examples 69

(2R)—N-(1-hydroxypropan-2-yl)-2-(3-oxopyrrolo[4,3,2-de][2,6]naphthyridin-4(1H,3H,5H)-yl)butanamide

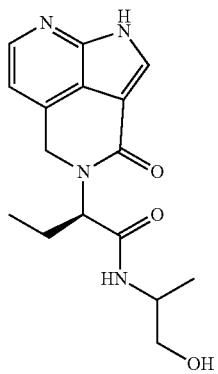 [SMILES: CC[C@H](C(=O)NC(C)CO)N1Cc2ccnc3[nH]cc(c23)C1=O]

The title compound was prepared in accordance with General Procedure A, using 2-aminopropan-1-ol as the amine, $NHR_1R_2$ (27 mg, 33.1%, 3 steps). $^1$H NMR (400 MHz, $CD_3OD$) δ 0.88-1.03 (m, 2 H) 1.04-1.19 (m, 2 H) 1.85-2.00 (m, 1 H) 2.04-2.17 (m, 1 H) 2.75-2.87 (m, 1 H) 2.87-3.05 (m, 1 H) 3.05-3.21 (m, 1 H) 3.38-3.56 (m, 2 H) 3.93-4.05 (m, 1 H) 4.97-5.13 (m, 1 H) 5.13-5.32 (m, 1 H) 7.05-7.19 (m, 1 H) 7.80 (s, 1 H) 8.27 (d, J=5.05 Hz, 1 H). [M+H] calc'd for $C_{16}H_{20}N_4O_3$, 317; found, 317.6.

Example 70

(R)—N-(2-hydroxy-2-methylpropyl)-2-(3-oxopyrrolo[4,3,2-de][2,6]naphthyridin-4(1H,3H,5H)-yl)butanamide

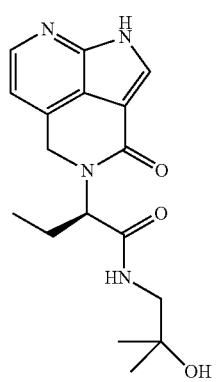 [SMILES: CC[C@H](C(=O)NCC(C)(C)O)N1Cc2ccnc3[nH]cc(c23)C1=O]

The title compound was prepared in accordance with General Procedure A, using 1-amino-2-methylpropan-2-ol as the amine, $NHR_1R_2$ (12 mg, 14.1%, 3 steps). $^1$H NMR (400 MHz, $CD_3OD$) δ 1.00 (t, J=7.33 Hz, 3 H) 1.13 (d, J=2.27 Hz, 6 H) 1.90-2.02 (m, 1 H) 2.08-2.22 (m, 1 H) 3.15-3.26 (m, 2 H) 5.07-5.21 (m, 1 H) 5.21-5.37 (m, 2 H) 7.28 (d, J=5.56 Hz, 1 H) 7.89 (s, 1 H) 8.34 (d, J=5.56 Hz, 1 H). [M+H] calc'd for $C_{17}H_{22}N_4O_3$, 331; found, 331.6.

Example 71

(R)—N—((S)-2,3-dihydroxypropyl)-2-(3-oxopyrrolo[4,3,2-de][2,6]naphthyridin-4(1H,3H,5H)-yl)butanamide

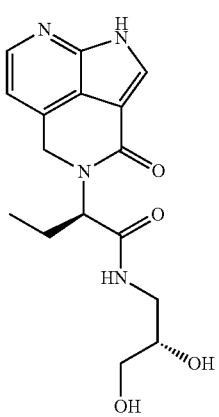 [SMILES: CC[C@H](C(=O)NC[C@H](O)CO)N1Cc2ccnc3[nH]cc(c23)C1=O]

The title compound was prepared in accordance with General Procedure A, using (S)-3-aminopropane-1,2-diol as the amine, $NHR_1R_2$ (1.9 mg, 2.2%, 3 steps). $^1$H NMR (400 MHz, $CD_3OD$) δ 0.98 (t, J=7.33 Hz, 2 H) 1.29 (s, 1 H) 1.86-2.02 (m, 1 H) 2.06-2.19 (m, 1 H) 2.70 (s, 1 H) 3.08-3.29 (m, 1 H) 3.40-3.51 (m, 2 H) 3.61-3.77 (m, 1 H) 5.02-5.32 (m, 3 H) 7.16

(d, J=4.80 Hz, 1 H) 7.82 (s, 1 H) 8.31 (br. s., 1 H). [M+H] calc'd for $C_{16}H_{20}N_4O_4$, 333; found, 333.6.

Example 72

(R)-2-(3-oxopyrrolo[4,3,2-de][2,6]naphthyridin-4(1H,3H,5H)-yl)-N-phenylbutanamide

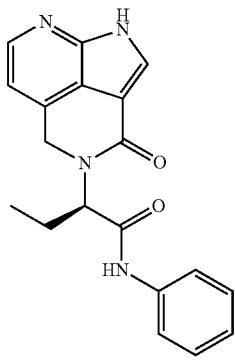 [SMILES: CC[C@H](C(=O)Nc1ccccc1)N1Cc2ccnc3[nH]cc(c23)C1=O]

The title compound was prepared in accordance with General Procedure A, using aniline as the amine, $NHR_1R_2$ (5 mg, 5.8%, 3 steps). $^1H$ NMR (400 MHz, $CD_3OD$) δ 1.05 (t, J=7.33 Hz, 3 H) 2.04-2.13 (m, 1 H) 2.13-2.28 (m, 1 H) 5.11-5.27 (m, 1 H) 5.31-5.47 (m, 2 H) 7.00-7.14 (m, 1 H) 7.21 (d, J=5.31 Hz, 1 H) 7.23-7.36 (m, 2 H) 7.54 (dd, J=8.59, 1.01 Hz, 2 H) 7.85 (s, 1 H) 8.32 (br. s., 1 H). [M+H] calc'd for $C_{19}H_{18}N_4O_2$, 335; found, 335.6.

Example 73

(R)—N-(1-(methylsulfonyl)piperidin-4-yl)-2-(3-oxopyrrolo[4,3,2-de][2,6]naphthyridin-4(1H,3H,5H)-yl)butanamide

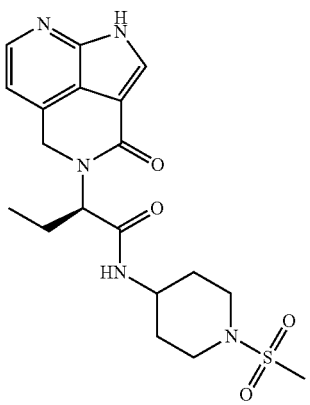 [SMILES: CC[C@H](C(=O)NC1CCN(S(C)(=O)=O)CC1)N1Cc2ccnc3[nH]cc(c23)C1=O]

The title compound was prepared in accordance with General Procedure A, using 1-(methylsulfonyl)piperidin-4-amine as $NHR_1R_2$ (20 mg, 18.5%, 3 steps). $^1H$ NMR (400 MHz, $CD_3OD$) δ 0.99 (t, J=7.33 Hz, 2 H) 1.26-1.42 (m, 2 H) 1.46-1.67 (m, 2H) 1.84-2.00 (m, 2 H) 2.06-2.25 (m, 1 H) 2.76-2.94 (m, 4 H) 3.22 (quin, J=6.95 Hz, 1 H) 3.33-3.39 (m, 2 H) 3.59-3.88 (m, 3 H) 5.11-5.27 (m, 1 H) 7.29 (d, J=5.31 Hz, 1 H) 7.89 (s, 1 H) 8.35 (d, J=5.31 Hz, 1 H). [M+H] calc'd for $C_{19}H_{25}N_5O_4S$, 420; found, 420.6.

Example 74

(2R)-2-(3-oxopyrrolo[4,3,2-de][2,6]naphthyridin-4(1H,3H,5H)-yl)-N-((tetrahydrofuran-2-yl)methyl)butanamide

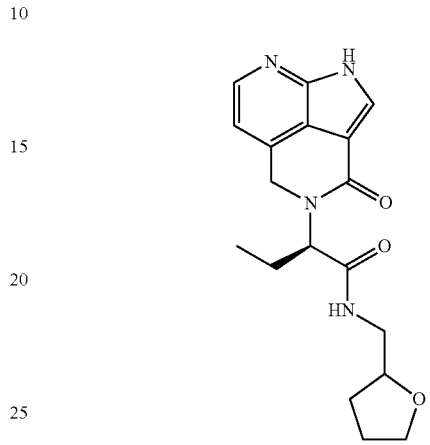

The title compound was prepared in accordance with General Procedure A, using (tetrahydrofuran-2-yl)methanamine as $NHR_1R_2$ (3.1 mg, 3.5%, 3 steps). $^1H$ NMR (400 MHz, $CD_3OD$) δ 0.98 (td, J=7.39, 1.64 Hz, 3 H) 1.55 (s, 1 H) 1.75-2.02 (m, 4 H) 2.12 (dt, J=14.46, 7.29 Hz, 1 H) 3.18-3.30 (m, 2 H) 3.57-3.73 (m, 1 H) 3.73-3.87 (m, 1 H) 3.96 (dd, J=11.12, 6.32 Hz, 1 H) 5.01-5.22 (m, 2 H) 5.29 (dt, J=9.35, 6.82 Hz, 1 H) 7.16 (d, J=5.05 Hz, 1 H) 7.83 (s, 1 H) 8.30 (d, J=5.05 Hz, 1 H). [M+H] calc'd for $C_{18}H_{22}N_4O_3$, 343; found, 343.6.

Example 75

(2R)—N-(1-cyanoethyl)-2-(6-fluoro-3-oxopyrrolo[4,3,2-de][2,6]naphthyridin-4(1H,3H,5H)-yl)-3-methylbutanamide

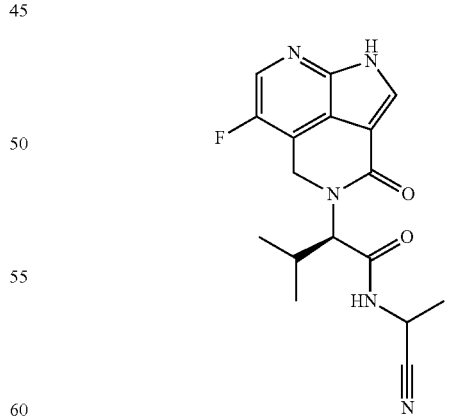

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). 2-Aminopropanenitrile hydrochloride (8.23 mg, 0.077 mmol) and 4-methylmorpholine (0.023 mL, 0.206 mmol) were added and the reaction mixture was stirred at room temperature for 2 h. Following reaction, the product was purified by preparative HPLC (10-55% AcCN/H₂O with 0.035% TFA), concentrated in vacuo, and lyophilized to afford the title compound as a white solid (11 mg, 62%). ¹H NMR (500 MHz, DMSO-$d_6$) δ 1.20-1.26 (m, 3H), 1.32-1.39 (m, 3H), 1.77-1.82 (m, 3H), 2.76-2.84 (m, 1H), 5.06-5.22 (m, 1H), 5.36-5.44 (m, 2H), 5.77 (dd, J=19.0, 2.0 Hz, 1H), 8.38 (dd, J=10.5, 2.0 Hz, 1H), 8.65 (t, J=3.0 Hz, 1H), 9.47 (d, J=2.0 Hz, 1H), 12.78 (br d, J=7.5 Hz, 1H). [M+H] calc'd for $C_{17}H_{18}FN_5O_2$, 344; found, 344.

Example 76

(R)-4-(1-(3,3-difluoroazetidin-1-yl)-3-methyl-1-oxobutan-2-yl)-6-fluoro-4,5-dihydropyrrolo[4,3,2-de][2,6]naphthyridin-3(1H)-one

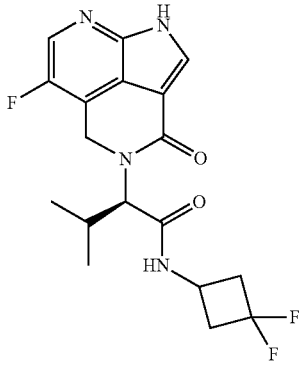 [SMILES: CC(C)[C@H](C(=O)NC1CC(F)(F)C1)N1Cc2c(F)cnc3[nH]cc(c23)C1=O]

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). 3,3-Difluoroazetidine hydrochloride (10.0 mg, 0.077 mmol) and 4-methylmorpholine (0.023 mL, 0.206 mmol) were added, and the reaction mixture was stirred at room temperature for 2 h. Following reaction, the product was purified by preparative HPLC (10-60% AcCN/H₂O with 0.035% TFA), concentrated in vacuo, and lyophilized to afford the title compound as a white solid (10 mg, 53%). ¹H NMR (500 MHz, DMSO-$d_6$) δ 0.80 (d, J=6.0 Hz, 3H), 0.96 (d, J=6.0 Hz, 3H), 2.30-2.41 (m, 1H), 4.26-4.36 (m, 2H), 4.41-4.51 (m, 1H), 4.70-4.79 (m, 1H), 5.00 (AB q, J=104.5, 22.0 Hz, 2H), 5.07 (d, J=23.0 Hz, 1H), 7.99 (d, J=2.5 Hz, 1H), 8.24 (d, J=2.5 Hz, 1H), 12.40 (s, 1H). [M+H] calc'd for $C_{17}H_{17}F_3N_4O_2$, 367; found, 367.

Example 77

(R)-4-(1-(1,1-dioxidothiazolidin-3-yl)-3-methyl-1-oxobutan-2-yl)-6-fluoro-4,5-dihydropyrrolo[4,3,2-de][2,6]naphthyridin-3(1H)-one

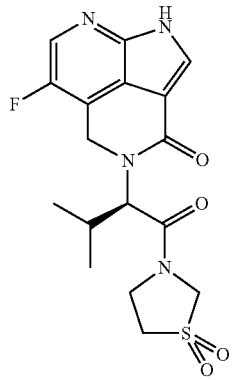 [SMILES: CC(C)[C@H](C(=O)N1CCS(=O)(=O)C1)N1Cc2c(F)cnc3[nH]cc(c23)C1=O]

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). Thiazolidine 1,1-dioxide hydrochloride (12.17 mg, 0.077 mmol) and 4-methylmorpholine (0.023 mL, 0.206 mmol) were added, and the reaction mixture was stirred at room temperature for 2 h. The product was purified by preparative HPLC (10-45% AcCN/H₂O with 0.035% TFA), concentrated in vacuo, and lyophilized to afford the title compound as a white solid (8.8 mg, 43%). ¹H NMR (500 MHz, DMSO-$d_6$) δ 0.76-0.81 (m, 3H), 0.95 (d, J=6.5 Hz, 3H), 2.41-2.50 (m, 1H), 3.35-3.45 (m, 2H), 3.80-3.89 (m, 2H), 4.49-4.91 (m, 4H), 5.18-5.42 (m, 1H), 8.01 (d, J=2.5 Hz, 1H), 8.24 (d, J=2.5 Hz, 1H), 12.43 (s, 1H). [M+H] calc'd for $C_{17}H_{19}FN_4O_4S$, 395; found, 395.

Example 78

(R)-2-(6-fluoro-3-oxopyrrolo[4,3,2-de][2,6]naphthyridin-4(1H,3H,5H)-yl)-N,3-dimethyl-N-(2-(methylsulfonyl)ethyl)butanamide

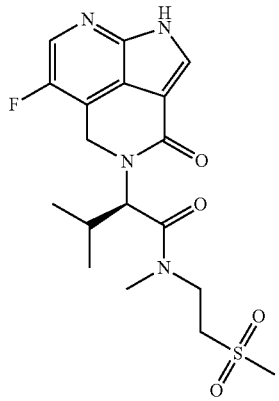 [SMILES: CC(C)[C@H](C(=O)N(C)CCS(C)(=O)=O)N1Cc2c(F)cnc3[nH]cc(c23)C1=O]

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). N-methyl-2-(methylsulfonyl)ethanamine (10.60 mg, 0.077 mmol) and 4-methylmorpholine (0.023 mL, 0.206 mmol) were added, and the reaction mixture was stirred at room temperature for 2 h. The product was purified by preparative HPLC (10-45% AcCN/H₂O with 0.035% TFA), concentrated in vacuo, and lyophilized to afford the title compound as a white solid (12 mg, 57% yield). ¹H NMR (500 MHz, CD₃OD) δ 0.77 (d, J=6.5 Hz, 3H), 0.95 (d, J=6.5 Hz, 3H), 2.41-2.49 (m, 1H), 2.97 (s, 3H), 3.05 (s, 3H), 3.36 (t, J=6.5 Hz, 2H), 3.78 (t, J=6.5 Hz, 2H), 4.81-4.96 (m, 2H), 5.36 (d, J=11.0 Hz, 1H), 7.97 (d, J=2.5 Hz, 1H), 8.23 (d, J=2.5 Hz, 1H), 12.39 (s, 1H). [M+H] calc'd for $C_{18}H_{23}FN_4O_4S$, 411; found, 411.

Example 79

(R)—N-(cyanomethyl)-2-(6-fluoro-3-oxopyrrolo[4,3,2-de][2,6]naphthyridin-4(1H,3H,5H)-yl)-N,3-dimethylbutanamide

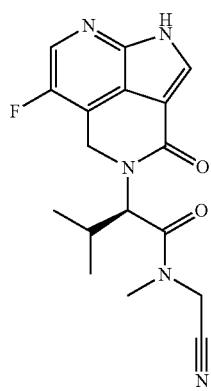 [SMILES: CC(C)[C@H](C(=O)N(C)CC#N)N1Cc2c(F)cnc3[nH]cc(c23)C1=O]

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). 2-(Methylamino)acetonitrile (5.41 mg, 0.077 mmol) and 4-methylmorpholine (0.023 mL, 0.206 mmol) were added, and the reaction mixture was stirred at room temperature for 2 h. The product was purified by preparative HPLC (10-55% AcCN/H$_2$O with 0.035% TFA), concentrated in vacuo, and lyophilized to afford the title compound as a pale yellow solid (7.8 mg, 44%). $^1$H NMR (500 MHz, DMSO-d$_6$) δ 0.78 (d, J=6.5 Hz, 3H), 0.92 (d, J=6.5 Hz, 3H), 2.44-2.51 (m, 1H), 3.12 (s, 3H), 4.39 (AB q, J=84.5, 17.5 Hz, 2H), 4.89 (d, J=5.5 Hz, 2H), 5.42 (d, J=11.0 Hz, 1H), 8.00 (d, J=2.5 Hz, 1H), 8.24 (d, J=2.5 Hz, 1H), 12.43 (s, 1H). [M+H] calc'd for C$_{17}$H$_{18}$FN$_5$O$_2$, 344; found, 344.

Example 80

(R)-4-(1-(3-(difluoromethyl)azetidin-1-yl)-3-methyl-1-oxobutan-2-yl)-6-fluoro-4,5-dihydropyrrolo[4,3,2-de][2,6]naphthyridin-3(1H)-one

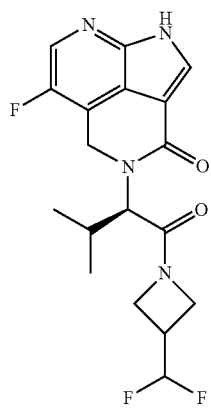 [SMILES: CC(C)[C@H](C(=O)N1CC(C(F)F)C1)N1Cc2c(F)cnc3[nH]cc(c23)C1=O]

(R)-2-(6-Fluoro-3-oxopyrrolo[4,3,2-de][2,6]naphthyridin-4(1H,3H,5H)-yl)-3-methylbutanoic acid (15 mg, 0.051 mmol), HOBt hydrate (9.46 mg, 0.062 mmol), and EDC hydrochloride (14.81 mg, 0.077 mmol) were combined in DMF (2 mL). 3-(Difluoromethyl)azetidine (8.27 mg, 0.077 mmol) and 4-methylmorpholine (0.023 mL, 0.206 mmol) were added, and the reaction mixture was stirred at room temperature for 2 h. The product was purified by preparative HPLC (10-60% AcCN/H$_2$O with 0.035% TFA), concentrated in vacuo, and lyophilized to afford the title compound as a white solid (9.8 mg, 50%). $^1$H NMR (500 MHz, DMSO-d$_6$) δ 0.78 (d, J=6.0 Hz, 3H), 0.94 (d, J=6.0 Hz, 3H), 2.31-2.39 (m, 1H), 2.99-3.15 (m, 1H), 3.77-4.35 (m, 4H), 4.82-5.11 (m, 3H), 6.10-6.41 (m, 1H), 7.98 (d, J=2.5 Hz, 1H), 8.24 (d, J=2.5 Hz, 1H), 12.39 (s, 1H). [M+H] calc'd for C$_{18}$H$_{19}$F$_3$N$_4$O$_2$, 381; found, 381.

PREPARATION U: 4-formyl-1-tosyl-1H-pyrrolo[2,3-b]pyridine-3-carboxylic acid

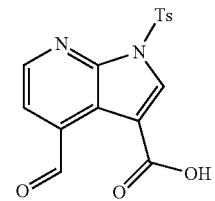 [SMILES: Cc1ccc(S(=O)(=O)n2cc(C(=O)O)c3c(C=O)ccnc32)cc1]

STEP A: 3-Iodo-1-tosyl-1H-pyrrolo[2,3-b]pyridine-4-carbaldehyde

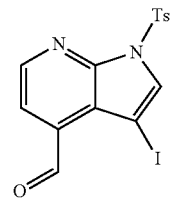 [SMILES: Cc1ccc(S(=O)(=O)n2cc(I)c3c(C=O)ccnc32)cc1]

To a solution of 1H-pyrrolo[2,3-b]pyridine-4-carbaldehyde (2.0 g, 13.7 mmol) in EtOH (40 mL) was added iodine (4.17 g, 16.4 mmol), sodium iodide (2.46 g, 16.4 mmol), and aqueous NaOH (1N, 16 mL). After stirring for 4 h at room temperature, the reaction mixture was diluted with water (200 mL), and the orange precipitate was collected by filtration and dried under vacuum. The solid was dissolved in DMF (20 mL); sodium hydride (60%, 660 mg, 16.4 mmol) was slowly added, and after stirring the deep red solution at room temperature for 30 min, tosyl chloride (2.87 g, 15.1 mmol) was added. The reaction mixture was stirred for an additional 2 h at room temperature, and was then diluted with EtOAc and quenched with water. The organics were separated, washed with aqueous NaHSO$_3$ (0.1 N) and brine, dried over MgSO$_4$, and concentrated in vacuo. Purification by silica gel chromatography (3:1:1 hexane/DCM/EtOAc) gave the title compound as a yellow solid (3.48 g, 60%). $^1$H NMR (500 MHz, DMSO-d$_6$) δ 2.33 (s, 3H), 7.43 (d, J=8.5 Hz, 2H), 7.63 (d, J=5.0 Hz, 1H), 8.03 (d, J=8.5 Hz, 2H), 8.39 (s, 1H), 8.60 (d, J=5.0 Hz, 1H), 11.31 (s, 1H). [M+H] calc'd for C$_{15}$H$_{11}$N$_2$O$_3$S, 427; found, 427.

STEP B: 4-Formyl-1-tosyl-1H-pyrrolo[2,3-b]pyridine-3-carboxylic acid

Lithium chloride (358 mg, 8.45 mmol) and lithium formate monohydrate (591 mg, 8.45 mmol) were combined in a dry sealable tube under nitrogen. DMF (12 mL), 3-iodo-1-tosyl-1H-pyrrolo[2,3-b]pyridine-4-carbaldehyde (1.2 g, 2.82 mmol), acetic anhydride (532 mL, 5.63 mmol) and palladium acetate (63 mg, 0.28 mmol) were added. DIPEA (981 µL) was added, and the reaction tube was sealed and heated at 56° C. for 4 h. The reaction mixture was taken up in MeOH/DCM (20%) and filtered to remove the insoluble black carbon material. The yellow solution was concentrated in vacuo, dissolved in MeOH/DCM (10%), and washed with aqueous HCl (0.1N). The aqueous layer was extracted twice with MeOH/DCM (10%). The organics were combined, dried over MgSO$_4$, and concentrated in vacuo. Purification by silica gel chromatography (10-15% MeOH/DCM) gave the title compound as a tan solid (866 mg, 89%). $^1$H NMR (500 MHz, DMSO-d$_6$) δ 2.35 (s, 3H), 7.45 (d, J=8.5 Hz, 2H), 7.62 (d, J=5.0 Hz, 1H), 8.11 (d, J=8.5 Hz, 2H), 8.58-8.62 (m, 2H), 11.02 (s, 1H), 13.20 (br s, 1H). [M+H] calc'd for $C_{16}H_{12}N_2O_5S$, 345; found, 345.

PREPARATION V: (R)-3-methyl-2-(3-oxopyrrolo[4,3,2-de][2,6]naphthyridin-4(1H,3H,5H)-yl)butanoic acid

STEP A: (R)-tert-butyl 3-methyl-2-(3-oxo-1-tosylpyrrolo[4,3,2-de][2,6]naphthyridin-4(1H,3H,5H)-yl)butanoate

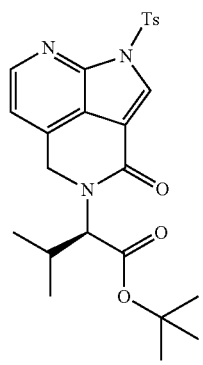 [SMILES: Cc1ccc(S(=O)(=O)n2cc3c4c(ccnc42)CN([C@@H](C(=O)OC(C)(C)C)C(C)C)C3=O)cc1]

Sodium triacetoxyborohydride (603 mg, 2.85 mmol) and D-valine-tert-butyl ester HCl salt (597 mg, 2.85 mmol) were combined in DCM (15 mL). The reaction mixture was stirred for 20 min at room temperature and then cooled to 0° C. 4-Formyl-1-tosyl-1H-pyrrolo[2,3-b]pyridine-3-carboxylic acid (700 mg, 2.03 mmol) was added, and the solution was stirred for 1 h. The solution was concentrated in vacuo to give a white foam, which was re-dissolved in THF (40 mL). HATU (1.16 g, 3.05 mmol) and N-methylmorpholine (339 µL, 3.05 mmol) were added, and the reaction mixture was stirred at 52° C. for 2 h. Additional HATU (580 mg, 1.53 mmol) and N-methylmorpholine (170 µL, 1.53 mmol) were added, and the reaction mixture was stirred for an additional 2 h at 52° C. The solution was subsequently cooled, diluted with EtOAc, and washed with brine. The organics were dried over MgSO$_4$ and concentrated in vacuo. Purification by silica gel chromatography (1:2:2 EtOAc/Hexanes/DCM) gave the title compound as a yellow oil, which solidified upon sitting (840 mg, 85%). $^1$H NMR (500 MHz, CDCl$_3$) δ 0.86 (d, J=7.0 Hz, 3H), 1.08 (d, J=7.0 Hz, 3H), 1.42 (s, 9H), 2.25-2.34 (m, 1H), 2.35 (s, 3H), 4.77-5.14 (m, 3H), 7.05 (d, J=5.0 Hz, 1H), 7.28 (d, J=7.5 Hz, 2H), 8.05-8.10 (m, 3H), 8.45 (d, J=5.0 Hz, 1H). [M+H] calc'd for $C_{25}H_{29}N_3O_5S$, 484; found, 484.

STEP B: (R)-3-Methyl-2-(3-oxopyrrolo[4,3,2-de][2,6]naphthyridin-4(1H,3H,5H)-yl)butanoic acid

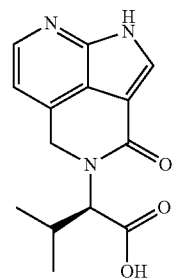 [SMILES: CC(C)[C@H](C(=O)O)N1Cc2ccnc3[nH]cc(c23)C1=O]

A mixture of (R)-tert-Butyl 3-methyl-2-(3-oxo-1-tosylpyrrolo[4,3,2-de][2,6]naphthyridin-4(1H,3H,5H)-yl)butanoate (840 mg, 1.74 mmol), MeOH (4 mL), and aqueous NaOH (1N, 2 mL) was stirred for 40 min at room temperature. The material was diluted with DCM and washed with brine. The organics were dried over MgSO$_4$ and concentrated in vacuo. Purification by silica gel chromatography (5% MeOH/DCM) gave a yellow oil (390 mg), which dissolved in TFA/DCM (50%) and stirred at room temperature for 1 h. The solution was concentrated and dried under vacuum to give the title compound as a tan solid (320 mg, 67%). $^1$H NMR (500 MHz, CD$_3$OD) δ 0.88 (d, J=7.0 Hz, 3H), 1.10 (d, J=7.0 Hz, 3H), 2.35-2.44 (m, 1H), 4.95-5.33 (m, 3H), 7.34 (d, J=6.0 Hz, 1H), 7.90 (s, 1H), 8.33 (d, J=6.0 Hz, 1H). [M+H] calc'd for $C_{14}H_{15}N_3O_3$, 274; found, 274.

Example 81

(R)-1-(3-methyl-2-(3-oxopyrrolo[4,3,2-de][2,6]naphthyridin-4(1H,3H,5H)-yl)butanoyl)azetidine-3-carbonitrile

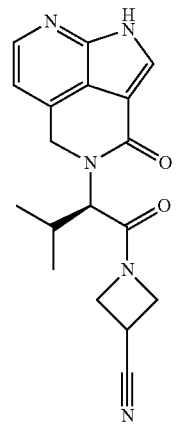

(R)-3-Methyl-2-(3-oxopyrrolo[4,3,2-de][2,6]naphthyridin-4(1H,3H,5H)-yl)butanoic acid (80 mg, 0.29 mmol), HOBt (54 mg, 0.35 mmol) and EDC (84 mg, 0.44 mmol) were combined in DMF (2 mL). Azetidine-3-carbonitrile HCl salt (52 mg, 0.44 mmol) and N-methylmorpholine (130 µL, 1.17 mmol) were added, and the solution was stirred at room temperature for 2 h. Purification by preparative HPLC (10-45% AcCN/water with 0.035% TFA) followed by purification by silica gel chromatography (8% MeOH/DCM) gave the title compound as a white solid (28 mg, 28%). $^1$H NMR (500 MHz, DMSO-d$_6$) δ 0.90 (dd, J=6.5, 2.0 Hz, 3H), 1.06 (dd, J=6.5, 2.0 Hz, 3H), 2.42-2.51 (m, 1H), 3.61-3.75 (m, 1H), 4.15-4.68 (m, 4H), 4.95-5.21 (m, 3H), 7.09 (t, J=5.0 Hz, 1H), 7.81 (d, J=12.5 Hz, 1H), 8.27 (t, J=5.0 Hz, 1H). [M+H] calc'd for $C_{18}H_{19}N_5O_2$, 338; found, 338.

PREPARATION W: (R)-3,3-dimethyl-2-(3-oxopyrrolo[4,3,2-de][2,6]naphthyridin-4(1H,3H,5H)-yl)butanoic acid

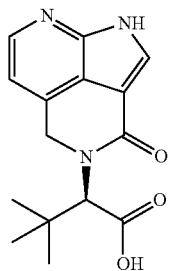 [SMILES: CC(C)(C)[C@H](C(=O)O)N1Cc2ccnc3[nH]cc(c23)C1=O]

STEP A: (R)-benzyl 2-amino-3,3-dimethylbutanoate, TFA salt

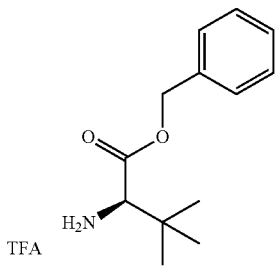 [SMILES: CC(C)(C)[C@@H](N)C(=O)OCc1ccccc1]

Benzyl bromide (2.26 mL, 19.0 mmol) was added to a stirred solution of (R)-2-(tert-butoxycarbonylamino)-3-3-dimethylbutanoic acid (4.0 g, 17.3 mmol) in AcCN (80 mL) at 0° C. DBU (3.13 mL, 20.8 mmol) was added slowly, and the solution was stirred for 3 h while warming to room temperature. The solution was concentrated in vacuo, taken up in EtOAc, and washed with aqueous HCl (1N), aqueous NaHCO$_3$ (sat.), and brine. The organics were dried over MgSO$_4$) and concentrated. The resulting clear oil was dissolved in TFA/DCM (50%, 16 mL) and stirred for 1 h at room temperature. The solution was concentrated and purified by short silica column (10% MeOH/DCM) to give the title compound as a white powder (5.02 g, 87%). $^1$H NMR (500 MHz, DMSO-d$_6$) δ 1.05 (s, 9H), 3.72 (s, 1H), 5.17 (AB q, J=40.0, 12.0 Hz, 2H), 7.25-7.35 (m, 5H), 8.20 (br s, 2H).

STEP B: (R)-benzyl 3,3-dimethyl-2-(3-oxo-1-tosylpyrrolo[4,3,2-de][2,6]naphthyridin-4(1H,3H,5H)-yl)butanoate

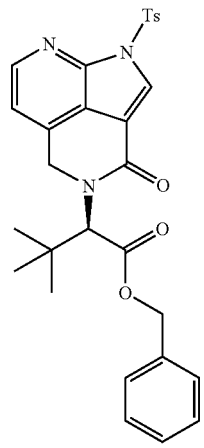 [SMILES: Cc1ccc(S(=O)(=O)n2cc3c4c(ccnc42)CN([C@@H](C(=O)OCc2ccccc2)C(C)(C)C)C3=O)cc1]

Sodium triacetoxyborohydride (665 mg, 3.14 mmol) and (R)-benzyl 2-amino-3,3-dimethylbutanoate, TFA salt (1.05 g, 2.85 mmol) were combined in DCM (15 mL). The reaction mixture was stirred for 20 min at room temperature and then cooled to 0° C. 4-Formyl-1-tosyl-1H-pyrrolo[2,3-b]pyridine-3-carboxylic acid (900 mg, 2.61 mmol) was added, and the reaction mixture was stirred for 1 h. The solution was concentrated in vacuo to afford a tan foam, which was re-dissolved in THF (40 mL). HATU (1.49 g, 3.92 mmol) and N-methylmorpholine (436 µL, 3.92 mmol) were added, and the reaction mixture was stirred at 52° C. for 2 h. Additional HATU (750 mg, 1.96 mmol) and N-methylmorpholine (218 µL, 1.96 mmol) were added. The reaction mixture was stirred for an additional 2 h, cooled, diluted with EtOAc, and washed with brine. The organics were dried over MgSO$_4$ and concentrated in vacuo. Purification by silica gel chromatography (1:2:2 EtOAc/Hexanes/DCM) gave the title compound as a pale yellow oil/foam (970 mg, 70%). $^1$H NMR (500 MHz, CDCl$_3$) δ 1.12 (s, 9H), 2.33 (s, 3H), 5.06 (AB q, J=66.5, 24.0 Hz, 2H), 5.11 (s, 2H), 5.48 (br s, 1H), 6.98 (d, J=5.0 Hz, 1H), 7.14-7.28 (m, 7H), 8.03-8.11 (m, 3H), 8.42 (d, J=5.0 Hz, 1H). [M+H] calc'd for $C_{29}H_{29}N_3O_5S$, 532; found, 532.

STEP C: (R)-3,3-dimethyl-2-(3-oxopyrrolo[4,3,2-de][2,6]naphthyridin-4(1H,3H,5H)-yl)butanoic acid A mixture of (R)-benzyl 3,3-dimethyl-2-(3-oxo-1-tosylpyrrolo[4,3,2-de][2,6]naphthyridin-4(1H,3H,5H)-yl)butanoate (950 mg, 1.79 mmol), MeOH (4 mL), and aqueous NaOH (1N, 2 mL) was stirred at room temperature for 40 min. The mixture was diluted with DCM and washed with brine. The organics were dried over MgSO$_4$ and concentrated in vacuo. Purification by silica gel chromatography (5% MeOH/DCM) gave a yellow oil (500 mg), which was taken up in MeOH and stirred with 10% Pd/C under a balloon of H$_2$ for 1 h at room temperature. The reaction mixture was filtered through Celite and concentrated in vacuo to give the title compound as an off-white solid (380 mg, 74%). $^1$H NMR (500 MHz, DMSO-d$_6$) δ 1.13 (s, 9H), 4.12 (br s, 1H), 5.05-

5.15 (m, 2H), 7.08 (d, J=5.0 Hz, 1H), 7.84 (d, J=2.5 Hz, 1H), 8.25 (d, J=5.0 Hz, 1H). [M+H] calc'd for $C_{15}H_7N_3O_3$, 288; found, 288.

Example 82

(R)-1-(3,3-dimethyl-2-(3-oxopyrrolo[4,3,2-de][2,6]naphthyridin-4(1H,3H,5H)-yl)butanoyl)azetidine-3-carbonitrile

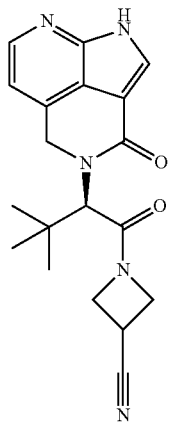 [SMILES: CC(C)(C)[C@H](C(=O)N1CC(C#N)C1)N1Cc2ccnc3[nH]cc(c23)C1=O]

(R)-3,3-Dimethyl-2-(3-oxopyrrolo[4,3,2-de][2,6]naphthyridin-4(1H,3H,5H)-yl)butanoic acid (80 mg, 0.278 mmol), HOBt hydrate (51.2 mg, 0.334 mmol), and EDC hydrochloride (80 mg, 0.418 mmol) were combined in DMF (2 mL). Azetidine-3-carbonitrile hydrochloride (49.5 mg, 0.418 mmol) and 4-methylmorpholine (0.124 mL, 1.114 mmol) were added, and the reaction mixture was stirred at room temperature for 2 h. The product was purified by preparative HPLC (10-50% AcCN/H$_2$O with 0.035% TFA), concentrated in vacuo, and purified by flash column chromatography (8% MeOH/DCM) to afford the title compound (38 mg, 39%). $^1$H NMR (500 MHz, CD$_3$OD) δ 1.17 (s, 9H), 3.58-3.72 (m, 1H), 4.13-4.65 (m, 4H), 5.35-5.45 (m, 3H), 7.28-7.38 (m, 1H), 7.95 (d, J=15.5 Hz, 1H), 8.33-8.40 (m, 1H). [M+H] calc'd for $C_{19}H_{21}N_5O_2$, 352; found, 352.

Example 83

(R)—N-(cyanomethyl)-3,3-dimethyl-2-(3-oxopyrrolo[4,3,2-de][2,6]naphthyridin-4(1H,3H,5H)-yl)butanamide

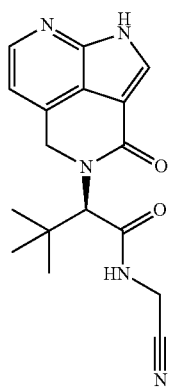 [SMILES: CC(C)(C)[C@H](C(=O)NCC#N)N1Cc2ccnc3[nH]cc(c23)C1=O]

(R)-3,3-Dimethyl-2-(3-oxopyrrolo[4,3,2-de][2,6]naphthyridin-4(1H,3H,5H)-yl)butanoic acid (40.0 mg, 0.139 mmol), HOBt hydrate (25.6 mg, 0.167 mmol), and EDC hydrochloride (40.0 mg, 0.209 mmol) were combined in DMF (2 mL). 2-Aminoacetonitrile (11.71 mg, 0.209 mmol) and 4-methylmorpholine (0.062 mL, 0.557 mmol) were added, and the reaction mixture was stirred at room temperature for 2 h. The product was purified by preparative HPLC (10-45% AcCN/H$_2$O with 0.035% TFA), concentrated in vacuo, and lyophilized to afford the title compound as a pale yellow solid (36 mg, 59%). $^1$H NMR (500 MHz, DMSO-d$_6$) δ 1.09 (s, 9H), 4.01-4.12 (m, 2H), 5.13-5.22 (m, 2H), 5.33 (br s, 1H), 7.10 (d, J=4.5 Hz, 1H), 7.87 (s, 1H), 8.26 (d, J=4.5 Hz, 1H), 8.86 (br s, 1H), 12.25 (br s, 1H). [M+H] calc'd for $C_{17}H_{19}N_5O_2$, 326; found, 326.

Example 84

(S)-1-((R)-2-(6-chloro-3-oxopyrrolo[4,3,2-de][2,6]naphthyridin-4(1H,3H,5H)-yl)-3-methylbutanoyl)pyrrolidine-2-carbonitrile

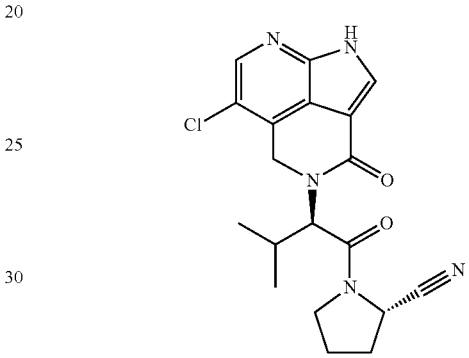

(R)-2-(6-Chloro-3-oxopyrrolo[4,3,2-de][2,6]naphthyridin-4(1H,3H,5H)-yl)-3-methylbutanoic acid (10 mg, 0.032 mmol), HATU (15 mg, 0.039 mmol), (S)-pyrrolidine-2-carbonitrile hydrochloride (4 mg, 0.032 mmol), and N-methylmorpholine (90 µL, 0.097 mmol) were combined in THF (0.5 mL). The reaction mixture was stirred under nitrogen at 40° C. for 10 min and then at room temperature for 30 min. The solution was concentrated and purified by preparative HPLC (10-50% AcCN/H$_2$O with 0.035% TFA) to afford the title compound as a yellow film (4 mg, 29%). $^1$H NMR (500 MHz, CD$_3$OD) δ 0.94 (d, J=6.9 Hz, 3H), 1.06 (d, J=6.3 Hz, 3H), 1.04-1.13 (m, 1H), 2.12-2.17 (m, 2H), 2.25-2.29 (m, 2H), 2.60-2.63 (m, 1H), 3.72-3.75 (m, 1H), 3.83-3.87 (m, 1H), 4.90 (d, J=13.7 Hz, 1H), 5.05 (d, J=12.7 Hz, 1H), 5.50 (d, J=7.3 Hz, 1H), 7.86 (s, 1H), 8.25 (s, 1H). [M+H] calc'd for $C_{19}H_{20}ClN_5O_2$, 386; found, 386.

Example 85

(R)-1-((R)-2-(6-chloro-3-oxopyrrolo[4,3,2-de][2,6]naphthyridin-4(1H,3H,5H)-yl)-3-methylbutanoyl)pyrrolidine-2-carbonitrile

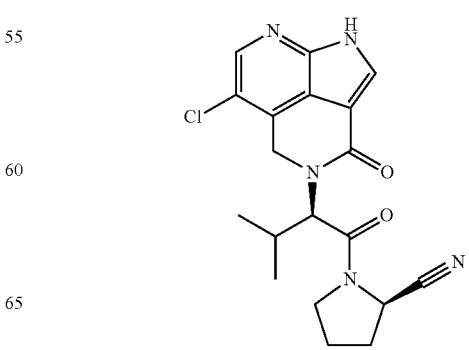

(R)-2-(6-Chloro-3-oxopyrrolo[4,3,2-de][2,6]naphthyridin-4(1H,3H,5H)-yl)-3-methylbutanoic acid (10 mg, 0.032 mmol), HATU (15 mg, 0.039 mmol), (R)-pyrrolidine-2-carbonitrile hydrochloride (4 mg, 0.032 mmol), and N-methylmorpholine (90 μL, 0.097 mmol) were combined in THF (0.5 mL). The reaction mixture was stirred under nitrogen at 40° C. for 10 min and then at room temperature for 30 min. The solution was concentrated and purified by preparative HPLC (10-50% AcCN/H₂O with 0.035% TFA) to afford the title compound as a white solid (2 mg, 18%). ¹H NMR (500 MHz, CD₃OD) δ 0.94 (d, J=6.9 Hz, 3H), 1.06 (d, J=6.3 Hz, 3H), 1.03-1.12 (m, 1H), 2.12-2.17 (m, 2H), 2.25-2.27 (m, 2H), 2.59-2.63 (m, 1H), 3.72-3.74 (m, 1H), 3.83-3.86 (m, 1H), 4.92 (d, J=5.9 Hz, 1H), 5.06 (d, J=13.2 Hz, 1H), 5.46 (d, J=11.8 Hz, 1H), 7.86 (s, 1H), 8.25 (s, 1H). [M+H] calc'd for C₁₉H₂₀ClN₅O₂, 386; found, 386.

Example 86

(2S,4S)-1-((R)-2-(6-chloro-3-oxopyrrolo[4,3,2-de][2,6]naphthyridin-4(1H,3H,5H)-yl)-3-methylbutanoyl)-4-fluoropyrrolidine-2-carbonitrile

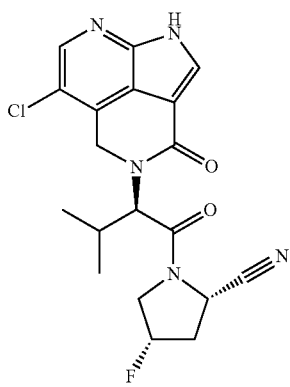 [SMILES: CC(C)[C@H](C(=O)N1C[C@@H](F)C[C@H]1C#N)N1Cc2c(Cl)cnc3[nH]cc(c23)C1=O]

(R)-2-(6-Chloro-3-oxopyrrolo[4,3,2-de][2,6]naphthyridin-4(1H,3H,5H)-yl)-3-methylbutanoic acid (10 mg, 0.032 mmol)), HATU (15 mg, 0.039 mmol), (2S,4S)-4-fluoropyrrolidine-2-carbonitrile (4 mg, 0.032 mmol), and N-methylmorpholine (90 μL, 0.097 mmol) were combined in THF (0.5 mL). The reaction mixture was stirred under nitrogen at 40° C. for 10 min and then at room temperature for 30 min. The solution was concentrated and purified by preparative HPLC (10-50% AcCN/H₂O with 0.035% TFA) to afford the title compound as a white solid (2 mg, 12%). ¹H NMR (500 MHz, CD₃OD) δ 0.94 (d, J=6.3 Hz, 3H), 1.05 (d, J=6.3 Hz, 3H), 1.03-1.15 (m, 1H), 2.56-2.65 (m, 3H), 23.89-3.91 (m, 1H), 4.25-4.30 (m, 1H), 4.83-4.87 (m, 1H), 5.09-5.13 (m, 1H), 5.39-5.41 (m, 1H), 5.47-5.66 (m, 1H), 7.87 (s, 1H), 8.27 (s, 1H). [M+H] calc'd for C₁₉H₁₉ClFN₅O₂, 404; found, 404.

PREPARATION X: (R)-3,3-dimethyl-2-(6-methyl-3-oxopyrrolo[4,3,2-de][2,6]naphthyridin-4(1H,3H, 5H)-yl)butanoic acid

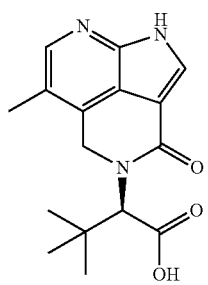 [SMILES: Cc1cnc2[nH]cc3c2c1CN([C@@H](C(=O)O)C(C)(C)C)C3=O]

STEP A: (R)-3,3-dimethyl-2-(6-methyl-3-oxo-1-tosylpyrrolo[4,3,2-de][2,6]naphthyridin-4(1H,3H, 5H)-yl)butanoic acid

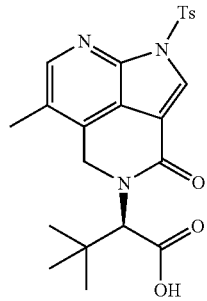 [SMILES: Cc1ccc(S(=O)(=O)n2cc3c4c(c(C)cnc42)CN([C@@H](C(=O)O)C(C)(C)C)C3=O)cc1]

(R)-Benzyl 2-(6-chloro-3-oxo-1-tosylpyrrolo[4,3,2-de][2,6]naphthyridin-4(1H,3H,5H)-yl)-3,3-dimethylbutanoate (10 mg, 0.018 mmol), Pd(Ph₃P)₄ (10 mg, 0.009 mmol), and dioxane (1 mL) were combined in a 2 mL microwave vial. The mixture was purged with nitrogen, and trimethylaluminum (2.0M/toluene, 0.053 mL, 0.11 mmol) was added. The vial was sealed and the reaction mixture was heated in a Biotage Initiator™ microwave for 1 h at 120° C. The reaction was repeated three times with an increased amount of (R)-benzyl 2-(6-chloro-3-oxo-1-tosylpyrrolo[4,3,2-de][2,6]naphthyridin-4(1H,3H,5H)-yl)-3,3-dimethylbutanoate (30 mg) in each reaction. The reaction mixtures were combined and the resulting mixture was concentrated and purified by preparative HPLC (30-70% AcCN/H₂O with 0.035% TFA) to afford the title compound as a yellow oil (36 mg, 44%). ¹H NMR (500 MHz, CD₃OD) δ 1.21 (s, 9H), 2.30 (s, 3H), 2.36 (s, 3H), 4.94 (s, 1H), 5.07 (d, J=18.6 Hz, 1 H), 5.21 (d, J=19.0 Hz, 1 H), 7.36 (d, J=8.3 Hz, 2 H), 8.04 (d, J=4.9 Hz, 2 H), 8.10 (s, 1 H), 8.22 (s, 1 H). [M+H] calc'd for C₂₃H₂₅N₃O₅S, 456; found, 456

STEP B: (R)-3,3-dimethyl-2-(6-methyl-3-oxopyrrolo[4,3,2-de][2,6]naphthyridin-4(1H,3H,5H)-yl)butanoic acid (R)-3,3-Dimethyl-2-(6-methyl-3-oxo-1-tosylpyrrolo[4,3,2-de][2,6]naphthyridin-4(1H,3H,5H)-yl)butanoic acid (36 mg, 0.079 mmol)) was dissolved in THF (3 mL), MeOH (3 mL) and aqueous NaOH (1N, 3 mL) in a 50 mL round bottom flask. The reaction mixture was heated at 50° C. for 30 min in an oil bath then cooled to room temperature. The solution was concentrated and purified by preparative HPLC (10-35% AcCN/H₂O with 0.035% TFA) to give the title compound (10 mg, 42%). ¹H NMR (500 MHz, CD₃OD) δ 1.25 (s, 9H), 2.29 (s, 3H), 4.87 (s, 1H), 5.21 (d, J=19.5 Hz, 1H), 5.37 (d, J=19.5 Hz, 1H), 7.87 (s, 1H), 8.23 (s, 1H). [M+H] calc'd for C₁₆H₁₉N₃O₃, 302; found, 302.

Example 87

(R)-1-(3,3-dimethyl-2-(6-methyl-3-oxopyrrolo[4,3,2-de][2,6]naphthyridin-4(1H,3H,5H)-yl)butanoyl)azetidine-3-carbonitrile

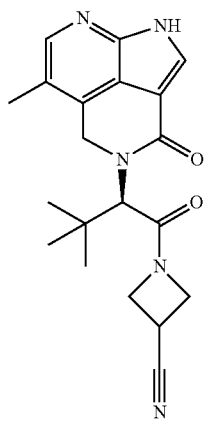 [SMILES: Cc1cnc2[nH]cc3c2c1CN([C@@H](C(=O)N1CC(C#N)C1)C(C)(C)C)C3=O]

(R)-3,3-Dimethyl-2-(6-methyl-3-oxopyrrolo[4,3,2-de][2,6]naphthyridin-4(1H,3H,5H)-yl)butanoic acid (10 mg, 0.033 mmol), DMAP (6 mg, 0.05 mmol), 4-methylmorpholine (0.015 mL, 0.13 mmol), EDC hydrochloride (10 mg, 0.050 mmol), HOBt hydrate (8 mg, 0.050 mmol) and azetidine-3-carbonitrile hydrochloride (6 mg, 0.050 mmol) were dissolved in DMF (2 mL). The reaction mixture was stirred under nitrogen at room temperature for 3 h. The solution was concentrated and purified by preparative HPLC (10-30% AcCN/H$_2$O with 0.035% TFA) to give the title compound (1.4 mg, 12%). $^1$H NMR (500 MHz, CD$_3$OD) δ 1.18 (s, 9H), 2.35 (d, J=8.8 Hz, 3H) 4.17-4.18 (m, 1 H), 4.29-4.31 (m, 2 H), 4.52-4.62 (m, 1 H), 4.64-4.69 (m, 1 H), 5.19-5.23 (m, 2 H), 5.45 (s, 1 H), 7.83 (d, J=16.1 Hz, 3 H), 8.19 (s, 1 H). [M+H] calc'd for C$_{20}$H$_{23}$N$_5$O$_2$, 366; found, 366

Example 88

(R)-1-(3-methyl-2-(6-methyl-3-oxopyrrolo[4,3,2-de][2,6]naphthyridin-4(1H,3H,5H)-yl)butanoyl)azetidine-3-carbonitrile

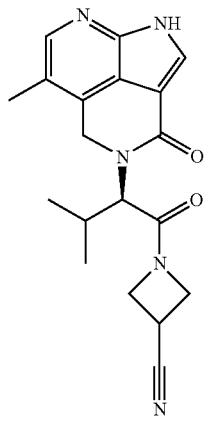 [SMILES: Cc1cnc2[nH]cc3c2c1CN([C@@H](C(=O)N1CC(C#N)C1)C(C)C)C3=O]

(R)-1-(2-(6-chloro-3-oxopyrrolo[4,3,2-de][2,6]naphthyridin-4(1H,3H,5H)-yl)-3-methylbutanoyl)azetidine-3-carbonitrile (30 mg, 0.081 mmol), Pd(Ph$_3$P)$_4$ (47 mg, 0.04 mmol), and dioxane (2 mL) were combined in a 5 mL microwave vial. The mixture was purged with nitrogen, and trimethylaluminum (2.0M/toluene, 0.24 mL, 0.48 mmol) was added. The vial was sealed and the reaction mixture was heated in a Biotage Initiator™ microwave for 1 h at 120° C. The reaction was repeated 4 times at the same scale. The reaction mixtures were combined, and the resulting mixture was quenched with water (0.5 mL), concentrated, and purified by preparative HPLC (10-30% AcCN/H$_2$O with 0.035% TFA) followed by flash chromatography (5% MeOH/95% DCM) to give the title compound as a light yellow solid (41 mg, 29%). $^1$H NMR (500 MHz, CD$_3$OD) δ 0.92 (d, J=6.8 Hz, 3H), 1.07 (dd, J=15.9, 6.1 Hz, 3H), 2.42 (d, J=6.35 Hz, 3H), 3.69-3.77 (m, 1H), 4.19-4.22 (m, 1H), 4.32-4.34 (m, 1H), 4.53-4.59 (m, 1H), 4.68-4.72 (m, 1H), 5.20-5.33 (m, 3H), 7.98 (d, J=19.5 Hz, 1H), 8.27 (s, 1H). [M+H] calc'd for C$_{19}$H$_{21}$N$_5$O$_2$, 352; found, 352.

Table 2, below, lists JAK3 and JAK2 inhibition data for many of the compounds described in the examples. The compounds were tested in accordance with the assay described on page 27 of the specification. The inhibition data is reported as pIC$_{50}$, i.e., $-\log_{10}(IC_{50})$, where IC$_{50}$ is the molar concentration at 50% inhibition. Larger pIC$_{50}$ values represent higher potency.

TABLE 2

JAK2 and JAK3 Inhibition

| Example No. | JAK3 pIC$_{50}$ | JAK2 pIC50 |
|---|---|---|
| 2 | 5.4 | 5.2 |
| 3 | 5.8 | 6.1 |
| 6 | 6.3 | 7.1 |
| 9 | 8.0 | 7.7 |
| 10 | 7.0 | 7.1 |
| 11 | 6.5 | 6.4 |
| 12 | 5.1 | 5.5 |
| 13 | 5.5 | 5.3 |
| 16 | 7.3 | 8.0 |
| 17 | 7.9 | 8.3 |
| 18 | 4.7 | 4.7 |
| 19 | 6.5 | 5.4 |
| 20 | 7.1 | 5.8 |
| 21 | 6.9 | 6.1 |
| 22 | 7.5 | 6.2 |
| 23 | 6.4 | 5.4 |
| 24 | 5.8 | 4.9 |
| 25 | 6.7 | 5.8 |
| 26 | 8.0 | 6.9 |
| 27 | 6.6 | 5.5 |
| 28 | 6.4 | 5.0 |
| 29 | 6.8 | 5.5 |
| 30 | 5.9 | 5.5 |
| 31 | 4.7 | 4.7 |
| 32 | 8.0 | 6.7 |
| 33 | 7.4 | 6.1 |
| 34 | 7.8 | 6.6 |
| 35 | 6.5 | 5.6 |
| 36 | 6.9 | 6.0 |
| 37 | 7.2 | 5.8 |
| 38 | 7.5 | 6.0 |
| 39 | 8.7 | 7.5 |
| 40 | 7.3 | 5.9 |
| 41 | 8.4 | 7.3 |
| 42 | 8.2 | 6.9 |
| 43 | 6.1 | 4.9 |
| 44 | 6.9 | 5.8 |
| 45 | 7.2 | 5.7 |
| 46 | 6.6 | 5.8 |
| 47 | 6.9 | 5.6 |
| 48 | 6.6 | 5.3 |
| 49 | 7.0 | 5.7 |
| 50 | 7.1 | 5.8 |
| 51 | 8.3 | 6.8 |

115

TABLE 2-continued

JAK2 and JAK3 Inhibition

| Example No. | JAK3 pIC$_{50}$ | JAK2 pIC50 |
|---|---|---|
| 52 | 8.0 | 6.7 |
| 53 | 7.9 | 6.6 |
| 54 | 5.7 | 4.5 |
| 55 | 6.0 | 4.9 |
| 56 | 6.2 | 5.0 |
| 57 | 7.1 | 5.8 |
| 58 | 6.5 | 5.5 |
| 59 | 5.2 | 4.7 |
| 60 | 6.1 | 5.0 |
| 61 | 5.2 | 4.7 |
| 62 | 5.8 | 4.9 |
| 63 | 6.2 | 5.2 |
| 64 | 5.6 | 4.7 |
| 65 | 5.7 | 5.2 |
| 66 | 5.4 | 4.7 |
| 67 | 6.6 | 5.3 |
| 68 | 5.6 | 4.7 |
| 69 | 6.2 | 5.0 |
| 70 | 6.3 | 5.0 |
| 71 | 6.1 | 5.3 |
| 72 | 6.9 | 5.7 |
| 73 | 6.8 | 5.5 |
| 74 | 6.1 | 5.1 |
| 75 | 7.5 | 6.1 |
| 76 | 7.2 | 6.0 |
| 77 | 7.2 | 5.8 |
| 78 | 5.4 | 5.0 |
| 79 | 6.9 | 5.6 |
| 80 | 7.8 | 6.4 |
| 81 | 8.3 | 6.9 |
| 82 | 8.7 | 7.4 |
| 83 | 7.9 | 6.6 |
| 84 | 6.7 | 5.5 |
| 85 | 7.0 | 5.8 |
| 86 | 7.6 | 6.4 |
| 87 | 8.5 | 7.3 |
| 88 | 8.8 | 7.6 |

What is claimed is:

1. A method for inhibition of JAK2 and/or JAK3 in a subject suffering from a disease associated with JAK2 and/or JAK3, the method comprising administering to the subject a compound of formula I

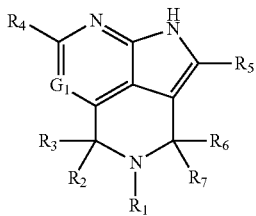

or a pharmaceutically acceptable salt thereof, wherein:
$G_1$ is selected from the group consisting of $CR_8$;
$R_1$ is selected from the group consisting of optionally substituted $C_{3-8}$ cycloalkyl, optionally substituted $C_{3-6}$ heterocycloalkyl, optionally substituted $C_{4-14}$ aryl, optionally substituted $C_{1-10}$ heteroaryl, and optionally substituted $C_{1-6}$ alkyl;
$R_2$ and $R_3$ are each independently selected from the group consisting of hydrogen and optionally substituted $C_{1-4}$ alkyl, or $R_2$, $R_3$, and the carbon atom to which they are attached form a carbonyl;
$R_4$ is selected from the group consisting of hydrogen, optionally substituted $C_{1-4}$ alkyl, optionally substituted $C_{1-4}$ alkoxy, halo, hydroxy, and amino;

$R_5$ is selected from the group consisting of hydrogen, optionally substituted $C_{1-4}$ alkyl, $C_{3-8}$ cycloalkyl, and halo;
$R_6$ and $R_7$ are each independently selected from the group consisting of hydrogen and optionally substituted $C_{1-4}$ alkyl, or $R_6$, $R_7$, and the carbon atom to which they are attached form a carbonyl;
$R_8$ is selected from the group consisting of hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, and halo; and
with the proviso that no more than one carbonyl is formed from $R_2$ and $R_3$ and $R_6$ and $R_7$.

2. A method according to claim 1, wherein each of $R_4$ and $R_5$ are hydrogen.

3. A method according to claim 1, wherein G is $CR_8$ and $R_8$ is selected from hydrogen, halo, and optionally substituted $C_{1-6}$ alkyl.

4. A method according to claim 3, wherein G is $CR_8$ and $R_8$ is selected from hydrogen, halo, and $C_{1-4}$ alkyl.

5. A method according to claim 1, wherein $R_1$ is optionally substituted $C_{3-8}$ cycloalkyl.

6. A method according to claim 1, wherein $R_1$ is optionally substituted $C_{3-6}$ heterocycloalkyl.

7. A method according to claim 1, wherein $R_1$ is optionally substituted $C_{4-14}$ aryl.

8. A method according to claim 1, wherein $R_1$ is optionally substituted $C_{1-10}$ heteroaryl.

9. A method according to claim 1, wherein $R_1$ is optionally substituted $C_{1-6}$ alkyl.

10. A method according to claim 1, wherein $R_2$, $R_3$, and the carbon atom to which they are attached form a carbonyl.

11. A method according to claim 10, wherein each of $R_6$ and $R_7$ is hydrogen.

12. A method according to claim 1, wherein $R_6$, $R_7$, and the carbon atom to which they are attached form a carbonyl.

13. A method according to claim 12, wherein each of $R_2$ and $R_3$ is hydrogen.

14. A method according to claim 1, in which the compound is selected from:
tert-butyl 4-(5-oxopyrrolo[4,3,2-de][2,6]naphthyridin-4(1H,3H,5H)-yl)piperidine-1-carboxylate;
4-(piperidin-4-yl)-3,4-dihydropyrrolo[4,3,2-de][2,6]naphthyridin-5(1H)-one;
3-oxo-3-(4-(5-oxopyrrolo[4,3,2-de][2,6]naphthyridin-4(1H,3H,5H)-yl)piperidin-1-yl)propanenitrile;
tert-butyl 4-methyl-4-(5-oxopyrrolo[4,3,2-de][2,6]naphthyridin-4(1H,3H,5H)-yl)piperidine-1-carboxylate;
4-(4-methylpiperidin-4-yl)-3,4-dihydropyrrolo[4,3,2-de][2,6]naphthyridin-5(1H)-one;
3-(4-methyl-4-(5-oxopyrrolo[4,3,2-de][2,6]naphthyridin-4(1H,3H,5H)-yl)piperidin-1-yl)-3-oxopropanenitrile;
tert-butyl 4-ethyl-4-(5-oxopyrrolo[4,3,2-de][2,6]naphthyridin-4(1H,3H,5H)-yl)piperidine-1-carboxylate;
4-(4-ethylpiperidin-4-yl)-3,4-dihydropyrrolo[4,3,2-de][2,6]naphthyridin-5(1H)-one;
3-(4-ethyl-4-(5-oxopyrrolo[4,3,2-de][2,6]naphthyridin-4(1H,3H,5H)-yl)piperidin-1-yl)-3-oxopropanenitrile;
4-(pentan-3-yl)-3,4-dihydropyrrolo[4,3,2-de][2,6]naphthyridin-5(1H)-one;
4-(1-cyclopropyl-3-hydroxypropyl)-3,4-dihydropyrrolo[4,3,2-de][2,6]naphthyridin-5(1H)-one;
tert-butyl 3-((5-oxopyrrolo[4,3,2-de][2,6]naphthyridin-4(1H,3H,5H)-yl)methyl)pyrrolidine-1-carboxylate;
4-(pyrrolidin-3-ylmethyl)-3,4-dihydropyrrolo[4,3,2-de][2,6]naphthyridine-5(1H)-one;
tert-butyl 3-(5-oxopyrrolo[4,3,2-de][2,6]naphthyridin-4(1H,3H,5H)-yl)piperidine-1-carboxylate;

4-(piperidin-3-yl)-3,4-dihydropyrrolo[4,3,2-de][2,6]
  naphthyridin-5(1H)-one;
4-(4-ethyl-1-propionylpiperidin-4-yl)-3,4-dihydropyrrolo
  [4,3,2-de][2,6]naphthyridin-5(1H)-one;
4-(4-ethyl-1-(pyrimidin-4-yl) piperidin-4-yl)-3,4-dihydropyrrolo [4,3,2-de][2,6]naphthyridin-5(1H)-one;
(S)-4-(1-oxo-1-(pyrrolidin-1-yl)butan-2-yl)-4,5-dihydropyrrolo [4,3,2-de][2,6]naphthyridin-3(1H)-one;
(R)-4-(1-oxo-1-(pyrrolidin-1-yl)butan-2-yl)-4,5-dihydropyrrolo [4,3,2-de][2,6]naphthyridin-3(1H)-one;
(R)-4-(3-methyl-1-oxo-1-(pyrrolidin-1-yl)butan-2-yl)-4,5-dihydropyrrolo [4,3,2-de][2,6]naphthyridin-3(1H)-one;
(R)-4-(4-methyl-1-oxo-1-(pyrrolidin-1-yl)pentan-2-yl)-4,5-dihydropyrrolo [4,3,2-de][2,6]naphthyridin-3(1H)-one;
(R)-N-cyclopentyl-3-methyl-2-(3-oxopyrrolo [4,3,2-de][2,6]naphthyridin-4(1H,3H,5H)-yl)butanamide;
(2R,3R)-N-cyclopentyl-3-methyl-2-(3-oxopyrrolo [4,3,2-de][2,6]naphthyridin-4(1H,3H,5H)-yl)pentanamide;
(2R,3S)-N-cyclopentyl-3-methyl-2-(3-oxopyrrolo [4,3,2-de][2,6]naphthyridin-4(1H,3H,5H)-yl)pentanamide;
(R)-N-cyclopentyl-2-cyclopropyl-2-(3-oxopyrrolo [4,3,2-de][2,6]naphthyridin-4(1H,3H,5H)-yl)acetamide;
(R)-N-cyclopentyl-3,3-dimethyl-2-(3-oxopyrrolo [4,3,2-de][2,6]naphthyridin-4(1H,3H,5H)-yl)butanamide;
(R)-N,2-dicyclopentyl-2-(3-oxopyrrolo [4,3,2-de][2,6]naphthyridin-4(1H,3H,5H)-yl)acetamide;
(R)-N-cyclopentyl-4,4,4-trifluoro-2-(3-oxopyrrolo [4,3,2-de][2,6]naphthyridin-4(1H,3H,5H)-yl)butanamide;
(R)-N-cyclopentyl-3-hydroxy-3-methyl-2-(3-oxopyrrolo [4,3,2-de][2,6]naphthyridin-4(1H,3H,5H)-yl)butanamide;
(R)-2-(6-chloro-3-oxopyrrolo [4,3,2-de][2,6]naphthyridin-4(1H,3H,5H)-yl)-3-cyano-N-cyclopentylpropanamide;
N-cyclopentyl-1-(3-oxopyrrolo [4,3,2-de][2,6]naphthyridin-4(1H,3H,5H)-yl)cyclopentanecarboxamide;
(R)-2-(6-chloro-3-oxopyrrolo[4,3,2-de][2,6]naphthyridin-4(1H,3H,5H)-yl)-N-(cyanomethyl)-3-methylbutanamide;
1-((R)-2-(6-chloro-3-oxopyrrolo[4,3,2-de][2,6]naphthyridin-4(1H,3H,5H)-yl)-3-methylbutanoyl)pyrrolidine-3-carbonitrile;
(R)-1-(2-(6-chloro-3-oxopyrrolo[4,3,2-de][2,6]naphthyridin-4(1H,3H,5H)-yl)-3-methylbutanoyl)piperidine-4-carbonitrile;
(R)-2-(6-chloro-3-oxopyrrolo[4,3,2-de][2,6]naphthyridin-4(1H,3H,5H)-yl)-N-(4-cyanophenyl)-3-methylbutanamide;
(R)-2-(6-chloro-3-oxopyrrolo[4,3,2-de][2,6]naphthyridin-4(1H,3H,5H)-yl)-N-(3-cyanophenyl)-3-methylbutanamide;
(R)-2-(6-chloro-3-oxopyrrolo[4,3,2-de][2,6]naphthyridin-4(1H,3H,5H)-yl)-N-((S)-1-cyanobutan -2-yl)-3-methylbutanamide;
(R)-2-(6-chloro-3-oxopyrrolo[4,3,2-de][2,6]naphthyridin-4(1H,3H,5H)-yl)-N-((R)-1-cyanobutan -2-yl)-3-methylbutanamide;
(R)-1-(2-(6-chloro-3-oxopyrrolo[4,3,2-de][2,6]naphthyridin-4(1H,3H,5H)-yl)-3-methylbutanoyl)azetidine-3-carbonitrile;
(R)-2-(6-chloro-3-oxopyrrolo[4,3,2-de][2,6]naphthyridin-4(1H,3H,5H)-yl)-N-(2-cyanoethyl)-3,3-dimethylbutanamide;
(R)-1-(2-(6-chloro-3-oxopyrrolo[4,3,2-de][2,6]naphthyridin-4(1H,3H,5H)-yl)-3,3-dimethylbutanoyl)azetidine-3-carbonitrile;
(R)-1-(2-(6-fluoro-3-oxopyrrolo[4,3,2-de][2,6]naphthyridin-4(1H,3H,5H)-yl)-3-methylbutanoyl)azetidine-3-carbonitrile;
(R)-2-(6-fluoro-3-oxopyrrolo[4,3,2-de][2,6]naphthyridin-4(1H,3H,5H)-yl)-3-methylbutanoic acid;
(2R)-2-(6-fluoro-3-oxopyrrolo[4,3,2-de][2,6]naphthyridin-4(1H,3H,5H)-yl)-3-methyl-N-(tetrahydrofuran-3-yl)butanamide;
(R)-2-(6-fluoro-3-oxopyrrolo[4,3,2-de][2,6]naphthyridin-4(1H,3H,5H)-yl)-3-methyl-N-(1,1-dioxidotetrahydrothien-3-yl)butanamide;
(R)-2-(6-fluoro-3-oxopyrrolo[4,3,2-de][2,6]naphthyridin-4(1H,3H,5H)-yl)-3-methyl-N-(2-(methylsulfonyl)ethyl)butanamide;
(R)-N-(1,1 -dioxidotetrahydro-2H-thiopyran-4-yl)-2-(6-fluoro-3-oxopyrrolo[4,3,2-de][2,6]naphthyridin-4(1H,3H,5H)-yl)-3-methylbutanamide;
4-{(1R)-1-[(1,1-dioxidothiomorpholin-4-yl)carbonyl]-2-methylpropyl}-6-fluoro-4,5-dihydropyrrolo[4,3,2-de][2,6]naphthyridin-3(1H)-one;
(R)-N-(cyclopropylmethoxy)-2-(6-fluoro-3-oxopyrrolo[4,3,2-de][2,6]naphthyridin-4(1H,3H,5H)-yl)-3-methylbutanamide;
(2R)-N-(3,3-difluorocyclopentyl)-2-(6-fluoro-3-oxopyrrolo[4,3,2-de][2,6]naphthyridin-4(1H,3H,5H)-yl)-3-methylbutanamide;
(R)-3-(fluoromethyl)-1-(3-methyl-2-(3-oxopyrrolo[4,3,2-de][2,6]naphthyridin-4(1H,3H,5H)-yl)butanoyl)azetidine-3-carbonitrile;
(R)-1-(2-(6-fluoro-3-oxopyrrolo[4,3,2-de][2,6]naphthyridin-4(1H,3H,5H)-yl)-3-methylbutanoyl)-3-methylazetidine-3-carbonitrile;
(R)-3-methyl-1-(3-methyl-2-(3-oxopyrrolo[4,3,2-de][2,6]naphthyridin-4(1H,3H,5H)-yl)butanoyl)azetidine-3-carbonitrile;
(R)-4-(1-morpholino-1-oxobutan-2-yl)-4,5-dihydropyrrolo[4,3,2-de][2,6]naphthyridin-3(1H)-one;
(R)-4-(1-(4-methylpiperazin-1-yl)-1-oxobutan-2-yl)-4,5-dihydropyrrolo[4,3,2-de][2,6]naphthyridin-3(1H)-one;
4-((2R)-1-(3-hydroxypyrrolidin-1-yl)-1-oxobutan-2-yl)-4,5-dihydropyrrolo[4,3,2-de][2,6]naphthyridin-3(1H)-one;
(R)-N-cyclopentyl-2-(3-oxopyrrolo[4,3,2-de][2,6]naphthyridin-4(1H,3H,5H)-yl)butanamide;
4-((2R)-1-(3-(4-fluorophenyl)pyrrolidin-1-yl)-1-oxobutan-2-yl)-4,5-dihydropyrrolo[4,3,2-de][2,6]naphthyridin-3(1H)-one;
4-((2R)-1-(3-(dimethylamino)pyrrolidin-1-yl)-1-oxobutan-2-yl)-4,5-dihydropyrrolo[4,3,2-de][2,6]naphthyridin-3(1H)-one;
4-((2R)-1-(3-(methoxymethyl)pyrrolidin-1-yl)-1-oxobutan-2-yl)-4,5-dihydropyrrolo[4,3,2-de][2,6]naphthyridin-3(1H)-one;
4-((2R)-1-(3-methylpiperidin-1-yl)-1-oxobutan-2-yl)-4,5-dihydropyrrolo[4,3,2-de][2,6]naphthyridin-3(1H)-one;
(R)-4-(1-(4-(2-hydroxypropan-2-yl)piperidin-1-yl)-1-oxobutan-2-yl)-4,5-dihydropyrrolo[4,3,2-de][2,6]naphthyridin-3(1H)-one;
(R)-4-(1-(4-(methylsulfonyl)piperazin-1-yl)-1-oxobutan-2-yl)-4,5-dihydropyrrolo[4,3,2-de][2,6]naphthyridin-3(1H)-one;
(R)-4-(1-oxo-1-(4-(pyridin-2-yl)piperazin-1-yl)butan-2-yl)-4,5-dihydropyrrolo[4,3,2-de][2,6]naphthyridin-3(1H)-one;
(R)-N-cyclopropyl-2-(3-oxopyrrolo[4,3,2-de][2,6]naphthyridin -4(1H,3H,5H)-yl)butanamide;
(R)-N-(cyclopropylmethyl)-2-(3-oxopyrrolo[4,3,2-de][2,6]naphthyridin-4(1H,3H,5H)-yl)butanamide;

(R)-N-isobutyl-2-(3-oxopyrrolo[4,3,2-de][2,6]naphthyridin-4(1H,3H,5H)-yl)butanamide;
(R)-N-isobutyl-N-methyl-2-(3-oxopyrrolo[4,3,2-de][2,6]naphthyridin-4(1H,3H,5H)-yl)butanamide;
(2R)-N-(1-hydroxypropan-2-yl)-2-(3-oxopyrrolo[4,3,2-de][2,6]naphthyridin-4(1H,3H,5H)-yl)butanamide;
(R)-N-(2-hydroxy-2-methylpropyl)-2-(3-oxopyrrolo[4,3,2-de][2,6]naphthyridin-4(1H,3H,5H)-yl)butanamide;
(R)-N-((S)-2,3-dihydroxypropyl)-2-(3-oxopyrrolo[4,3,2-de][2,6]naphthyridin-4(1H,3H,5H)-yl)butanamide;
(R)-2-(3-oxopyrrolo[4,3,2-de][2,6]naphthyridin-4(1H,3H,5H)-yl)-N-phenylbutanamide;
(R)-N-(1-(methylsulfonyl)piperidin-4-yl)-2-(3-oxopyrrolo[4,3,2-de][2,6]naphthyridin-4(1H,3H,5H)-yl)butanamide;
(2R)-2-(3-oxopyrrolo[4,3,2-de][2,6]naphthyridin-4(1H,3H,5H)-yl)-N-((tetrahydrofuran-2-yl)methyl)butanamide;
(2R)-N-(1-cyano ethyl)-2-(6-fluoro-3-oxopyrrolo[4,3,2-de][2,6]naphthyridin-4(1H,3H,5H)-yl)-3-methylbutanamide;
(R)-4-(1-(3,3-difluoroazetidin-1-yl)-3-methyl-1-oxobutan-2-yl)-6-fluoro-4,5-dihydropyrrolo[4,3,2-de][2,6]naphthyridin-3(1H)-one;
(R)-4-(1-(1,1-dioxidothiazolidin-3-yl)-3-methyl-1-oxobutan-2-yl)-6-fluoro-4,5-dihydropyrrolo[4,3,2-de][2,6]naphthyridin-3(1H)-one;
(R)-2-(6-fluoro-3-oxopyrrolo[4,3,2-de][2,6]naphthyridin-4(1H,3H,5H)-yl)-N,3-dimethyl-N-(2-(methylsulfonyl)ethyl)butanamide;
(R)-N-(cyanomethyl)-2-(6-fluoro-3-oxopyrrolo[4,3,2-de][2,6]naphthyridin-4(1H,3H,5H)-yl)-N,3-dimethylbutanamide;
(R)-4-(1-(3-(difluoromethyl)azetidin-1-yl)-3-methyl-1-oxobutan-2-yl)-6-fluoro-4,5-dihydropyrrolo[4,3,2-de][2,6]naphthyridin-3(1H)-one;
(R)-1-(3-methyl-2-(3-oxopyrrolo[4,3,2-de][2,6]naphthyridin-4(1H,3H,5H)-yl)butanoyl)azetidine-3-carbonitrile;
(R)-1-(3,3-dimethyl-2-(3-oxopyrrolo[4,3,2-de][2,6]naphthyridin-4(1H,3H,5H)-yl)butanoyl)azetidine-3-carbonitrile;
(R)-N-(cyanomethyl)-3,3-dimethyl-2-(3-oxopyrrolo[4,3,2-de][2,6]naphthyridin-4(1H,3H,5H)-yl)butanamide;
(S)-1-((R)-2-(6-chloro-3-oxopyrrolo[4,3,2-de][2,6]naphthyridin-4(1H,3H,5H)-yl)-3-methylbutanoyl)pyrrolidine-2-carbonitrile;
(R)-1-((R)-2-(6-chloro-3-oxopyrrolo[4,3,2-de][2,6]naphthyridin-4(1H,3H,5H)-yl)-3-methylbutanoyl)pyrrolidine-2-carbonitrile;
(2S,4S)-1-((R)-2-(6-chloro-3-oxopyrrolo[4,3,2-de][2,6]naphthyridin-4(1H,3H,5H)-yl)-3-methylbutanoyl)-4-fluoropyrrolidine-2-carbonitrile;
(R)-1-(3,3-dimethyl-2-(6-methyl-3-oxopyrrolo[4,3,2-de][2,6]naphthyridin-4(1H,3H,5H)-yl)butanoyl)azetidine-3-carbonitrile;
(R)-1-(3-methyl-2-(6-methyl-3-oxopyrrolo[4,3,2-de][2,6]naphthyridin-4(1H,3H,5H)-yl)butanoyl)azetidine-3-carbonitrile;
stereoisomers of any of the aforementioned compounds; and
pharmaceutically acceptable salts of any one of the aforementioned stereoisomers or compounds.

15. A method according to claim 1, further comprising administering at least one additional pharmacologically active agent.

16. A method according to claim 15, wherein the additional pharmacologically active agent is a DMARD.

17. A method according to claim 16, wherein the DMARD is methotrexate.

\* \* \* \* \*